US012759973B2

(12) United States Patent
Jewett et al.

(10) Patent No.: US 12,759,973 B2
(45) Date of Patent: Oct. 13, 2026

(54) AMINO ACIDS

(71) Applicant: Parabilis Medicines, Inc., Cambridge, MA (US)

(72) Inventors: Ivan Tucker Jewett, Boston, MA (US); Lorenzo Josue Alfaro-Lopez, Belmont, MA (US); Yue-Mei Zhang, Wellesley, MA (US); Brian Halbert White, Malden, MA (US)

(73) Assignee: PARABILIS MEDICINES, INC., Cambridge, MA (US)

( * ) Notice: Subject to any disclaimer, the term of this patent is extended or adjusted under 35 U.S.C. 154(b) by 767 days.

(21) Appl. No.: 18/017,033

(22) PCT Filed: Jul. 22, 2021

(86) PCT No.: PCT/US2021/042854

§ 371 (c)(1),
(2) Date: Jan. 19, 2023

(87) PCT Pub. No.: WO2022/020651

PCT Pub. Date: Jan. 27, 2022

(65) Prior Publication Data

US 2023/0271917 A1 Aug. 31, 2023

Related U.S. Application Data

(60) Provisional application No. 63/208,491, filed on Jun. 8, 2021, provisional application No. 63/055,301, filed on Jul. 22, 2020.

(51) Int. Cl.

| | |
|---|---|
| ***C07C 271/12*** | (2006.01) |
| ***C07C 229/26*** | (2006.01) |
| ***C07C 327/28*** | (2006.01) |
| ***C07D 207/16*** | (2006.01) |
| ***C07D 209/66*** | (2006.01) |
| ***C07D 249/04*** | (2006.01) |

(52) U.S. Cl.
CPC .......... *C07C 271/12* (2013.01); *C07C 229/26* (2013.01); *C07C 327/28* (2013.01); *C07D 207/16* (2013.01); *C07D 209/66* (2013.01); *C07D 249/04* (2013.01); *C07C 2603/18* (2017.05)

(58) Field of Classification Search
None
See application file for complete search history.

(56) References Cited

U.S. PATENT DOCUMENTS

| | | | |
|---|---|---|---|
| 6,313,092 | B1 | 11/2001 | Holladay et al. |
| 6,337,423 | B1 | 1/2002 | Axt et al. |
| 6,369,034 | B1 | 4/2002 | Doherty et al. |
| 8,592,377 | B2 | 11/2013 | Verdine et al. |
| 9,121,024 | B2 | 9/2015 | Tian et al. |
| 9,163,330 | B2 | 10/2015 | Verdine et al. |
| 9,556,227 | B2 | 1/2017 | Verdine et al. |
| 9,617,309 | B2 | 4/2017 | Verdine et al. |
| 10,081,654 | B2 | 9/2018 | Verdine et al. |
| 10,227,390 | B2 | 3/2019 | Verdine et al. |
| 10,301,351 | B2 | 5/2019 | Verdine et al. |
| 10,533,039 | B2 | 1/2020 | Verdine et al. |
| 11,198,713 | B2 | 12/2021 | Hilinski et al. |
| 11,332,496 | B2 | 5/2022 | Verdine et al. |
| 11,377,476 | B2 | 7/2022 | Verdine et al. |
| 2009/0028807 | A1 | 1/2009 | Giustiniani et al. |
| 2015/0225471 | A1 | 8/2015 | Liang et al. |
| 2016/0244494 | A1 | 8/2016 | Verdine et al. |
| 2016/0257725 | A1 | 9/2016 | Verdine et al. |
| 2018/0009847 | A1 | 1/2018 | Verdine et al. |
| 2018/0010001 | A1 | 1/2018 | Hersam et al. |
| 2018/0057565 | A1 | 3/2018 | Liang et al. |
| 2018/0303093 | A1 | 10/2018 | Namba et al. |
| 2021/0179665 | A1 | 6/2021 | McGee et al. |
| 2022/0177522 | A1 | 6/2022 | Verdine et al. |
| 2022/0213154 | A1 | 7/2022 | Hilinski et al. |
| 2022/0306708 | A1 | 9/2022 | Verdine et al. |
| 2022/0372075 | A1 | 11/2022 | Verdine et al. |
| 2023/0046728 | A1 | 2/2023 | Chandhoke et al. |
| 2023/0137773 | A1 | 5/2023 | Verdine et al. |
| 2023/0357320 | A1 | 11/2023 | Verdine et al. |

FOREIGN PATENT DOCUMENTS

| | | | |
|---|---|---|---|
| EP | 2706057 A1 | 3/2014 | |
| WO | WO-2005/079865 A1 | 9/2005 | |
| WO | WO-2008/121767 A2 | 10/2008 | |
| WO | WO-2011/008260 A2 | 1/2011 | |
| WO | WO-2011/104378 A1 | 9/2011 | |
| WO | WO-2014/052647 A2 | 4/2014 | |
| WO | WO-2014/055564 A1 | 4/2014 | |
| WO | WO-2014/159969 A1 | 10/2014 | |
| WO | WO-2014/201370 A1 | 12/2014 | |
| WO | WO-2015/051030 A2 | 4/2015 | |
| WO | WO-2015/150555 A1 | 10/2015 | |

(Continued)

OTHER PUBLICATIONS

U.S. Appl. No. 17/751,451, filed May 23, 2022, Verdine et al.
U.S. Appl. No. 17/912,029, filed Sep. 15, 2022, Verdine et al.
U.S. Appl. No. 18/017,024, filed Jan. 19, 2023, White et al.
U.S. Appl. No. 18/345,550, filed Jun. 30, 2023, Verdine et al.
U.S. Appl. No. 18/453,118, filed Aug. 21, 2023, Verdine et al.
U.S. Appl. No. 18/497,597, filed Oct. 30, 2023, Tokareva et al.
U.S. Appl. No. 18/542,556, filed Dec. 15, 2023, White et al.
U.S. Appl. No. 18/542,569, filed Dec. 15, 2023, Hurov et al.
U.S. Appl. No. 18/568,212, filed Dec. 7, 2023, White et al.

(Continued)

*Primary Examiner* — Amy C Bonaparte
(74) *Attorney, Agent, or Firm* — Choate, Hall & Stewart LLP; Xiaodong Li; William C. Howland, III

(57) ABSTRACT

In some embodiments, the present disclosure provides amino acid compounds that are useful for producing products such as peptides. In some embodiments, the present disclosure provides peptides comprising residues of provided amino acids.

8 Claims, No Drawings

(56) References Cited

FOREIGN PATENT DOCUMENTS

| | | | |
|---|---|---|---|
| WO | WO-2015/179635 | A2 | 11/2015 |
| WO | WO-2016/038104 | A1 | 3/2016 |
| WO | WO-2019/51327 | A2 | 3/2019 |
| WO | WO-2020/041270 | A1 | 2/2020 |
| WO | WO-2020/225095 | A1 | 11/2020 |
| WO | WO-2021/119537 | A1 | 6/2021 |
| WO | WO-2021/188659 | A1 | 9/2021 |
| WO | WO-2022/020652 | A2 | 1/2022 |
| WO | WO-2022/261257 | A1 | 12/2022 |

OTHER PUBLICATIONS

International Search Report for PCT/US2021/042854, 4 pages (mailed Dec. 23, 2021).

Morris, C. J. and Thompson, J. F., Conversion of m-Carboxyphenylalanine to m-Carboxyphenylglycine in Wedgewood Iris Leaves, Arch. Biochem. Biophys., 110:506-510 1965.

Pub Chem SID: 228881670, SCHEMBL2805656 (2015), <https://pubchem.ncbi.nlm.nih.gov/substance/228881670>. Retrieved on Oct. 12, 2021.

Schafmeister et al., An All-Hydrocarbon Cross-Linking System for Enhancing the Helicity and Metabolic Stability of Peptides, J. Am. Chem. Soc., 122: 5891-5892 (2000).

White, B. et al., Discovery and development of a Helicon(TM) inhibitor of the β-catenin/TCF interaction, Fog Pharma Poster, 1 page, (2022).

Written Opinion for PCT/US2021/042854, 7 pages (mailed Dec. 23, 2021).

Faust, J. and Schreiber, K., Synthese von Glycinanaloga des Nicotianamins, Journal f. prakt. Chemie. Band 330, Heft 6, 873-878 (1988).

Hatanaka, T. et al., Supporting Information For Convenient thioacid precursor, α-methylphenacyl thioester, Organic & Biomolecular Chemistry, pp. 1-110 (2016).

Hatanaka, T. et al., α-Methylphenacyl thioesters as convenient thioacid precursors, Organic & Biomolecular Chemistry, 14:10589-10592 (2016).

Hays, S. et al., New and Versatile Approaches to the Synthesis of CPP-Related Competitive NMDA Antagonists. Preliminary Structure-Activity Relationships and Pharmacological Evaluation, J. Med. Chem., 33:2916-2924 (1990).

Mindt, T. et al., "Click to Chelate": Synthesis and Installation of Metal Chelates into Biomolecules in a Single Step, J. Am. Chem. Soc., 128:15096-15097 (2006).

Scholz, G. et al., Structure-Function Relationships of Nicotianamine Analogues, Phytochemistry, 27(9):2749-2754 (1988).

AMINO ACIDS

CROSS-REFERENCE TO RELATED APPLICATIONS

This application claims priority to United States Provisional Application Nos. 63/055,301, filed Jul. 22, 2020, and 63/208,491, filed Jun. 8, 2021, the entirety of each of which is incorporated herein by reference.

BACKGROUND

Amino acids are useful for many purposes. For example, they can be utilized for the preparation of various biologically active small molecules and polymers, e.g., peptides.

SUMMARY

Many compounds, e.g., peptides, comprise amino acid residues. In many instances, natural amino acids, particularly those naturally encoded, are utilized for construction of such compounds. Natural amino acids, however, have a limited structural diversity. Among other things, the present disclosure recognizes that the low level of structural diversity of amino acids prior to the present disclosure may limit usefulness of products made therefrom, for example, due to less than optimal properties and/or activities (e.g., solubility, lipophilicity, target binding, etc.). In some embodiments, the present disclosure provides compounds, e.g., amino acids, that have novel structural features and can provide improved properties and/or activities to products made therefrom.

In some embodiments, the present disclosure provides compounds having the structure of formula PA:

$$N(R^{PA})(R^{a1})—L^{a1}-C(R^{a2})(R^{a3})-L^{a2}-C(O)R^{PC}, \quad \text{PA}$$

or a salt thereof, wherein each variable is independently as described herein.

Among other things, provided compounds are useful as amino acid building blocks for preparation of various products, including various peptides. In some embodiments, the present disclosure provides products, e.g., peptides, comprising residues of provided compounds, e.g., those of formula PA or salts thereof. In some embodiments, a provided compound may be utilized to replace an acidic amino acid residue (e.g., Asp, Glu) in a product, e.g., peptide, to improve one or more properties and/or activities. In some embodiments, compared to Asp and/or Glu, a provided compound can provide increased lipophilicity (e.g., as assessed by Log D) and/or modulated acidity (e.g., as assessed by pKa) without significantly impact other properties and/or activities (e.g., solubility, target binding, etc.). In some embodiments, products, e.g., peptides, comprising residues of provided compounds have increased lipophilicity and/or comparable solubility and/or target binding properties compared to reference products which have Asp and/or Glu instead of residues of provided compounds but are otherwise identical. In some embodiments, provided products can be more effectively delivered into cells.

DETAILED DESCRIPTION OF CERTAIN EMBODIMENTS

Definitions

As used herein, the following definitions shall apply unless otherwise indicated. For purposes of this disclosure, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation (but not aromatic), or combinations thereof. In some embodiments, aliphatic groups contain 1-50 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

Alkenyl: As used herein, the term "alkenyl" refers to an aliphatic group, as defined herein, having one or more double bonds.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Amino acid: In its broadest sense, as used herein, refers to any compound and/or substance that can be incorporated into a polypeptide chain, e.g., through formation of one or more peptide bonds. In some embodiments, an amino acid comprising an amino group and a carboxylic acid group. In some embodiments, an amino acid has the structure of $NH(R^{a1})$-$L^{a1}$-$C(R^{a2})(R^{a3})$-$L^{a2}$-COOH, wherein each variable is independently as described in the present disclosure. In some embodiments, an amino acid has the general structure $NH(R')—C(R')_2—COOH$, wherein each R' is independently as described in the present disclosure. In some embodiments, an amino acid has the general structure $H_2N—C(R')_2—COOH$, wherein R' is as described in the present disclosure. In some embodiments, an amino acid has the general structure $H_2N—C(H)(R')—COOH$, wherein R' is as described in the present disclosure. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. “Standard amino acid” refers to any of the twenty standard L-amino acids commonly found in naturally occurring peptides. “Nonstandard amino acid” refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, one or more hydrogens, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term “amino acid” may be used to refer to a free amino acid; in some embodiments it may be used to refer to an amino acid residue of a polypeptide.

Analog: As used herein, the term “analog” refers to a substance that shares one or more particular structural features, elements, components, or moieties with a reference substance. Typically, an “analog” shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Aryl: The term “aryl” used alone or as part of a larger moiety as in “aralkyl,” “aralkoxy,” “aryloxyalkyl,” etc. refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term “aryl” may be used interchangeably with the term “aryl ring.” In certain embodiments of the present disclosure, “aryl” refers to an aromatic ring system which includes, but not limited to, phenyl, biphenyl, naphthyl, binaphthyl, anthracyl and the like, which may bear one or more substituents. In some embodiments, also included within the scope of the term “aryl,” as it is used herein, is a group in which an aromatic ring is fused to one or more non-aromatic rings, such as indanyl, phthalimidyl, naphthimidyl, phenanthridinyl, or tetrahydronaphthyl, and the like, where a radical or point of attachment is on an aryl ring.

Cycloaliphatic: The term “cycloaliphatic,” as used herein, refers to saturated or partially unsaturated aliphatic monocyclic, bicyclic, or polycyclic ring systems having, e.g., from 3 to 30, members, wherein the aliphatic ring system is optionally substituted. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms “cycloaliphatic” may also include aliphatic rings that are fused to one or more aromatic or nonaromatic rings, such as decahydronaphthyl or tetrahydronaphthyl, where a radical or point of attachment is on an aliphatic ring. In some embodiments, a carbocyclic group is bicyclic. In some embodiments, a carbocyclic group is tricyclic. In some embodiments, a carbocyclic group is polycyclic. In some embodiments, “cycloaliphatic” (or “carbocycle” or “cycloalkyl”) refers to a monocyclic $C_3$-$C_6$ hydrocarbon, or a $C_8$-$C_{10}$ bicyclic hydrocarbon that is completely saturated or that contains one or more units of unsaturation, but which is not aromatic, or a $C_9$-$C_{16}$ tricyclic hydrocarbon that is completely saturated or that contains one or more units of unsaturation, but which is not aromatic.

Derivative: As used herein, the term “derivative” refers to a structural analogue of a reference substance. That is, a “derivative” is a substance that shows significant structural similarity with the reference substance, for example sharing a core or consensus structure, but also differs in certain discrete ways. In some embodiments, a derivative is a substance that can be generated from the reference substance by chemical manipulation. In some embodiments, a derivative is a substance that can be generated through performance of a synthetic process substantially similar to (e.g., sharing a plurality of steps with) one that generates the reference substance.

Halogen: The term “halogen” means F, Cl, Br, or I.

Heteroaliphatic: The term “heteroaliphatic” is given its ordinary meaning in the art and refers to aliphatic groups as described herein in which one or more carbon atoms are replaced with one or more heteroatoms (e.g., oxygen, nitrogen, sulfur, silicon, phosphorus, and the like).

Heteroalkyl: The term “heteroalkyl” is given its ordinary meaning in the art and refers to alkyl groups as described herein in which one or more carbon atoms is replaced with a heteroatom (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms “heteroaryl” and “heteroar-,” used alone or as part of a larger moiety, e.g., “heteroaralkyl,” or “heteroaralkoxy,” refer to monocyclic, bicyclic or polycyclic ring systems having, for example, a total of five to thirty, e.g., 5, 6, 9, 10, 14, etc., ring members, wherein at least one ring in the system is aromatic and at least one aromatic ring atom is a heteroatom. In some embodiments, a heteroatom is nitrogen, oxygen or sulfur. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where a radical or point of attachment is on a heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom" means an atom that is not carbon and is not hydrogen. In some embodiments, a heteroatom is oxygen, sulfur, nitrogen, phosphorus, boron or silicon (including any oxidized form of nitrogen, sulfur, phosphorus, or silicon; the quaternized form of any basic nitrogen or a substitutable nitrogen of a heterocyclic ring (for example, N as in 3,4-dihydro-2H-pyrrolyl), NH (as in pyrrolidinyl) or $NR^+$ (as in N-substituted pyrrolidinyl); etc.). In some embodiments, a heteroatom is boron, nitrogen, oxygen, silicon, sulfur, or phosphorus. In some embodiments, a heteroatom is nitrogen, oxygen, silicon, sulfur, or phosphorus. In some embodiments, a heteroatom is nitrogen, oxygen, sulfur, or phosphorus. In some embodiments, a heteroatom is nitrogen, oxygen or sulfur.

Heterocyclyl: As used herein, the terms "heterocycle," "heterocyclyl," "heterocyclic radical," and "heterocyclic ring" are used interchangeably and refer to a monocyclic, bicyclic or polycyclic ring moiety (e.g., 3-30 membered) that is saturated or partially unsaturated and has one or more heteroatom ring atoms. In some embodiments, a heteroatom is boron, nitrogen, oxygen, silicon, sulfur, or phosphorus. In some embodiments, a heteroatom is nitrogen, oxygen, silicon, sulfur, or phosphorus. In some embodiments, a heteroatom is nitrogen, oxygen, sulfur, or phosphorus. In some embodiments, a heteroatom is nitrogen, oxygen or sulfur. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where a radical or point of attachment is on a heteroaliphatic ring. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95% or 99% identical. In some embodiments, polymeric molecules are considered to be "homologous" to one another if their sequences are at least 25%, 30%, 35% 40%, 45% 50%, 55% 60%, 65%, 70%, 75% 80%, 85%, 90%, 95% or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below (hydrophobicity scale of Kyte and Doolittle, 1982: A simple method for displaying the hydropathic character of a protein. J. Mol. Biol. 157:105-132):

| Amino Acid | 3 Letter Code | 1 Letter Code | Side Chain Polarity | Side Chain Acidity/ Basicity | Hydropathy Index of Kyte and Doolittle |
|---|---|---|---|---|---|
| Alanine | Ala | A | nonpolar | neutral | 1.8 |
| Arginine | Arg | R | polar | basic | −4.5 |
| Asparagine | Asn | N | polar | neutral | −3.5 |
| Aspartic acid | Asp | D | polar | acidic | −3.5 |
| Cysteine | Cys | C | nonpolar | neutral | 2.5 |
| Glutamic acid | Glu | E | polar | acidic | −3.5 |
| Glutamine | Gln | Q | polar | neutral | −3.5 |
| Glycine | Gly | G | nonpolar | neutral | −0.4 |
| Histidine | His | H | polar | basic | −3.2 |
| Isoleucine | Ile | I | nonpolar | neutral | 4.5 |
| Leucine | Leu | L | nonpolar | neutral | 3.8 |
| Lysine | Lys | K | polar | basic | −3.9 |
| Methionine | Met | M | nonpolar | neutral | 1.9 |
| Phenyl-alanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

-continued

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

Partially unsaturated: As used herein, the term "partially unsaturated" refers to a moiety that includes at least one double or triple bond. The term "partially unsaturated" is intended to encompass groups having multiple sites of unsaturation, but is not intended to include aryl or heteroaryl moieties.

Peptide: The term "peptide" as used herein refers to a polypeptide. In some embodiments, a peptide is a polypeptide that is relatively short, for example having a length of less than about 100 amino acids, less than about 50 amino acids, less than about 40 amino acids less than about 30 amino acids, less than about 25 amino acids, less than about 20 amino acids, less than about 15 amino acids, or less than 10 amino acids.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; RingeR's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known. For example, S. M. Berge, et al. describes pharmaceutically acceptable salts in detail in J. Pharmaceutical Sciences, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other known methods such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, pharmaceutically acceptable salts include, but are not limited to, nontoxic base addition salts, such as those formed by acidic groups of provided compounds with bases. Representative alkali or alkaline earth metal salts include salts of sodium, lithium, potassium, calcium, magnesium, and the like. In some embodiments, pharmaceutically acceptable salts are ammonium salts (e.g., $—N(R)_3+$). In some embodiments, pharmaceutically acceptable salts are sodium salts. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Polypeptide: As used herein refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a relevant polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Protecting group: The term "protecting group," as used herein, is well known in the art and includes those described in detail in Protecting Groups in Organic Synthesis, T. W. Greene and P. G. M. Wuts, 3$^{rd}$ edition, John Wiley & Sons, 1999, the entirety of which is incorporated herein by reference. Also included are those protecting groups specially adapted for nucleoside and nucleotide chemistry described in Current Protocols in Nucleic Acid Chemistry, edited by Serge L. Beaucage et al. June 2012, the entirety of Chapter 2 is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2, 5-dimethylpyrrole, N-1,1,4,4-tetramethyldisilylazacyclopentane adduct (STABASE), 5-substituted 1,3-dimethyl-1, 3,5-triazacyclohexan-2-one, 5-substituted 1,3-dibenzyl-1,3, 5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[ phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

In some embodiments, suitable mono-protected amines include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. In some embodiments, suitable di-protected amines include amines that are substituted with two substituents independently selected from those described above as mono-protected amines, and further include cyclic imides, such as phthalimide, maleimide, succinimide, and the like. In some embodiments, suitable di-protected amines include pyrroles and the like, 2,2,5,5-tetramethyl-[1,2,5]azadisilolidine and the like, and azide.

Suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl. In some embodiments, suitable protected carboxylic acids include, but are not limited to, optionally substituted $C_{1-6}$ aliphatic esters, optionally substituted aryl esters, silyl esters, activated esters, amides, hydrazides, and the like.

Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, a-methoxybenzylidene ortho ester, 1-(N,N-dimethylamino)ethylidene derivative, a-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In some embodiments, a hydroxyl protecting group is acetyl, t-butyl, tbutoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifiuoroacetyl, pivaloyl, 9-fluorenylmethyl carbonate, mesylate, tosylate, triflate, trityl, monomethoxytrityl (MMTr), 4,4'-dimethoxytrityl, (DMTr) and 4,4',4"-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenylsulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4" -tris(benzoyloxy)trityl, diphenylcarbamoyl, levulinyl, 2-(dibromomethyl)benzoyl (Dbmb), 2-(isopropylthiomethoxymethyl)benzoyl (Ptmt), 9-phenylxanthen-9-yl (pixyl) or 9-(p-methoxyphenyl)xanthine-9-yl (MOX). In some embodiments, each of the hydroxyl protecting groups is, independently selected from acetyl, benzyl, t-butyldimethylsilyl, t-butyldiphenylsilyl and 4,4'-dimethoxytrityl. In some embodiments, the hydroxyl protecting group is selected from the group consisting of trityl, monomethoxytrityl and 4,4'-dimethoxytrityl group. In some embodiments, a phosphorous linkage protecting group is a group attached to the phosphorous linkage (e.g., an internucleotidic linkage) throughout oligonucleotide synthesis. In some embodiments, a protecting group is attached to a sulfur atom of an phosphorothioate group. In some embodiments, a protecting group is attached to an oxygen atom of an internucleotide phosphorothioate linkage. In some embodiments, a protecting group is attached to an oxygen atom of the internucleotide phosphate linkage. In some embodiments a protecting group is 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1-butyl, 2-cyano-1,1-dimethylethyl, 4-N-methylaminobutyl, 3-(2-pyridyl)-1-propyl, 2-[N-methyl-N-(2-pyridyl)]aminoethyl, 2-(N-formyl,N-methyl)aminoethyl, or 4-[N-methyl-N-(2,2,2-trifluoroacetyl)amino]butyl.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Substitution: As described herein, compounds of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. In some embodiments, example substituents are described below.

Suitable monovalent substituents are halogen; $-(CH_2)_{0-4}R^{\circ}$; $-(CH_2)_{0-4}OR^{\circ}$; $-O(CH_2)_{0-4}R^{\circ}$, $-O-(CH_2)_{0-4}C(O)OR^{\circ}$; $-(CH_2)_{0-4}CH(OR^{\circ})_2$; $-(CH_2)_{0-4}Ph$, which may be substituted with $R^{\circ}$; $-(CH_2)_{0-4}O(CH_2)_{0-1}Ph$ which may be substituted with $R^{\circ}$; $-CH{=}CHPh$, which may be substituted with $R^{\circ}$; $-(CH_2)_{0-4}O(CH_2)_{0-1}$-pyridyl which may be substituted with $R^{\circ}$; $-NO_2$; $-CN$; $-N_3$; $-(CH_2)_{0-4}N(R^{\circ})_2$; $-(CH_2)_{0-4}N(R^{\circ})C(O)R^{\circ}$; $-N(R^{\circ})C(S)R^{\circ}$; $-(CH_2)_{0-4}N(R^{\circ})C(O)N(R^{\circ})_2$; $-N(R^{\circ})C(S)N(R^{\circ})_2$; $-(CH_2)_{0-4}N(R^{\circ})C(O)OR^{\circ}$; $-N(R^{\circ})N(R^{\circ})C(O)R^{\circ}$; $-N(R^{\circ})N(R^{\circ})C(O)N(R^{\circ})_2$; $-N(R^{\circ})N(R^{\circ})C(O)OR^{\circ}$; $-(CH_2)_{0-4}C(O)R^{\circ}$; $-C(S)R^{\circ}$; $-(CH_2)_{0-4}C(O)OR^{\circ}$; $-(CH_2)_{0-4}C(O)SR^{\circ}$; $-(CH_2)_{0-4}C(O)OSi(R^{\circ})_3$; $-(CH_2)_{0-4}OC(O)R^{\circ}$; $-OC(O)(CH_2)_{0-4}SR^{\circ}$, $-SC(S)SR^{\circ}$; $-(CH_2)_{0-4}SC(O)R^{\circ}$; $-(CH_2)_{0-4}C(O)N(R^{\circ})_2$; $-C(S)N(R^{\circ})_2$; $-C(S)SR^{\circ}$; $-SC(S)SR^{\circ}$, $-(CH_2)_{0-4}OC(O)N(R^{\circ})_2$; $-C(O)N(OR^{\circ})R^{\circ}$; $-C(O)C(O)R^{\circ}$; $-C(O)CH_2C(O)R^{\circ}$; $-C(NOR^{\circ})R^{\circ}$; $-(CH_2)_{0-4}SSR^{\circ}$; $-(CH_2)_{0-4}S(O)_2R^{\circ}$; $-(CH_2)_{0-4}S(O)_2OR^{\circ}$; $-(CH_2)_{0-4}OS(O)_2R^{\circ}$; $-S(O)_2N(R^{\circ})_2$; $-(CH_2)_{0-4}S(O)R^{\circ}$; $-N(R^{\circ})S(O)_2N(R^{\circ})_2$; $-N(R^{\circ})S(O)_2R^{\circ}$; $-N(OR^{\circ})R^{\circ}$; $-C(NH)N(R^{\circ})_2$; $-Si(R^{\circ})_3$; $-OSi(R^{\circ})_3$; $-P(R^{\circ})_2$; $-P(OR^{\circ})_2$; $-OP(R^{\circ})_2$; $-OP(OR^{\circ})_2$; $-N(R^{\circ})P(R^{\circ})_2$; $-B(R^{\circ})_2$; $-OB(R^{\circ})_2$; $-P(O)(R^{\circ})_2$; $-OP(O)(R^{\circ})_2$; $-N(R^{\circ})P(O)(R^{\circ})_2$; $-(C_{1-4}$ straight or branched alkylene)$O-N(R^{\circ})_2$; or $-(C_{1-4}$ straight or branched alkylene)$C(O)O-N(R^{\circ})_2$; wherein each $R^{\circ}$ may be substituted as defined below and is independently hydrogen, $C_{1-20}$ aliphatic, $C_{1-20}$ heteroaliphatic having 1-5 heteroatoms independently selected from nitrogen, oxygen, sulfur, silicon and phosphorus, $-CH_2-(C_{6-14}$ aryl), $-O(CH_2)_{0-1}(C_{6-14}$ aryl), $-CH_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of $R^{\circ}$, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on $R^{\circ}$ (or the ring formed by taking two independent occurrences of $R^{\circ}$ together with their intervening atoms), are independently halogen, $-(CH_2)_{0-2}R^{\bullet}$, -(halo$R^{\bullet}$), $-(CH_2)_{0-2}OH$, $-(CH_2)_{0-2}OR^{\bullet}$, $-(CH_2)_{0-2}CH(OR^{\bullet})_2$; $-O$(halo$R^{\bullet}$), $-CN$, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR^{\bullet}_2$, $-NO_2$, $-SiR^{\bullet}_3$, $-OSiR^{\bullet}_3$, $-C(O)SR^{\bullet}$, $-(C_{1-4}$ straight or branched alkylene)$C(O)OR^{\bullet}$, or $-SSR^{\bullet}$ wherein each $R^{\bullet}$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of $R^{\circ}$ include $=O$ and $=S$.

Suitable divalent substituents are the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of $R^*$ are halogen, $-R^{\bullet}$, -(halo$R^{\bullet}$), $-OH$, $-OR^{\bullet}$, $-O$(halo$R^{\bullet}$), $-CN$, $-C(O)OH$, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur.

In some embodiments, suitable substituents on a substitutable nitrogen are $-R^{\dagger}$, $-NR^{\dagger}_2$, $-C(O)R^{\dagger}$, $-C(O)OR^{\dagger}$, $-C(O)C(O)R^{\dagger}$, $-C(O)CH_2C(O)R^{\dagger}$, $-S(O)_2R^{\dagger}$, $-S(O)_2NR^{\dagger}_2$, $-C(S)NR^{\dagger}_2$, $-C(NH)NR^{\dagger}_2$, or $-N(R^{\dagger})S(O)_2R^{\dagger}$; wherein each $R^{\dagger}$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, and sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of $R^{\dagger}$ are independently halogen, —$R^{\bullet}$, -(halo$R^{\bullet}$), —OH, —$OR^{\bullet}$, —O(halo$R^{\bullet}$), —CN, —C(O)OH, —C(O)$OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

Unsaturated: The term "unsaturated" as used herein, means that a moiety has one or more units of unsaturation.

Unless otherwise specified, salts, such as pharmaceutically acceptable acid or base addition salts, stereoisomeric forms, and tautomeric forms, of provided compound are included.

As used herein in the present disclosure, unless otherwise clear from context, (i) the term "a" or "an" may be understood to mean "at least one"; (ii) the term "or" may be understood to mean "and/or"; (iii) the terms "comprising", "comprise", "including" (whether used with "not limited to" or not), and "include" (whether used with "not limited to" or not) may be understood to encompass itemized components or steps whether presented by themselves or together with one or more additional components or steps; (iv) the term "another" may be understood to mean at least an additional/second one or more; (v) the terms "about" and "approximately" may be understood to permit standard variation as would be understood by those of ordinary skill in the art; and (vi) where ranges are provided, endpoints are included.

Certain Embodiments of Provided Compounds

In some embodiments, the present disclosure provides various compounds, which among other things may be utilized as amino acids for a number of applications, e.g., for preparation of peptides or other useful compounds.

In some embodiments, a provided compound or a salt thereof comprises 1) a first group which is an optionally protected amino group, 2) a second group which is an optionally protected and/or activated carboxyl group, and 3) a side chain (typically bonded to an atom between the first and second groups ("a side chain attachment atom")) which comprises an optionally protected and/or activated carboxyl group and a) an optionally substituted ring (which ring is typically between the optionally protected and/or activated carboxyl group of the side chain and a side chain attachment atom) or b) an amino group (which amino group is typically between the optionally protected and/or activated carboxyl group of the side chain and a side chain attachment atom). In some embodiments, a provided compound is an optionally protected and/or activated amino acid or a salt thereof, wherein the side chain of the amino acid comprises an optionally protected and/or activated carboxyl group, and an optionally substituted ring or an amino group, wherein the optionally substituted ring or an amino group is between the optionally protected and/or activated carboxyl group and a backbone atom to which a side chain is attached (e.g., an atom between an amino and carboxyl group, both of which can be optionally and independently protected and/or activated (e.g., an alpha carbon atom in an amino acid)).

In some embodiments, the present disclosure provides compounds having the structure of formula PA:

$$N(R^{PA})(R^{a1})—L^{a1}—C(R^{a2})(R^{a3})—L^{a2}—C(O)R^{PC}, \quad \text{PA}$$

or a salt thereof, wherein:

$R^{PA}$ is —H or an amino protecting group;

each of $R^{a1}$ and $R^{a3}$ is independently -$L^a$-R';

$R^{a2}$ is -$L^{aa}$-C(O)$R^{PS}$;

each of $L^a$, $L^{a1}$ and $L^{a2}$ is independently L;

—C(O)$R^{PS}$ is optionally protected or activated —COOH;

—C(O)$R^{PC}$ is optionally protected or activated —COOH;

each L is independently a covalent bond, or an optionally substituted, bivalent $C_1$-$C_{25}$ aliphatic or heteroaliphatic group having 1-10 heteroatoms wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—;

each -Cy- is independently an optionally substituted bivalent, 3-30 membered, monocyclic, bicyclic or polycyclic ring having 0-10 heteroatoms;

each R' is independently —R, —C(O)R, —$CO_2R$, or —$SO_2R$; and each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

In some embodiments, the present disclosure provides compounds having the structure of formula PA:

$$N(R^{PA})(R^{a1})—L^{a1}—C(R^{a2})(R^{a3})—L^{a2}—C(O)R^{PC}, \quad \text{PA}$$

or a salt thereof, wherein:

$R^{PA}$ is —H or an amino protecting group;

each of $R^{a1}$ and $R^{a3}$ is independently -$L^a$-R';

$R^{a2}$ is -$L^{aa}$-C(O)$R^{PS}$, wherein $L^{aa}$ is L and $L^{aa}$ comprises —N(R')— or -Cy-;

each of $L^a$, $L^{a1}$ and $L^{a2}$ is independently L;

—C(O)$R^{PS}$ is optionally protected or activated —COOH;

—C(O)$R^{PC}$ is optionally protected or activated —COOH;

each L is independently a covalent bond, or an optionally substituted, bivalent $C_1$-$C_{25}$ aliphatic or heteroaliphatic group having 1-10 heteroatoms wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;

each -Cy- is independently an optionally substituted bivalent, 3-30 membered, monocyclic, bicyclic or polycyclic ring having 0-10 heteroatoms;

each R' is independently —R, —C(O)R, —CO$_2$R, or —SO$_2$R; and each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or.

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

In some embodiments, $L^{a1}$ is a covalent bond. In some embodiments, $L^{a1}$ is not a covalent bond. In some embodiments, $L^{a1}$ is an optionally substituted, bivalent $C_1$-$C_{25}$ aliphatic group wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, $L^{a1}$ is an optionally substituted, bivalent $C_1$-$C_{10}$ aliphatic group wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, $L^{a1}$ is an optionally substituted, bivalent $C_1$-$C_6$ aliphatic group wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, $L^{a1}$ is an optionally substituted, bivalent $C_1$-$C_6$ aliphatic group wherein one or more methylene units of the group are optionally and independently replaced with -Cy-, —O—, —S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, $L^{a1}$ is an optionally substituted, bivalent $C_1$-$C_6$ aliphatic group wherein one or more methylene units of the group are optionally and independently replaced with -Cy-, —O—, —S—, —N(R')—, —C(O)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, $L^{a1}$ is an optionally substituted, bivalent $C_1$-$C_6$ aliphatic group wherein one or more methylene units of the group are optionally and independently replaced with -Cy-, —O—, —S—, —N(R')—, —C(O)—, —C(O)N(R')—, —N(R')C(O)N(R')—, —N(R')C(O)O—, or —C(O)O—. In some embodiments, $L^{a1}$ is an optionally substituted, bivalent $C_1$-$C_6$ aliphatic group wherein one or more methylene units of the group are optionally and independently replaced with —O—, —S—, —N(R')—, —C(O)—, —C(O)N(R')—, —N(R')C(O)N(R')—, —N(R')C(O)O—, or —C(O)O—.

In some embodiments, $L^{a2}$ is a covalent bond. In some embodiments, $L^{a2}$ is not a covalent bond. In some embodiments, $L^{a2}$ is an optionally substituted, bivalent $C_1$-$C_{25}$ aliphatic group wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, $L^{a2}$ is an optionally substituted, bivalent $C_1$-$C_{10}$ aliphatic group wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, $L^{a2}$ is an optionally substituted, bivalent $C_1$-$C_6$ aliphatic group wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, $L^{a2}$ is an optionally substituted, bivalent $C_1$-$C_6$ aliphatic group wherein one or more methylene units of the group are optionally and independently replaced with -Cy-, —O—, —S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, $L^{a2}$ is an optionally substituted, bivalent $C_1$-$C_6$ aliphatic group wherein one or more methylene units of the group are optionally and independently replaced with -Cy-, —O—, —S—, —N(R')—, —C(O)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, $L^{a2}$ is an optionally substituted, bivalent $C_1$-$C_6$ aliphatic group wherein one or more methylene units of the group are optionally and independently replaced with -Cy-, —O—, —S—, —N(R')—, —C(O)—, —C(O)N(R')—, —N(R')C(O)N(R')—, —N(R')C(O)O—, or —C(O)O—. In some embodiments, $L^{a2}$ is an optionally substituted, bivalent $C_1$-$C_6$ aliphatic group wherein one or more methylene units of the group are optionally and independently replaced with —O—, —S—, —N(R')—, —C(O)—, —C(O)N(R')—, —N(R')C(O)N(R')—, —N(R')C(O)O—, or —C(O)O—.

In some embodiments, $R^{a2}$ is -$L^{aa}$-C(O)$R^{PS}$, wherein $L^{aa}$ is an optionally substituted, bivalent $C_1$-$C_{25}$ aliphatic or heteroaliphatic group having 1-10 heteroatoms wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—, wherein at least one methylene unit is replaced with -Cy-. In some embodiments, $L^{aa}$ is an optionally substituted, bivalent $C_1$-$C_{10}$ aliphatic or heteroaliphatic group having 1-10 heteroatoms wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—, wherein at least one methylene unit is replaced with -Cy-.

As used herein, in some embodiments, -Cy- is an optionally substituted bivalent 3-10 (e.g., 3, 4, 5, 6, 7, 8, 9, or 10) membered monocyclic cycloaliphatic group. In some embodiments, -Cy- is an optionally substituted 3-10 (e.g., 3, 4, 5, 6, 7, 8, 9, or 10) membered monocyclic cycloalkyl ring. In some embodiments, -Cy- is an optionally substituted 3-10 (e.g., 3, 4, 5, 6, 7, 8, 9, or 10) membered monocyclic heteroaliphatic ring having 1-5 heteroatoms. In some embodiments, -Cy- is an optionally substituted 3-10 (e.g., 3, 4, 5, 6, 7, 8, 9, or 10) membered monocyclic heteroalkyl ring having 1-5 heteroatoms. In some embodiments, -Cy- is an optionally substituted bivalent 5-15 (e.g., 5, 6, 7, 8, 9, 10, 11, 12, 13, 14, or 15) membered bicyclic or polycyclic cycloaliphatic group. In some embodiments, -Cy- is an optionally substituted bivalent 5-15 (e.g., 5, 6, 7, 8, 9, 10, 11, 12, 13, 14, or 15) membered bicyclic or polycyclic cycloalkyl group. In some embodiments, -Cy- is an optionally substituted 5-15 (e.g., 5, 6, 7, 8, 9, 10, 11, 12, 13, 14, or 15) membered bicyclic or polycyclic heteroaliphatic ring having 1-5 heteroatoms. In some embodiments, -Cy- is an optionally substituted 5-15 (e.g., 5, 6, 7, 8, 9, 10, 11, 12, 13, 14, or 15) membered bicyclic or polycyclic heterocyclyl ring having 1-5 heteroatoms. In some embodiments, a cycloaliphatic, cycloalkyl, heteroaliphatic or heteroalkyl ring is 3-membered. In some embodiments, it is 4-membered. In some embodiments, it is 5-membered. In some embodiments, it is 6-membered. In some embodiments, it is 7-membered. In some embodiments, it is 8-membered. In some embodiments, it is 9-membered. In some embodiments, it is 10-membered. In some embodiments, it is 11-membered. In some embodiments, it is 12-membered. In some embodiments, -Cy- is optionally substituted phenylene. In some embodiments, -Cy- is an optionally substituted bivalent 10-membered bicyclic aryl ring. In some embodiments, -Cy- is an optionally substituted 5-membered heteroaryl ring having 1-4 heteroatoms. In some embodiments, -Cy- is an optionally substituted 6-membered heteroaryl ring having 1-4 heteroatoms. In some embodiments, -Cy- is an optionally substituted 9-membered bicyclic heteroaryl ring having 1-5 heteroatoms. In some embodiments, -Cy- is an optionally substituted 10-membered bicyclic heteroaryl ring having 1-5 heteroatoms. In some embodiments, a heteroaliphatic, heterocyclyl or heteroaryl ring contains no more than 1 heteroatom. In some embodiments, each heteroatom is independently selected from nitrogen, oxygen and sulfur.

In some embodiments, -Cy- is an optionally substituted 4-7 membered ring having 0-3 heteroatoms. In some embodiments, -Cy- is an optionally substituted 6-membered aryl ring. In some embodiments, an aryl ring is substituted. In some embodiments, it is substituted with one or more halogen. In some embodiments, it is substituted with one or more —F. In some embodiments, it is not substituted. In some embodiments, it is optionally substituted

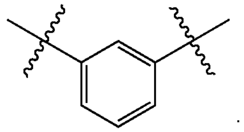 [SMILES: *c1cccc(*)c1]

In some embodiments, it is

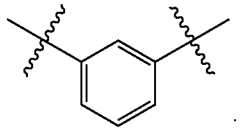 [SMILES: *c1cccc(*)c1]

In some embodiments, it is optionally substituted

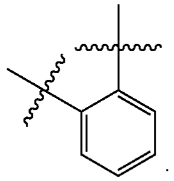 [SMILES: *c1ccccc1*]

In some embodiments, it is

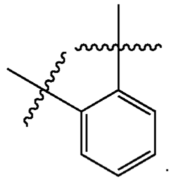 [SMILES: *c1ccccc1*]

In some embodiments, it is optionally substituted

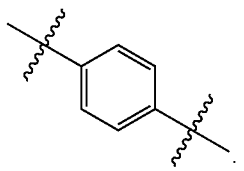 [SMILES: *c1ccc(*)cc1]

In some embodiments, it is

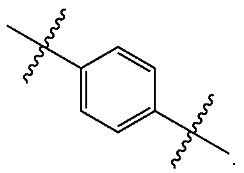 [SMILES: *c1ccc(*)cc1]

In some embodiments, -Cy- is an optionally substituted 5-membered heteroaryl ring having 1-3 heteroatoms. In some embodiments, a heteroatom is nitrogen. In some embodiments, a heteroatom is oxygen. In some embodiments, a heteroatom is sulfur. In some embodiments, -Cy- is optionally substituted

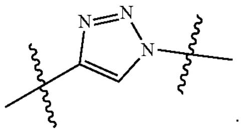 [SMILES: *c1cn(*)nn1]

In some embodiments, -Cy- is

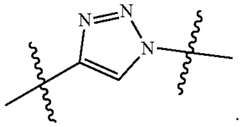 [SMILES: *c1cn(*)nn1]

In some embodiments, $L^{aa}$ is $-L^{am1}$-Cy-$L^{am2}$, wherein each of $L^{am1}$ and $L^{am2}$ is independently $L^{am}$, wherein each $L^{am}$ is independently a covalent bond, or an optionally substituted, bivalent $C_1$-$C_{10}$ aliphatic group wherein one or more methylene units of the aliphatic group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—.

In some embodiments, $L^{aa}$ comprises -Cy-. In some embodiments, $L^{aa}$ is $-L^{am1}$-Cy-$L^{am2}$- wherein each of $L^{am1}$ and $L^{am2}$ is independently $L^{am}$, wherein each $L^{am}$ is independently a covalent bond, or an optionally substituted, bivalent $C_1$-$C_{10}$ aliphatic group wherein one or more methylene units of the aliphatic group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments, $-L^{am2}$- is bonded to —$C(O)R^{PS}$. In some embodiments, $L^{am2}$ is a covalent bond.

In some embodiments, -Cy- is an optionally substituted 4-7 membered ring having 0-3 heteroatoms. In some embodiments, -Cy- is an optionally substituted 5-7 membered ring having 0-3 heteroatoms. In some embodiments, -Cy- is an optionally substituted 6-7 membered ring having 0-3 heteroatoms. In some embodiments, -Cy- is an optionally substituted 4-membered ring having 0-1 heteroatoms. In some embodiments, -Cy- is an optionally substituted 5-membered ring having 0-2 heteroatoms. In some embodiments, -Cy- is an optionally substituted 6-membered ring having 0-2 heteroatoms. In some embodiments, -Cy- is an optionally substituted 7-membered ring having 0-3 heteroatoms.

In some embodiments, $R^{a2}$ is $-L^{aa}$-$C(O)R^{PS}$, wherein $L^{aa}$ is an optionally substituted, bivalent $C_1$-$C_{25}$ aliphatic or heteroaliphatic group having 1-10 heteroatoms wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—, wherein at least one methylene unit is replaced with —N(R')—.

In some embodiments, $L^{aa}$ comprises —N(R')—. In some embodiments, $L^{aa}$ is $-L^{am1}$-(NR')-$L^{am2}$-, wherein each of $L^{am1}$ and $L^{am2}$ is independently $L^{am}$, wherein each $L^{am}$ is independently a covalent bond, or an optionally substituted, bivalent $C_1$-$C_{10}$ aliphatic group wherein one or more methylene units of the aliphatic group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments, $-L^{am2}$- is bonded to —$C(O)R^{PS}$. In some embodiments, $L^{am1}$ is optionally substituted $C_{1-4}$ alkylene. In some embodiments, $L^{am1}$ is optionally substituted —$(CH_2)m$-, wherein m is 1, 2, 3, or 4. In some embodiments, $L^{am1}$ is —$CH_2$—. In some embodiments, $L^{am2}$ is optionally substituted linear $C_{1-2}$ alkylene. In some embodiments, $L^{am2}$ is —$[C(R')_2]n$, wherein n is 1 or 2. In some embodiments, $L^{am2}$ is —[CHR']n, wherein n is 1 or 2. In some embodiments, each R' is independently —H or optionally substituted $C_{1-6}$ alkyl. In some embodiments, $L^{am2}$ is optionally substituted —$CH_2$—. In some embodiments, $L^{am2}$ is —$CH_2$—. In some embodiments, R' is —$R^{NR}$, wherein $R^{NR}$ is R. In some embodiments, R' is —$CH_2$—$R^{NR}$, wherein $R^{NR}$ is R. In some embodiments, R' of the —N(R')— is —$C(O)R^{NR}$, wherein $R^{NR}$ is R. In some embodiments, R' of the —N(R')— is —$SO_2R^{NR}$, wherein $R^{NR}$ is R. In some embodiments, R is optionally substituted $C_{1-6}$ aliphatic or heteroaliphatic having 1-4 heteroatoms. In some embodiments, R is $C_{1-7}$ alkyl or heteroalkyl having 1-4 heteroatoms optionally substituted with one or more groups independently selected from halogen, a $C_{5-6}$ aromatic ring having 0-4 heteroatoms, and an optionally substituted 3-10 membered cycloalkyl or heteroalkyl ring having 1-4 heteroatoms. In some embodiments, R is —$CF_3$. In some embodiments, $L^{am2}$ is or comprises —$C(R')_2$— wherein the R' group and R' in —N(R')— are taken together with their intervening atoms to form an optionally substituted, 3-30 membered, monocyclic, bicyclic or polycyclic ring having, in addition to the intervening atoms, 0-10 heteroatoms.

In some embodiments, $L^{aa}$ is $-L^{am1}$-N(R')-$L^{am2}$-, wherein each of $L^{am1}$ and $L^{am2}$ is independently $L^{am}$, wherein each $L^{am}$ is independently a covalent bond, or an optionally substituted, bivalent $C_1$-$C_{10}$ aliphatic group wherein one or more methylene units of the aliphatic group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—.

In some embodiments, —N(R')— is bonded to two carbon atoms which two carbon atoms do not form any double bonds with heteroatoms. In some embodiments, —N(R')— is bonded to two sp3 atoms. In some embodiments, —N(R')— is bonded to two sp3 carbon atoms. In some embodiments, —N(R')— is bonded to two —$CH_2$—, each of which is independently and optionally substituted with one or two monovalent substituent. In some embodiments, —N(R')— is bonded to two —$CH_2$—.

In some embodiments, $L^{aa}$ comprises —N(R')—. In some embodiments, R' of the —N(R')— is —$R^{NR}$, wherein $R^{NR}$ is R. In some embodiments, R' of the —N(R')— is —$CH_2$—$R^{NR}$, wherein $R^{NR}$ is R, and the —$CH_2$— is optionally substituted. In some embodiments, R' of the —N(R')— is —$C(O)R^{NR}$, wherein $R^{NR}$ is R. In some embodiments, R' of the —N(R')— is —$SO_2R^{NR}$, wherein $R^{NR}$ is R. In some embodiments, —N(R')— is —N(Et)-. In some embodiments, —N(R')— is —$N(CH_2CF_3)$—. In some embodiments, R' is optionally substituted $C_{1-6}$ aliphatic or heteroaliphatic having 1-4 heteroatoms. In some embodiments, R' is $C_{1-7}$ alkyl or heteroalkyl having 1-4 heteroatoms, wherein the alkyl or heteroalkyl is optionally substituted with one or more groups independently selected from halogen, a $C_{5-6}$ aromatic ring having 0-4 heteroatoms, and an optionally substituted 3-10 membered cycloalkyl or heteroalkyl ring having 1-4 heteroatoms. In some embodiments, R is —$CF_3$.

In some embodiments, R' of —N(R')— is R, $R^{a3}$ is R, and the two R groups are taken together with their intervening atoms to form an optionally substituted 3-10 membered ring having 0-5 heteroatoms in addition to the intervening atoms. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is monocyclic. In some embodiments, a formed ring is bicyclic or polycyclic. In some embodiments, a formed ring is saturated. In some embodiments, a formed ring is partially unsaturated.

In some embodiments, $L^{am1}$ is a covalent bond. In some embodiments, $L^{am1}$ is not a covalent bond. In some embodiments, $L^{am1}$ is optionally substituted $C_{1-4}$ alkylene. In some embodiments, $L^{am1}$ is optionally substituted —$(CH_2)$m-, wherein m is 1, 2, 3, or 4. In some embodiments, $L^{am1}$ is optionally substituted —$CH_2$—. In some embodiments, $L^{am1}$ is —$CH_2$—.

In some embodiments, $L^{am2}$ is bonded to —C(O)$R^{PS}$.

In some embodiments, $L^{am2}$ is a covalent bond. In some embodiments, $L^{am2}$ is a covalent bond when it is between -Cy- and —C(O)$R^{PS}$. In some embodiments, $L^{am2}$ is not a covalent bond. In some embodiments, $L^{am2}$ is optionally substituted $C_{1-4}$ alkylene. In some embodiments, $L^{am2}$ is optionally substituted —$(CH_2)$m-, wherein m is 1, 2, 3, or 4. In some embodiments, $L^{am2}$ is optionally substituted linear $C_{1-2}$ alkylene. In some embodiments, $L^{am2}$ is —$[C(R')_2]$n, wherein n is 1 or 2. In some embodiments, $L^{am2}$ is —[CHR'] n, wherein n is 1 or 2. In some embodiments, each R' is independently —H or optionally substituted $C_{1-6}$ alkyl. In some embodiments, $L^{am2}$ is optionally substituted —$CH_2$—. In some embodiments, $L^{am2}$ is —$CH_2$—. In some embodiments, $L^{am2}$ is optionally substituted —$CH_2$—$CH_2$—. In some embodiments, $L^{am2}$ is —$CH_2$—$C(CH_3)_2$—.

In some embodiments, $L^{am2}$ is or comprises —$C(R')_2$— wherein the R' group and R' in —N(R')— of $L^{aa}$ are taken together with their intervening atoms to form an optionally substituted, 3-30 membered, monocyclic, bicyclic or polycyclic ring having, in addition to the intervening atoms, 0-10 heteroatoms.

In some embodiments, $R^{a2}$ is -$L^{aa}$-C(O)$R^{PS}$, wherein $L^{aa}$ is L as described herein. In some embodiments, $L^{aa}$ is $L^{am2}$ as described herein. In some embodiments, $L^{aa}$ is optionally substituted branched or linear $C_{1-10}$ hydrocarbon chain. In some embodiments, $L^{aa}$ is optionally substituted $C_{1-10}$ (e.g., 1, 2, 3, 4, 5, 6, 7, 8, 9, or 10) alkylene. In some embodiments, $L^{aa}$ is optionally substituted —$CH_2$—$CH_2$—. In some embodiments, $L^{aa}$ is —$CH_2$—$CH_2$—. In some embodiments, $L^{aa}$ is optionally substituted —$CH_2$—. In some embodiments, $L^{aa}$ is —$CH_2$—.

As described above, each L is independently a covalent bond, or an optionally substituted, bivalent $C_1$-$C_{25}$ aliphatic or heteroaliphatic group having 1-10 heteroatoms wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—.

In some embodiments, L is a covalent bond.

In some embodiments, L (or $L^a$, $L^{aa}$, $L^{a1}$, $L^{a2}$, or another variable or moiety that can be L, or a linker moiety) is an optionally substituted, bivalent $C_1$-$C_{25}$, $C_1$-$C_{20}$, $C_1$-$C_{15}$, $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$, or $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$, aliphatic wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments, L is an optionally substituted, bivalent $C_1$-$C_{25}$ aliphatic wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments, L, or $L^a$, $L^{aa}$, $L^{a1}$, $L^{a2}$, or another variable or moiety that can be L, or a linker moiety, or a linker moiety, is an optionally substituted, bivalent $C_1$-$C_{25}$, $C_1$-$C_{20}$, $C_1$-$C_{15}$, $C_1$-$C_{10}$, $C_1$-$C_9$, $C_1$-$C_5$, $C_1$-$C_7$, $C_1$-$C_6$, $C_1$-$C_5$, $C_1$-$C_4$, $C_1$-$C_3$, $C_1$-$C_2$, or $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$, aliphatic wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments, it is an optionally substituted, bivalent $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$, or $C_1$, $C_2$, $C_3$, $C_4$, $C_5$, $C_6$, $C_7$, $C_8$, $C_9$, or $C_{10}$, aliphatic wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N (R')—, —N(R')C(O)N(R')—, —N(R')C(O)O—, —S(O)—, —$S(O)_2$—, —$S(O)_2N(R')$—, —C(O)S—, or —C(O)O—. In some embodiments, it is an optionally substituted, bivalent $C_2$ aliphatic wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments, it is an optionally substituted, bivalent $C_3$ aliphatic wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments, it is an optionally substituted, bivalent $C_4$ aliphatic wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments, it is an optionally substituted, bivalent $C_5$ aliphatic wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments, it is an optionally substituted, bivalent $C_6$ aliphatic wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments, the bivalent aliphatic is saturated. In some embodiments, the bivalent aliphatic is linear. In some embodiments, the bivalent aliphatic is branched. In some embodiments, it is an optionally substituted, bivalent linear saturated $C_6$ aliphatic wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments, each replacement if any is independently with -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments, each replacement if any is independently with -Cy-, —O—, —S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments, each replacement if any is independently with —O—, —S—, —N(R')—, —C(O)—, —S(O)—, —$S(O)_2$—, —$S(O)_2N(R')$—, —C(O)S—, or —C(O)O—. In some embodiments, each replacement if any is independently with —O—, —S—, —N(R')—, or —C(O)—. In some embodiments, L, or $L^a$, $L^{aa}$, $L^{a1}$, $L^{a2}$, or another variable or moiety that can be L, or a linker moiety, is an optionally substituted, bivalent $C_1$-$C_6$ linear saturated aliphatic wherein one or more methylene units is optionally and independently replaced with —O—, —S—, —N(R')—, or —C(O)—. In some embodiments, it is an optionally substituted, bivalent $C_1$-$C_5$ linear saturated aliphatic wherein one or more methylene units is optionally and independently replaced with —O—, —S—, —N(R')—, or —C(O)—. In some embodiments, it is an optionally substituted, bivalent $C_1$-$C_4$ linear saturated aliphatic wherein one or more methylene units is optionally and independently replaced with —O—, —S—, —N(R')—, or —C(O)—. In some embodiments, it is an optionally substituted, bivalent $C_1$-$C_3$ linear saturated aliphatic wherein one or more methylene units is optionally and independently replaced with —O—, —S—, —N(R')—, or —C(O)—. In some embodiments, it is an optionally substituted, bivalent $C_1$-$C_2$ linear saturated aliphatic wherein one or more methylene units is optionally and independently replaced with —O—, —S—, —N(R')—, or —C(O)—. In some embodiments, it is a bivalent $C_1$-$C_6$ linear saturated aliphatic wherein one or more methylene units is optionally and independently replaced with —O—, —S—, —N(R')—, or —C(O)—. In some embodiments, it is a bivalent $C_1$-$C_5$ linear saturated aliphatic wherein one or more methylene units is optionally and independently replaced with —O—, —S—, —N(R')—, or —C(O)—. In some embodiments, it is a bivalent $C_1$-$C_4$ linear saturated aliphatic wherein one or more methylene units is optionally and independently replaced with —O—, —S—, —N(R')—, or —C(O)—. In some embodiments, it is a bivalent $C_1$-$C_3$ linear saturated aliphatic wherein one or more methylene units is optionally and independently replaced with —O—, —S—, —N(R')—, or —C(O)—. In some embodiments, it is a bivalent $C_1$-$C_2$ linear saturated aliphatic wherein one or more methylene units is optionally and independently replaced with —O—, —S—, —N(R')—, or —C(O)—. In some embodiments, there is no replacement of methylene unit. In some embodiments, there is one replacement. In some embodiments, there is two replacement. In some embodiments, there is three replacement. In some embodiments, there is four or more replacement. In some embodiments, R' in each moiety that is utilized to replace a methylene unit (e.g., —N(R')—) as described herein is hydrogen or optionally substituted $C_{1-6}$ aliphatic or phenyl. In some embodiments, R' is each such moiety is hydrogen or optionally substituted $C_{1-6}$ alkyl. In some embodiments, R' is each such moiety is hydrogen or $C_{1-6}$ alkyl. In some embodiments, each -Cy- is optionally substituted bivalent ring selected from 3-10, 3-9, 3-8, 3-7, 5-10, 5-9, 5-8, 5-7, 5-6, or 3, 4, 5, 6, 7, 8, 9, or 10 membered cycloaliphatic and heterocyclylene having 1-3 heteroatoms, phenylene, and 5-6 membered heteroarylene having 1-3 heteroatoms. In some embodiments, -Cy- is optionally substituted bivalent 3-10, 3-9, 3-8, 3-7, 5-10, 5-9, 5-8, 5-7, 5-6, or 3, 4, 5, 6, 7, 8, 9, or 10 membered cycloaliphatic. In some embodiments, -Cy- is optionally substituted 3-10, 3-9, 3-8, 3-7, 5-10, 5-9, 5-8, 5-7, 5-6, or 3, 4, 5, 6, 7, 8, 9, or 10 membered heterocyclylene having 1-3 heteroatoms. In some embodiments, -Cy- is optionally substituted 3-10, 3-9, 3-8, 3-7, 5-10, 5-9, 5-8, 5-7, 5-6, or 3, 4, 5, 6, 7, 8, 9, or 10 membered heterocyclylene having 1 heteroatom. In some embodiments, -Cy- is optionally substituted phenylene. In some embodiments, -Cy- is phenylene. In some embodiments, -Cy- is optionally substituted 5-6 membered heteroarylene having 1-3 heteroatoms. In some embodiments, -Cy- is optionally substituted 5-6 membered heteroarylene having 1 heteroatom. In some embodiments, a heteroatom is nitrogen. In some embodiments, a heteroatom is oxygen. In some embodiments, a heteroatom is sulfur. In some embodiments, L, or $L^a$, $L^{aa}$, $L^{a1}$, $L^{a2}$, or another variable or moiety that can be L, or a linker moiety, or a linker moiety, is optionally substituted —$(CH_2)$n-. In some embodiments, it is —$(CH_2)$n-. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, L, $L^a$, $L^{aa}$, $L^{a1}$, $L^{a2}$, or another variable or moiety that can be L, or a linker moiety, is an optionally substituted, bivalent heteroaliphatic group having 1-10 heteroatoms wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—.

In some embodiments, L is an optionally substituted, bivalent heteroaliphatic group having 1-10 heteroatoms wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—.

Those skilled in the art appreciate that embodiments described for one linker moiety that can be L (e.g., $L^a$, $L^{aa}$, $L^{a1}$, $L^{a2}$, $L^{RN}$, etc.) may also be utilized for another group that can be L to the extent that such embodiments fall within the definition of L.

As will be clear to those skilled in the art reading the present disclosure, the letter "L" is used to refer to a linker moiety as described herein; each $L^{superscript}$ (e.g., $L^a$, $L^{aa}$, etc.) therefore is understood, in some embodiments, to be L, unless otherwise specified.

As described above, each R' is independently —R, —C(O)R, —$CO_2$R, or —$SO_2$R. In some embodiments, R' is -$L^a$-R. In some embodiments, R' is R. In some embodiments, R' is —C(O)R. In some embodiments, R' is —$CO_2$R. In some embodiments, R' is —$SO_2$R. In some embodiments, R' is —H.

As described above, each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

As described herein, in some embodiments, R is —H. In some embodiments, R is not —H. In some embodiments, R is optionally substituted $C_{1-10}$ aliphatic. In some embodiments, R is optionally substituted $C_{1-10}$ alkyl. In some embodiments, R is methyl. In some embodiments, R is ethyl. In some embodiments, R is isopropyl. In some embodiments, R is —$CF_3$. In some embodiments, R is —$CH_2CF_3$. In some embodiments, R is butyl. In some embodiments, R is t-butyl. In some embodiments, R is optionally substituted $C_{3-10}$ cycloaliphatic. In some embodiments, R is optionally substituted $C_{3-10}$ cycloalkyl. In some embodiments, R is optionally substituted cyclopropyl. In some embodiments, R is optionally substituted cyclobutyl. In some embodiments, R is optionally substituted cyclopentyl. In some embodiments, R is optionally substituted cyclohexyl. In some embodiments, R is optionally substituted phenyl. In some embodiments, R is phenyl. In some embodiments, R is optionally substituted 5-membered heteroaryl having 1-3 heteroatoms. In some embodiments, R is optionally substituted 5-membered heteroaryl having 1 heteroatom. In some embodiments, R is optionally substituted 6-membered heteroaryl having 1-3 heteroatoms. In some embodiments, R is optionally substituted 6-membered heteroaryl having 1 heteroatom. In some embodiments, R is optionally substituted bicyclic 8-10 membered aromatic ring having 0-5 heteroatoms. In some embodiments, R is optionally substituted bicyclic 9-membered aromatic ring having 1-5 heteroatoms. In some embodiments, R is optionally substituted bicyclic 10-membered aromatic ring having 1-5 heteroatoms. In some embodiments, R is optionally substituted bicyclic 9-membered aromatic ring having 1 heteroatom. In some embodiments, R is optionally substituted bicyclic 10-membered aromatic ring having 1 heteroatom. In some embodiments, R is optionally substituted bicyclic 10-membered aromatic ring having no heteroatom. In some embodiments, R is optionally substituted 3-10 membered heterocyclyl having 1-5 heteroatoms. In some embodiments, R is optionally substituted 5-14 membered bicyclic heterocyclyl having 1-5 heteroatoms.

In some embodiments, two R groups (or two groups that can be R, e.g., two groups each independently selected from R', $R^{a1}$, $R^{a2}$, $R^{a3}$, $R^{a5}$, $R^{RN}$, etc.) are taken together with their intervening atom(s) to form an optionally substituted 3-30 membered, monocyclic, bicyclic or polycyclic ring having, in addition to the atom, 0-10 heteroatoms. In some embodiments, a formed ring is substituted. In some embodiments, a formed ring is unsubstituted. In some embodiments, a formed ring is 3-30, 3-20, 3-15, 3-10, 3-9, 3-8, 3-7, 3-6, 4-10, 4-9, 4-8, 4-7, 4-6, 5-10, 5-9, 5-8, 5-7, 5-6, or 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 membered. In some embodiments, a formed ring is 3-10 membered. In some embodiments, a formed ring is 3-7 membered. In some embodiments, a formed ring is 4-10 membered. In some embodiments, a formed ring is 4-7 membered. In some embodiments, a formed ring is 5-10 membered. In some embodiments, a formed ring is 5-7 membered. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is 8-membered. In some embodiments, a formed ring is 9-membered. In some embodiments, a formed ring is 10-membered. In some embodiments, a formed ring is monocyclic. In some embodiments, a formed ring is bicyclic. In some embodiments, a formed ring is polycyclic. In some embodiments, a formed ring has no heteroatoms in addition to the intervening atom(s). In some embodiments, a formed ring has 1-10, e.g., 1-5, 1-3, or 1, 2, 3, 4, 5, 6, 7, 8, 9, or 10 heteroatoms in addition to the intervening atom(s). In some embodiments, a formed ring is saturated. In some embodiments, a formed ring is partially unsaturated. In some embodiments, a formed ring comprises one or more aromatic ring. In some embodiments, a formed ring is bicyclic or polycyclic, and each monocyclic unit is independently 3-10 membered, saturated, partially unsaturated or aromatic and having 0-5 heteroatoms. In some embodiments, each heteroatom is independently selected from nitrogen, oxygen and sulfur.

In some embodiments, a group that can be R, e.g., R', $R^{a1}$, $R^{a2}$, $R^{a3}$, $R^{a5}$, $R^{RN}$, etc., is R as described herein. Those skilled in the art appreciate that embodiments described for one group that can be R may also be utilized for another group that can be R to the extent that such embodiments fall within the definition of R.

In some embodiments, the present disclosure provides compounds having the structure of

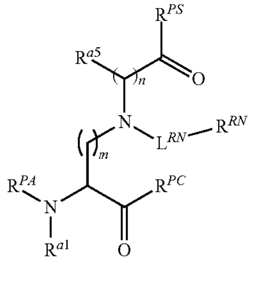

or a salt thereof, wherein:

each of m and n is independently 1, 2, 3, or 4;

$L^{RN}$ is L;

$R^{RN}$ is R; and $R^{a5}$ is R'.

In some embodiments, m is 1. In some embodiments, m is 2. In some embodiments, m is 3. In some embodiments, m is 4.

In some embodiments, n is 1. In some embodiments, n is 2. In some embodiments, n is 3. In some embodiments, n is 4.

In some embodiments, $L^{RN}$ is $CH_2$—, —CO—, or —$SO_2$—. In some embodiments, $L^{RN}$ is —$CH_2$—. In some embodiments, $L^{RN}$ is —CO—. In some embodiments, $L^{RN}$ is —$SO_2$—. In some embodiments, $L^{RN}$ is optionally substituted bivalent $C_{1-4}$ alkylene. In some embodiments, $L^{RN}$ is optionally substituted bivalent linear $C_{1-4}$ alkylene. In some embodiments, $L^{RN}$ is —$CH_2$—$CH_2$—. In some embodiments, $L^{RN}$ is —$CH_2$—$CH_2$—$CH_2$—. In some embodiments, $L^{RN}$ is —$C(CH_3)$—.

In some embodiments, $R^{RN}$ is R as described herein. In some embodiments, $R^{RN}$ is $C_{1-7}$ alkyl or heteroalkyl having 1-4 heteroatoms, wherein the alkyl or heteroalkyl is optionally substituted with one or more groups independently selected from halogen, a $C_{5-6}$ aromatic ring having 0-4 heteroatoms, and an optionally substituted 3-10 membered cycloalkyl or heteroalkyl ring having 1-4 heteroatoms.

In some embodiments, R (e.g., $R^{RN}$, R', etc.) is optionally substituted aliphatic, e.g., $C_{1-10}$ aliphatic. In some embodiments, R is optionally substituted alkyl, e.g., $C_{1-10}$ alkyl. In some embodiments, R is optionally substituted cycloalkyl, e.g., $C_{1-10}$ cycloalkyl. In some embodiments, R is optionally substituted aryl. In some embodiments, R is optionally substituted heterocyclyl. In some embodiments, R is optionally substituted heteroaryl. In some embodiments, is methyl. In some embodiments, R is —$CF_3$. In some embodiments, R is ethyl. In some embodiments, R is

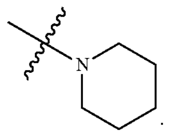 [SMILES: *N1CCCCC1]

In some embodiments, R is phenyl. In some embodiments, R is pentafluorophenyl. In some embodiments, R is pyridinyl.

In some embodiments, one or more $R^{a5}$ are independently —H. In some embodiments, one or more $R^{a5}$ are independently optionally substituted $C_{1-6}$ alkyl. In some embodiments, each $R^{a5}$ is —H.

In some embodiments, -$L^{RN}$-$R^{RN}$ is R, and is taken together with a $R^{a5}$ and their intervening atoms to form an optionally substituted, 3-30 membered, monocyclic, bicyclic or polycyclic ring having, in addition to the intervening atoms, 0-10 heteroatoms.

As described in the present disclosure, various rings, including those in various moieties (e.g., R or various groups that can be R, various bivalent rings such as those in -Cy-) and those formed by two entities (e.g., two groups that are or can be R) taken together with their intervening forms, can be various sizes, e.g., 3-30. In some embodiments, a ring is 3-30-membered. In some embodiments, a ring is 3-20 membered. In some embodiments, a ring is 3-10 membered. In some embodiments, a ring is e.g., 3, 4, 5, 6, 7, 8, 9, or 10-membered. In some embodiments, a ring is 3-membered. In some embodiments, a ring is 4-membered. In some embodiments, a ring is 5-membered. In some embodiments, a ring is 6-membered. In some embodiments, a ring is 7-membered. In some embodiments, a ring is 8-membered. In some embodiments, a ring is 9-membered. In some embodiments, a ring is 10-membered. In some embodiments, a ring is substituted (in addition to potential groups already drawn out in formulae). In some embodiments, a ring is not substituted. In some embodiments, a ring is saturated. In some embodiments, a ring is partially unsaturated. In some embodiments, a ring is aromatic. In some embodiments, a ring comprise one or more, e.g., 1-5, heteroatoms. In some embodiments, one or more heteroatoms are oxygen. In some embodiments, one or more heteroatoms are nitrogen. In some embodiments, one or more heteroatoms are sulfur. In some embodiments, a ring is a cycloaliphatic, e.g., cycloalkyl ring. In some embodiments, a ring is a heterocycloaliphatic, e.g., heterocycloalkyl ring. In some embodiments, a ring is an aryl ring. In some embodiments, a ring is a heteroaryl ring. In some embodiments, a ring is a heteroaryl ring. In some embodiments, a ring is monocyclic. In some embodiments, a ring is bicyclic or polycyclic. In some embodiments, each monocyclic unit in a ring is independently an optionally substituted, 3-10 membered (e.g., 3, 4, 5, 6, 7, 8, 9, or 10-membered), saturated, partially unsaturated or aromatic ring having 0-5 heteroatoms.

As described herein, in some embodiments, a heteroatom is selected from nitrogen, oxygen, sulfur, silicon and phosphorus. As described herein, in some embodiments, a heteroatom is selected from nitrogen, oxygen, and sulfur.

In some embodiments, $R^{a1}$ is -L-R wherein each variable is independently as described herein. In some embodiments, L is a covalent bond or an optionally substituted, bivalent $C_1$-$C_6$ aliphatic group wherein one or more methylene units of the group are optionally and independently replaced with -Cy-, —O—, —S—, —N(R')—, —C(O)—, —C(O)N(R')—, —N(R')C(O)N(R')—, —N(R')C(O)O—, or —C(O)O—. In some embodiments, $R^{a1}$ is R as described herein. In some embodiments, R is —H. In some embodiments, R is optionally substituted $C_{1-6}$ aliphatic. In some embodiments, R is optionally substituted $C_{1-6}$ alkyl. In some embodiments, R is methyl. In some embodiments, $R^{a1}$ are taken together with another group, e.g., $R^{a3}$ and their intervening atoms to form an optionally substituted ring as described herein. In some embodiments, $R^{a1}$ and $R^{a3}$ are taken together with their intervening atoms to form an optionally substituted 3-30 membered, monocyclic, bicyclic or polycyclic ring having, in addition to the atom, 0-10 heteroatoms. In some embodiments, a formed ring is substituted. In some embodiments, a formed ring is unsubstituted. In some embodiments, a formed ring is 3-30, 3-20, 3-15, 3-10, 3-9, 3-8, 3-7, 3-6, 4-10, 4-9, 4-8, 4-7, 4-6, 5-10, 5-9, 5-8, 5-7, 5-6, or 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 membered. In some embodiments, a formed ring is 3-10 membered. In some embodiments, a formed ring is 3-7 membered. In some embodiments, a formed ring is 4-10 membered. In some embodiments, a formed ring is 4-7 membered. In some embodiments, a formed ring is 5-10 membered. In some embodiments, a formed ring is 5-7 membered. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is 8-membered. In some embodiments, a formed ring is 9-membered. In some embodiments, a formed ring is 10-membered. In some embodiments, a formed ring is monocyclic. In some embodiments, a formed ring is bicyclic. In some embodiments, a formed ring is polycyclic. In some embodiments, a formed ring has no heteroatoms in addition to the intervening atom(s). In some embodiments, a formed ring has 1-10, e.g., 1-5, 1-3, or 1, 2, 3, 4, 5, 6, 7, 8, 9, or 10 heteroatoms in addition to the intervening atom(s). In some embodiments, a formed ring is saturated. In some embodiments, a formed ring is partially unsaturated. In some embodiments, a formed ring comprises one or more aromatic ring. In some embodiments, a formed ring is bicyclic or polycyclic, and each monocyclic unit is independently 3-10 membered, saturated, partially unsaturated or aromatic and having 0-5 heteroatoms. In some embodiments, each heteroatom is independently selected from nitrogen, oxygen and sulfur. In some embodiments, a formed ring is an optionally substituted 5-membered ring having no additional heteroatom in addition to the nitrogen atom to which $R^{a1}$ is attached. In some embodiments, a formed ring is an optionally substituted 6-membered ring having no additional heteroatom in addition to the nitrogen atom to which $R^{a1}$ is attached.

In some embodiments, $R^{a3}$ is -L-R wherein each variable is independently as described herein. In some embodiments, L is a covalent bond or an optionally substituted, bivalent $C_1$-$C_6$ aliphatic group wherein one or more methylene units of the group are optionally and independently replaced with -Cy-, —O—, —S—, —N(R')—, —C(O)—, —C(O)N(R')—, —N(R')C(O)N(R')—, —N(R')C(O)O—, or —C(O)O—. In some embodiments, $R^{a3}$ is R as described herein. In some embodiments, R is —H. In some embodiments, R is optionally substituted $C_{1-6}$ aliphatic. In some embodiments, R is optionally substituted $C_{1-6}$ alkyl. In some embodiments, R is methyl.

In some embodiments, —C(O)$R^{PC}$ is a protected carboxylic acid group. In some embodiments, —C(O)$R^{PC}$ is an activated carboxylic acid group. Those skilled in the art will appreciate that various groups are available for protecting/activating carboxyl groups, including various groups that are useful in peptide synthesis, and can be utilized in accordance with the present disclosure. In some embodiments, —C(O)$R^{PC}$ is an ester. In some embodiments, —C(O)$R^{PC}$ is an activated ester for synthesis. In some embodiments, —C(O)$R^{PC}$ is —C(O)OR'. In some embodiments, R' is R. In some embodiments, R' is optionally substituted $C_{1-10}$ aliphatic. In some embodiments, R' optionally substituted phenyl. In some embodiments, R' is pentafluorophenyl. In some embodiments, R' is

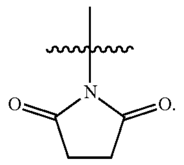 [SMILES: *N1C(=O)CCC1=O]

In some embodiments, —C(O)$R^{PC}$ is —COOH.

In some embodiments, —C(O)$R^{PS}$ is a protected carboxylic acid group. In some embodiments, —C(O)$R^{PS}$ is an activated carboxylic acid group if it is to be reacted with another moiety. Those skilled in the art will appreciate that various groups are available for protecting/activating carboxyl groups, including various groups that are useful in peptide synthesis, and can be utilized in accordance with the present disclosure. In some embodiments, —C(O)$R^{PS}$ is an ester. In some embodiments, —C(O)$R^{PS}$ is an ester. In some embodiments, —C(O)$R^{PS}$ is —C(O)OR'. In some embodiments, R' is R. In some embodiments, R is optionally substituted $C_{1-10}$ aliphatic. In some embodiments, R optionally substituted phenyl. In some embodiments, R is optionally substituted t-Bu. In some embodiments, R is t-Bu. In some embodiments, R is benzyl. In some embodiments, R is allyl. In some embodiments, —C(O)$R^{PS}$ is a protected carboxylic acid group that is compatible with peptide synthesis (e.g., Fmoc-based peptide synthesis). In some embodiments, —C(O)$R^{PS}$ is a protected carboxylic acid group which is orthogonal to —C(O)$R^{PC}$ and $R^{PA}$, and remains intact when —C(O)$R^{PS}$ and/or N($R^{PA}$)($R^{a1}$) are protected, deprotected, and/or reacted (e.g., in peptide synthesis such as Fmoc-based peptide synthesis). In some embodiments, —C(O)$R^{PS}$ is deprotected at a late stage during synthesis, e.g., after a peptide backbone is or is largely constructed such that an unprotected side chain —COOH does not impact synthesis.

In some embodiments, —C(O)$R^{PS}$ is —COOH.

As described above, $R^{PA}$ is —H or an amino protecting group. In some embodiments, $R^{PA}$ is —H. In some embodiments, $R^{PA}$ is an amino protecting group. In some embodiments, $R^{PA}$ is an amino protecting group suitable for peptide synthesis. In some embodiments, $R^{PA}$ is —C(O)—O—R, wherein R is optionally substituted

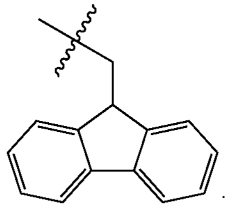 [SMILES: *CC1c2ccccc2-c2ccccc21]

In some embodiments, $R^{PA}$ is -Fmoc. In some embodiments, $R^{PA}$ is -Cbz. In some embodiments, $R^{PA}$ is -Boc.

In some embodiments, $R^{PS}$ is a protecting group orthogonal to $R^{PA}$. In some embodiments, $R^{PS}$ is a protecting group orthogonal to $R^{PC}$. In some embodiments, $R^{PS}$ is compatible with peptide synthesis. In some embodiments, $R^{PS}$ is optionally substituted $C_{1-6}$ aliphatic. In some embodiments, $R^{PS}$ is t-butyl.

In some embodiments, $R^{PS}$ is —S-L-R', wherein each variable is independently as described herein. In some embodiments, L is optionally substituted —$CH_2$—. In some embodiments, L is —$CH_2$—. In some embodiments, $R^{PS}$ is —S—$CH_2$—R', wherein R' is as described herein. In some embodiments, R' is R as described herein. In some embodiments, R is optionally substituted $C_{6-30}$ aryl. In some embodiments, R is optionally substituted $C_{6-10}$ aryl. In some embodiments, R is optionally substituted phenyl. In some embodiments, R is phenyl. In some embodiments, R is substituted phenyl wherein one or more substituents are independently alkoxy. In some embodiments, R is 2, 4, 6-trimethoxyphenyl. In some embodiments, R is optionally substituted 5-30 membered heteroaryl having 1-10 heteroatoms. In some embodiments, R is optionally substituted 5-10 membered heteroaryl having 1-4 heteroatoms. In some embodiments, R is optionally substituted 5-membered heteroaryl having 1-4 heteroatoms. In some embodiments, $R^{PS}$ is —S—$CH_2$—Cy-R', wherein the —$CH_2$— is optionally substituted, and -Cy- is as described herein. In some embodiments, $R^{Ps}$ is —S—$CH_2$—Cy-O—R', wherein the —$CH_2$— is optionally substituted, and -Cy- is as described herein. In some embodiments, -Cy- is an optionally substituted aromatic ring. In some embodiments, -Cy- is optionally substituted phenylene. In some embodiments, -Cy- is 2, 6-dimethoxy-1, 4-phenylene. In some embodiments, -Cy- is 2, 4, 6-trimethoxy-1, 3-phenylene. In some embodiments, $R^{PS}$ is

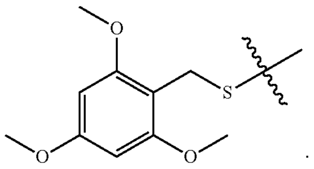 [SMILES: *SCc1c(OC)cc(OC)cc1OC]

In some embodiments, $R^{PS}$ is —SH.

In some embodiments, $R^{a2}$ is

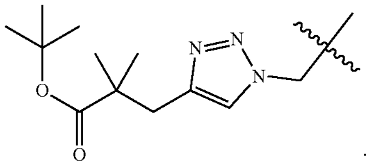 [SMILES: *Cn1cc(CC(C)(C)C(=O)OC(C)(C)C)nn1]

In some embodiments, $R^{a2}$ is

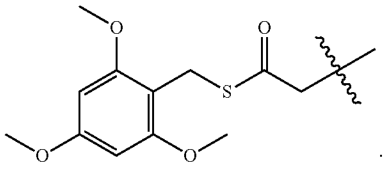 [SMILES: *CC(=O)SCc1c(OC)cc(OC)cc1OC]

In some embodiments, $R^{a2}$ is

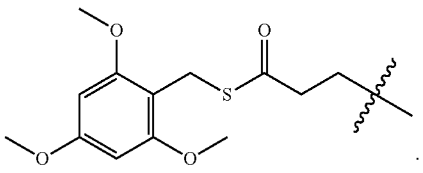 [SMILES: *CCC(=O)SCc1c(OC)cc(OC)cc1OC]

In some embodiments, $R^{a2}$ is

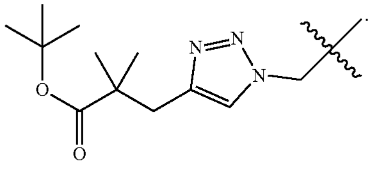 [SMILES: *Cn1cc(CC(C)(C)C(=O)OC(C)(C)C)nn1]

In some embodiments, —$C(R^{a2})(R^{a3})$— is

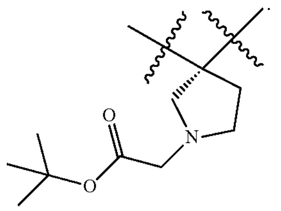

In some embodiments, a provided compound is selected from:

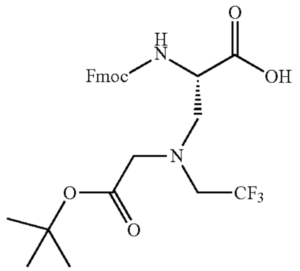

(TfcGA)

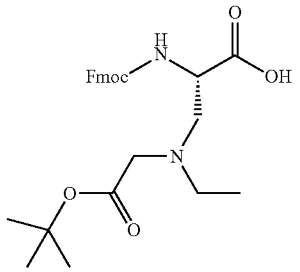

(EtGA)

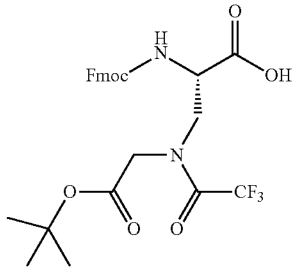

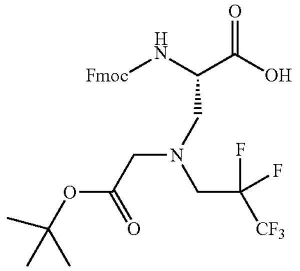

-continued

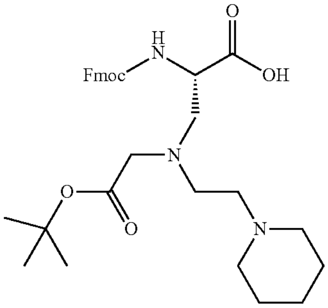

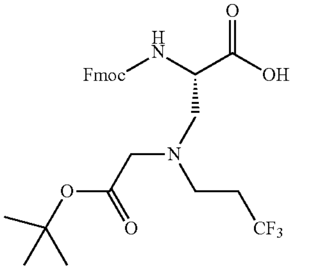

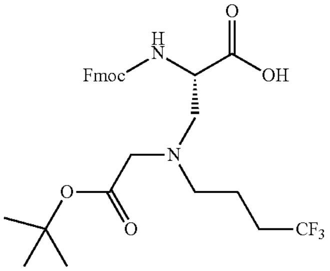

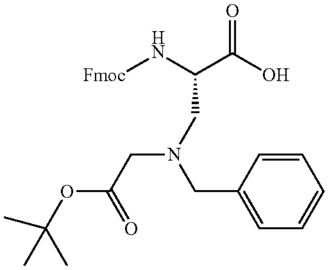

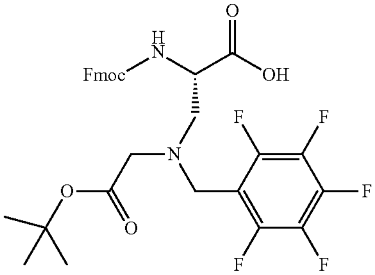

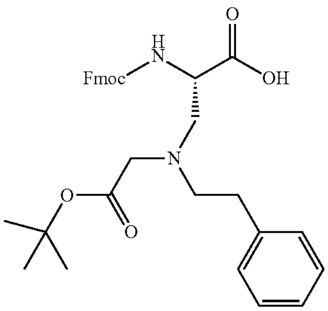

-continued

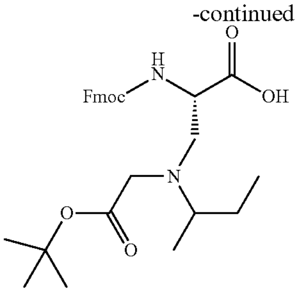

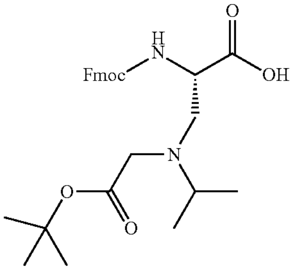

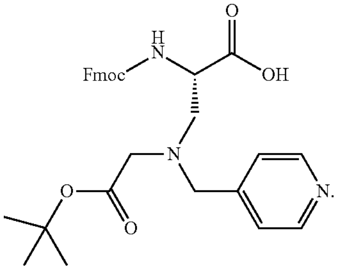

In some embodiments, $R^{a2}$ is $R^{a2}$ in a compound described above (a non-hydrogen group attached to an alpha carbon).

In some embodiments, the present disclosure provides compounds having the structure of:

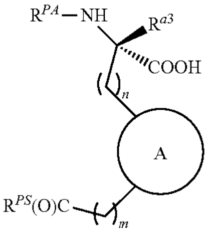

or a salt thereof, wherein:

Ring A is an optionally substituted 3-10 membered ring;

n is 0-6; and m is 0-6.

In some embodiments, m is 0. In some embodiments, m is 1-6.

In some embodiments, the present disclosure provides compounds having the structure of:

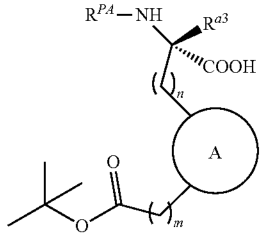

or a salt thereof, wherein:

Ring A is an optionally substituted 3-10 membered ring;

n is 0-6; and m is 0-6.

In some embodiments, m is 0. In some embodiments, m is 1-6.

In some embodiments, the present disclosure provides compounds having the structure of:

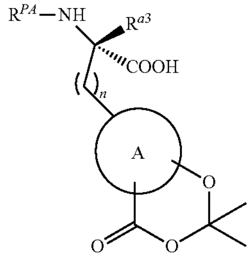

or a salt thereof, wherein:

Ring A is an optionally substituted 3-10 membered ring;

n is 0-6; and m is 0-6.

In some embodiments, m is 0. In some embodiments, m is 1-6.

In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, n is 0, 1, or 2.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 1, 2, or 3.

In some embodiments, Ring A is a ring as described herein. In some embodiments, Ring A is 3-membered. In some embodiments, Ring A is 4-membered. In some embodiments, Ring A is 5-membered. In some embodiments, Ring A is 6-membered. In some embodiments, Ring A is 7-membered. In some embodiments, Ring A is 8-membered. In some embodiments, Ring A is 9-membered. In some embodiments, Ring A is 10-membered. In some embodiments, Ring A is saturated. In some embodiments, Ring A is partially unsaturated. In some embodiments, Ring A is aromatic. In some embodiments, Ring A has no additional heteroatoms in addition to the nitrogen atom. In some embodiments, Ring is unsubstituted. In some embodiments, Ring A is substituted with one or more halogen. In some embodiments, Ring A is substituted with one or more —F. In some embodiments, Ring A has a carbon substituted with two —F. In some embodiments, —C(O)$R^{PS}$ is at 2'-position (N being position 1). In some embodiments, —C(O)$R^{PS}$ is at 3'-position. In some embodiments, —C(O)$R^{PS}$ is at 4'-position. In some embodiments, —C(O)$R^{PS}$ is attached to a chiral center, e.g., a chiral carbon atom. In some embodiments, a chiral center is R. In some embodiments, a chiral center is S. In some embodiments, Ring A is bonded to —$(CH_2)$n- at a chiral carbon which is R. In some embodiments, Ring A is bonded to —$(CH_2)$n- at a chiral carbon which is S. In some embodiments, —$(CH_2)$n- is at position 2 (the N is at position 1). In some embodiments, —$(CH_2)$n- is at position 3 (the N is at position 1). In some embodiments, —$(CH_2)$n- is at position 4 (the N is at position 1).

In some embodiments, Ring A is substituted. In some embodiments, substituents on Ring A are of suitable properties, e.g., volumes, for various utilizations. In some embodiments, substituents are independently selected from halogen, —R, —$CF_3$, —$N(R)_2$, —CN, and —OR, wherein each R is independently $C_{1-6}$ aliphatic optionally substituted with one or more —F. In some embodiments, substituents are independently selected from halogen, $C_{1-5}$ linear, branched or cyclic alkyl, —OR wherein R is $C_{1-4}$ linear, branched or cyclic alkyl, fluorinated alkyl, —$N(R)_2$ wherein each R is independently $C_{1-6}$ linear, branched or cyclic alkyl, or —CN. In some embodiments, substituents are selected from halogen, a $C_{5-6}$ aromatic ring having 0-4 heteroatoms, and an optionally substituted 3-10 membered cycloalkyl or heteroalkyl ring having 1-4 heteroatoms. In some embodiments, a substituent is halogen. In some embodiments, it is —F. In some embodiments, it is —Cl. In some embodiments, it is —Br. In some embodiments, it is —I. In some embodiments, a substituent is optionally substituted $C_{1-4}$ alkyl. In some embodiments, a substituent is $C_{1-4}$ alkyl. In some embodiments, it is methyl. In some embodiments, it is ethyl. In some embodiments, it is i-Pr. In some embodiments, a substituent is $C_{1-4}$ haloalkyl. In some embodiments, a substituent is $C_{1-4}$ alkyl optionally substituted with one or more —F. In some embodiments, it is —$CF_3$. In some embodiments, it is —CN. In some embodiments, it is —OR wherein R is optionally substituted $C_{1-4}$ alkyl. In some embodiments, it is —OR wherein R is $C_{1-4}$ alkyl. In some embodiments, it is —OR wherein R is $C_{1-4}$ haloalkyl. In some embodiments, it is —OR wherein R is $C_{1-4}$ alkyl optionally substituted with one or more —F. In some embodiments, it is —$OCF_3$.

In some embodiments, Ring A is or comprises an optionally substituted saturated monocyclic ring. In some embodiments, Ring A is or comprises an optionally substituted partially unsaturated monocyclic ring. In some embodiments, Ring A is or comprises an optionally substituted aromatic monocyclic ring. In some embodiments, Ring A is optionally substituted phenyl. In some embodiments, Ring A is optionally substituted 5-6 membered heteroaryl having 1-3 heteroatoms. In some embodiments, Ring A is optionally substituted 5-6 membered heteroaryl having 1-3 heteroatoms, wherein at least one heteroatom is nitrogen. In some embodiments, Ring A is an optionally substituted 8-10 membered bicyclic ring having 1-6 heteroatoms. In some embodiments, Ring A is an optionally substituted 8-10 membered bicyclic aromatic ring having 1-6 heteroatoms, wherein each monocyclic unit is independently an optionally 5-6 membered aromatic ring having 0-3 heteroatoms. In some embodiments, Ring A is bonded to —$(CH_2)$n- at a carbon atom. In some embodiments, Ring A is bonded to —$(CH_2)$n- at a nitrogen atom. In some embodiments, Ring A or -Cy- in $L^{aa}$ is optionally substituted, and each substitute is independently selected from halogen, —R, —$CF_3$, —$N(R)_2$, —CN, and —OR, wherein each R is independently $C_{1-6}$ aliphatic optionally substituted with one or more —F. In some embodiments, Ring A or -Cy- in $L^{aa}$ is optionally substituted, and each substitute is independently selected from halogen, $C_{1-5}$ linear, branched or cyclic alkyl, —OR wherein R is $C_{1-4}$ linear, branched or cyclic alkyl, fluorinated alkyl, —$N(R)_2$ wherein each R is independently $C_{1-6}$ linear, branched or cyclic alkyl, or —CN.

In some embodiments, Ring A is optionally substituted phenyl. In some embodiments, the present disclosure provides a compound of formula

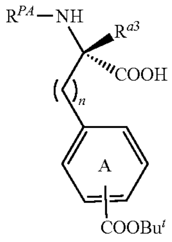

or a salt thereof, wherein Ring A is optionally substituted phenyl, and each variable is as described herein.

In some embodiments, the present disclosure provides compounds having the structure of

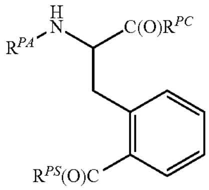

or a salt thereof, wherein each variable is independent as described herein. In some embodiments, the present disclosure provides compounds having the structure of

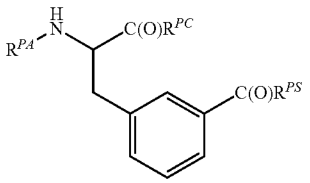

or a salt thereof, wherein each variable is independent as described herein.

In some embodiments, a compound is selected from:

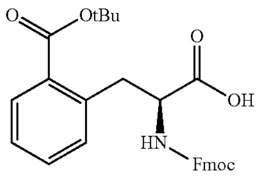

(2COOHF)

-continued

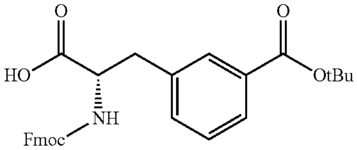

(3COOHF)

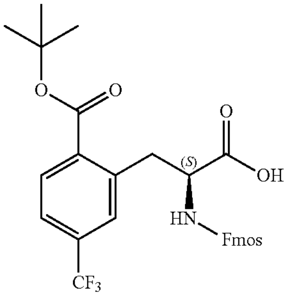

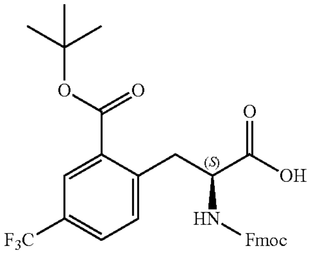

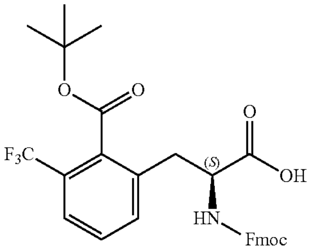

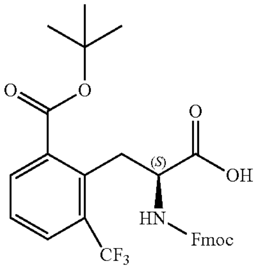

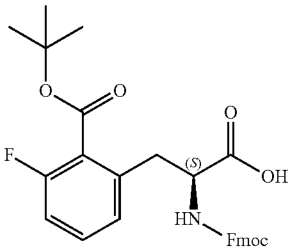

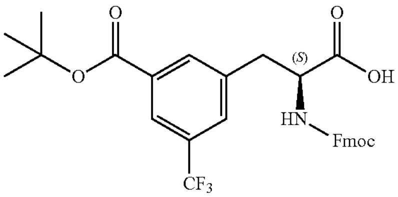

-continued

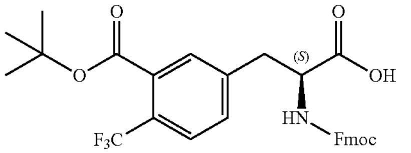

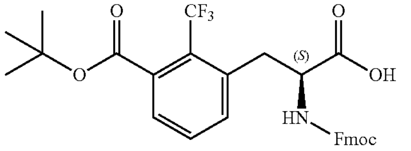

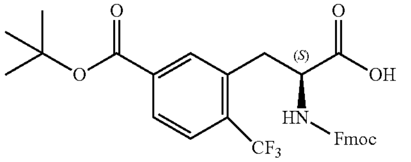

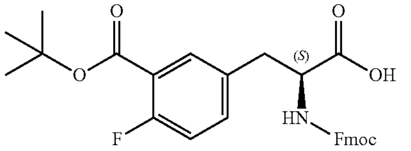

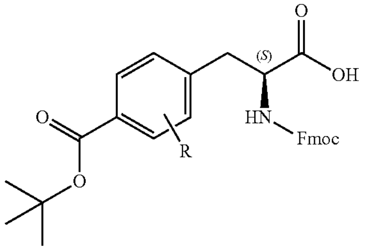

(R = F, or $CF_3$)

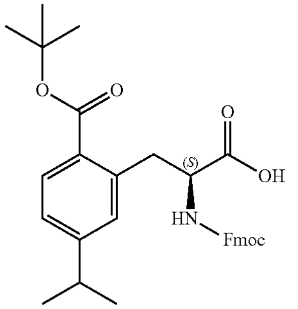

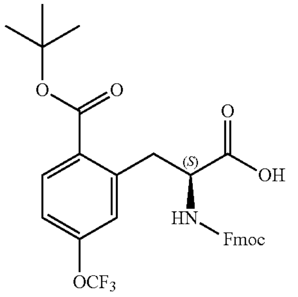

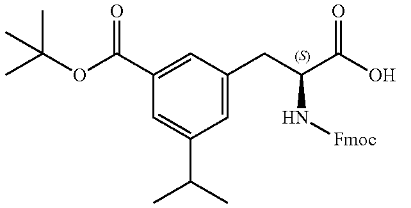

-continued

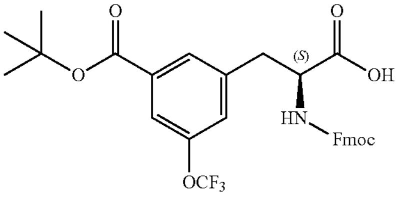

In some embodiments, the present disclosure provides a compound of formula

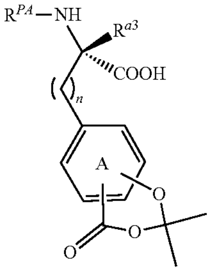

or a salt thereof, wherein Ring A is optionally substituted phenyl, and each variable is as described herein. In some embodiments, a compound is selected from:

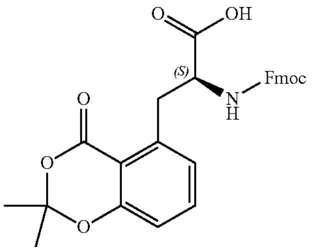

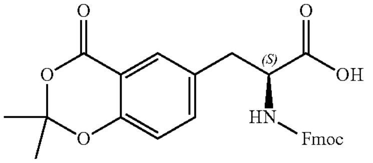

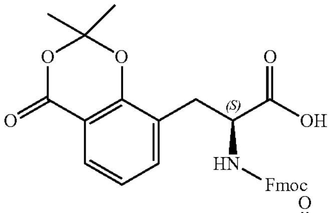

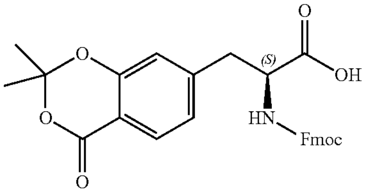

In some embodiments, Ring A is an optionally substituted 5- or 6-membered heteroaryl having 1-4 heteroatoms. In some embodiments, a provided compound has the structure of

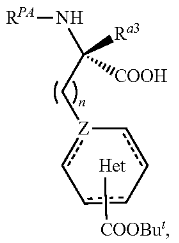

wherein Z is carbon or a heteroatom, Ring Het is an optionally substituted 5- or 6-membered heteroaryl having 1-4 heteroatoms, and each other variable is independently as described herein. In some embodiments, a provided compound is selected from:

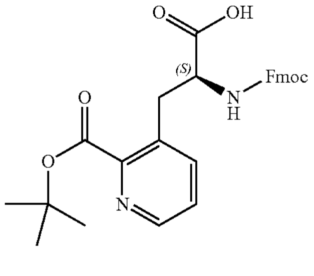

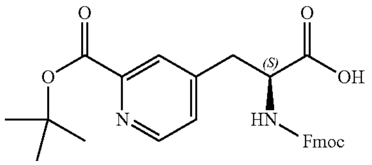

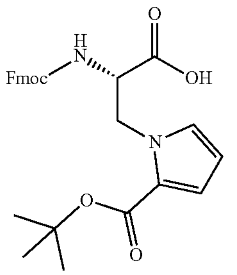

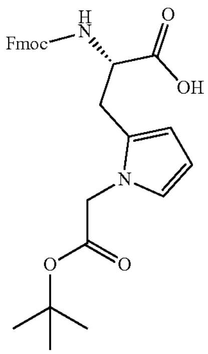

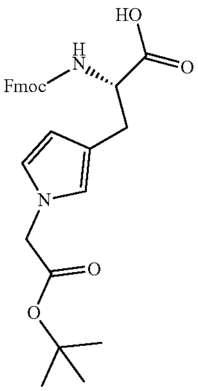

-continued

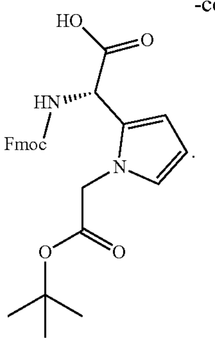

In some embodiments, Ring A is a 8-10 membered bicyclic aryl or a heteroaryl ring having 1-5 heteroatoms. In some embodiments, Ring A is a 10-membered bicyclic aryl ring. In some embodiments, Ring A is a 8-membered bicyclic heteroaryl ring having 1-5 heteroatoms. In some embodiments, Ring A is a 9-membered bicyclic heteroaryl ring having 1-5 heteroatoms. In some embodiments, Ring A is a 10-membered bicyclic heteroaryl ring having 1-5 heteroatoms. In some embodiments, Ring A is an optionally substituted 5- or 6-membered heteroaryl having 1-4 heteroatoms. In some embodiments, a provided compound has the structure of

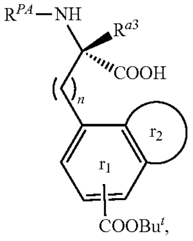

wherein each of Ring r1 and r2 is independently an optionally substituted 5- or 6-membered aryl or heteroaryl ring having 1-4 heteroatoms, and each other variable is independently as described herein. In some embodiments, a provided compound has the structure of

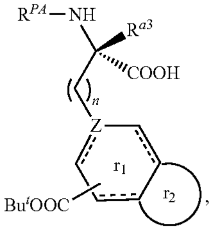

wherein Z is carbon or a heteroatom, each of Ring r1 and r2 is independently an optionally substituted 5- or 6-membered aryl or heteroaryl ring having 1-4 heteroatoms, and each other variable is independently as described herein. In some embodiments, a provided compound is selected from:

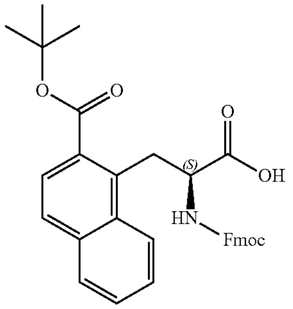
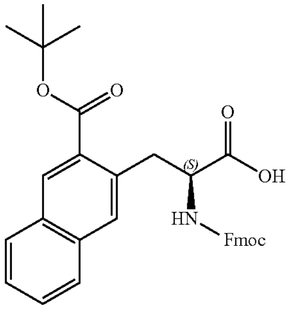
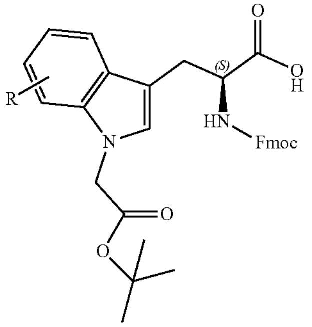
In some embodiments, the present disclosure provides a compound of structure
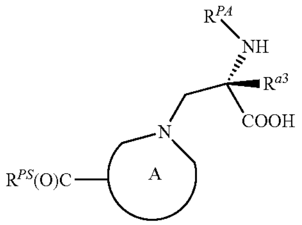
or a salt thereof. In some embodiments, —C(O)$R^{PS}$ is —C(O)—OtBu. In some embodiments, the present disclosure provides a compound of structure
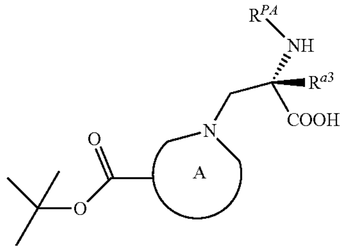
or a salt thereof, wherein each variable is independently as described herein.
In some embodiments, a provided compound is selected from:
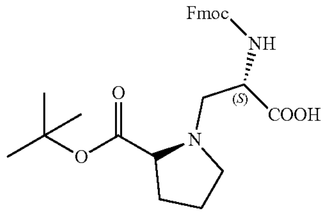
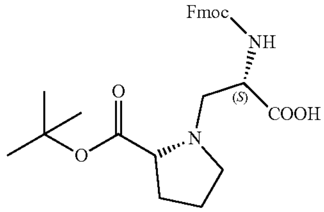
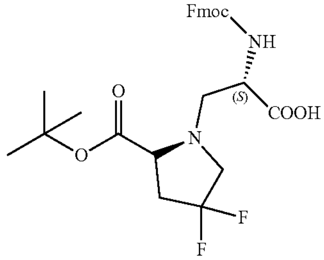
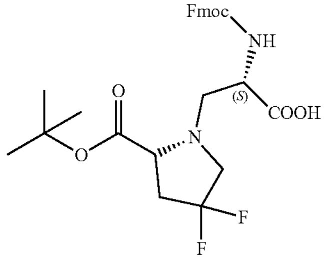
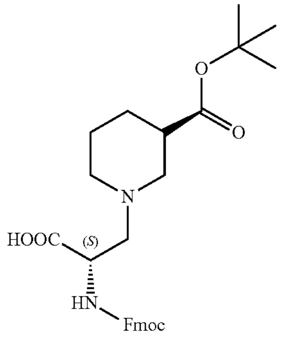

-continued

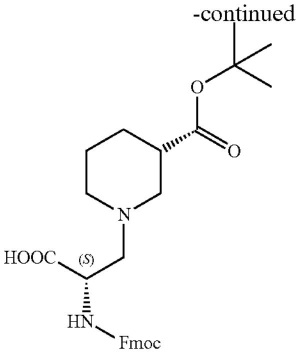

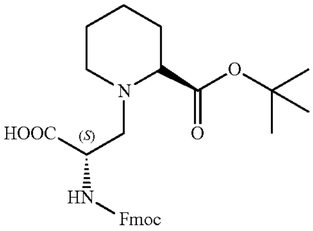

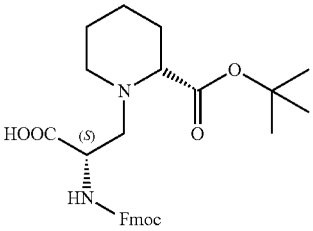

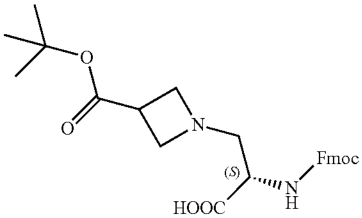

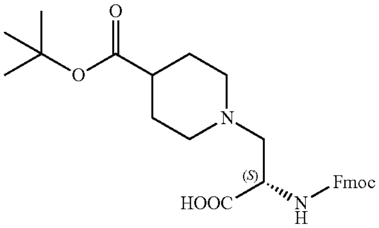

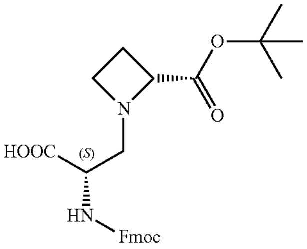

-continued

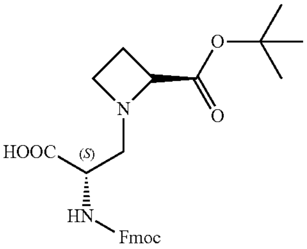

In some embodiments, the present disclosure provides compounds having the structure of

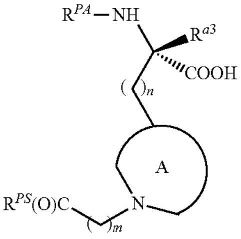

or a salt thereof, wherein each variable is independently as described herein. In some embodiments, the present disclosure provides compounds having the structure of

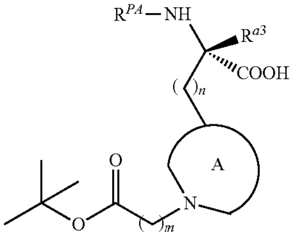

or a salt thereof, wherein each variable is independently as described herein.

In some embodiments, a provided compound is selected from:

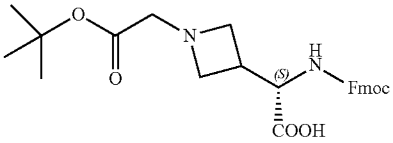

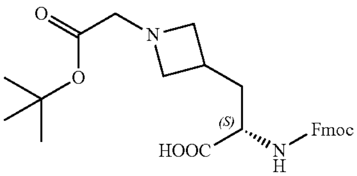

-continued

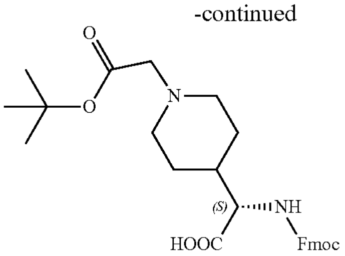

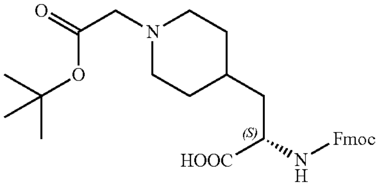

In some embodiments, a provided compound is an amino acid. In some embodiments, a provided compound is a protected amino acid. In some embodiments, a provided compound is a protected and/or activated amino acid. In some embodiments, a provided compound is suitable for In some embodiments, a ring moiety of, e.g., -Cy-, R (including those formed by R groups taken together), etc. is monocyclic. In some embodiments, a ring moiety is bicyclic or polycyclic. In some embodiments, a monocyclic ring is an optionally substituted 3-10 (3, 4, 5, 6, 7, 8, 9, or 10, 3-8, 3-7, 4-7, 4-6, 5-6, etc.) membered, saturated, partially unsaturated or aromatic ring having 0-5 heteroatoms. In some embodiments, each monocyclic ring unit of a bicyclic or polycyclic ring moiety is independently an optionally substituted 3-10 (3, 4, 5, 6, 7, 8, 9, or 10, 3-8, 3-7, 4-7, 4-6, 5-6, etc.) membered, saturated, partially unsaturated or aromatic ring having 0-5 heteroatoms.

In some embodiments, each heteroatom is independently selected from oxygen, nitrogen, sulfur, phosphorus and silicon. In some embodiments, each heteroatom is independently selected from oxygen, nitrogen, and sulfur.

In some embodiments, $L^{a1}$ is a covalent bond. In some embodiments, a compound of formula PA is of the structure $NH(R^{a1})—C(R^{a2})(R^{a3})\text{-}L^{a2}\text{-}COOH$.

In some embodiments, $L^{a2}$ is a covalent bond. In some embodiments, a compound of formula PA is of the structure $NH(R^{a1})—C(R^{a2})(R^{a3})\text{-}L^{a2}\text{-}COOH$.

In some embodiments, $L^{a1}$ is a covalent bond and $L^{a2}$ is a covalent bond. In some embodiments, a compound of formula PA is of the structure $NH(R^{a1})—C(R^{a2})(R^{a3})—COOH$.

In some embodiments, an amino acid is suitable for stapling. In some embodiments, an amino acid comprises a terminal olefin.

In some embodiments, an amino acid has the structure of $NH(R^{a1})\text{-}L^{a1}\text{-}C(\text{-}L^{aa}\text{-}COOH)(R^{a3})\text{-}L^{a2}\text{-}COOH$, or a salt thereof, wherein each variable is independently as described in the present disclosure. In some embodiments, $L^{aa}$ is $\text{-}L^{am1}\text{-}N(R')\text{-}L^{am2}\text{-}$, wherein each variable is as described herein. In some embodiments, each of $L^{am1}$ and $L^{am2}$ is optionally substituted bivalent $C_{1-6}$ aliphatic. In some embodiments, each of $L^{am1}$ and $L^{am2}$ is bivalent $C_{1-6}$ aliphatic. In some embodiments, each of $L^{am1}$ and $L^{am2}$ is optionally substituted bivalent $C_{1-6}$ alkyl. In some embodiments, each of $L^{am1}$ and $L^{am2}$ is bivalent $C_{1-6}$ alkyl. In some embodiments, each of $L^{am1}$ and $L^{am2}$ is optionally substituted bivalent linear $C_{1-6}$ alkyl. In some embodiments, each of $L^{am1}$ and $L^{am2}$ is bivalent linear $C_{1-6}$ alkyl. In some embodiments, $L^{am1}$ is $—CH_2—$. In some embodiments, $L^{am2}$ is a covalent bond. In some embodiments, $L^{am2}$ is $—CH_2—$. In some embodiments, both $L^{am1}$ and $L^{am2}$ are $—CH_2—$. In some embodiments, $L^{am1}$ is $—CH_2—$ and $L^{am2}$ is a covalent bond. In some embodiments, —N(R')— is —N(Et)-. In some embodiments, —N(R')— is $—N(CH_2CF_3)—$. In some embodiments, $L^{aa}$ is $\text{-}L^{am1}\text{-}Cy\text{-}L^{am2}\text{-}$, wherein each variable is as described herein. In some embodiments, -Cy- is optionally substituted phenyl. In some embodiments, -Cy- is optionally substituted 5-6 membered heteroaryl having 1-4 heteroatoms.

In some embodiments, a compound is

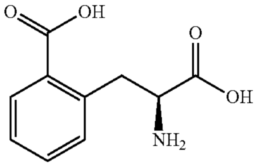 [SMILES: N[C@@H](Cc1ccccc1C(=O)O)C(=O)O]

(2COOHF) or a salt thereof. In some embodiments, a compound is

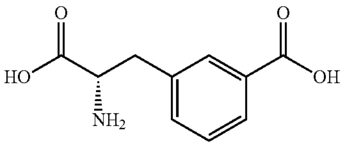 [SMILES: N[C@@H](Cc1cccc(C(=O)O)c1)C(=O)O]

(3COOHF) or a salt thereof. In some embodiments, a compound is

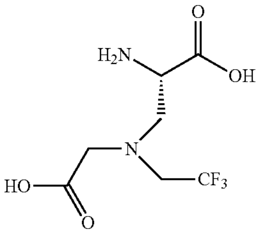 [SMILES: N[C@@H](CN(CC(=O)O)CC(F)(F)F)C(=O)O]

(TfeGA) or a salt thereof. In some embodiments, a compound is

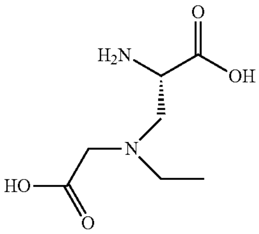

(EtGA) or a salt thereof. In some embodiments, a compound is

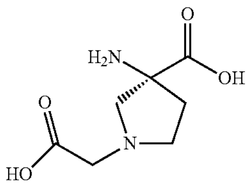 [SMILES: N[C@@]1(C(=O)O)CCN(CC(=O)O)C1]

or a salt thereof. In some embodiments, a compound is

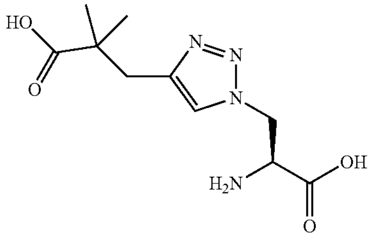 [SMILES: CC(C)(Cc1cn(C[C@H](N)C(=O)O)nn1)C(=O)O]

or a salt thereof. In some embodiments, a compound is

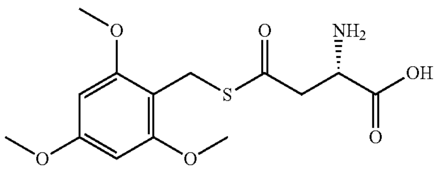 [SMILES: COc1cc(OC)c(CSC(=O)C[C@H](N)C(=O)O)c(OC)c1]

salt thereof. In some embodiments, a compound is

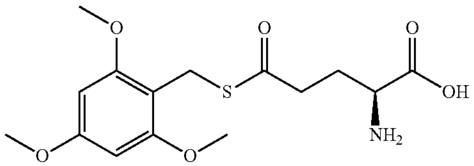 [SMILES: COc1cc(OC)c(CSC(=O)CC[C@H](N)C(=O)O)c(OC)c1]

or a salt thereof. In some embodiments, a compound is

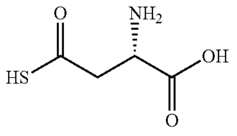

or a salt thereof. In some embodiments, a compound is

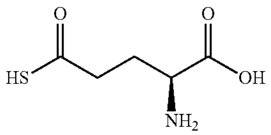

or a salt thereof. Among other things, such compounds may be utilized as amino acid residues in peptides including stapled peptides.

Peptides

Among other things, the present disclosure provides peptides, including stapled peptides, comprising residues of amino acids described herein. In some embodiments, the present disclosure provides various methods comprising utilizing amino acids, optionally protected and/or activated, as described herein. In some embodiments, the present disclosure provides methods for preparing peptides, comprising utilizing amino acids, typically protected and/or activated, as described herein. For example, in some embodiments, various amino groups are Fmoc protected for peptide synthesis (particularly for forming backbone peptide bonds). In some embodiments, various side chain carboxylic acid groups are t-Bu protected (—C(O)—O-tBu).

In some embodiments, the present disclosure provides a compound, e.g., a peptide, comprising a residue of a compound of formula PA or a salt form thereof. In some embodiments, a residue has the structure of —N($R^{a1}$)-$L^{a1}$-C($R^{a2}$)($R^{a3}$)-$L^{a2}$-C(O)— or a salt form thereof, wherein each variable is independently as described herein. In some embodiments, a residue has the structure of —N($R^{a1}$)-$L^{a1}$-C(-$L^{aa}$_COOH)($R^{a3}$)-$L^{a2}$-C(O)— or a salt form thereof, wherein each variable is independently as described herein. For example, in some embodiments, a residue is

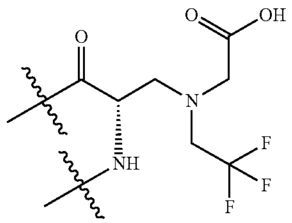 [SMILES: *N[C@@H](CN(CC(=O)O)CC(F)(F)F)C(*)=O]

or a salt form thereof. In some embodiments, a residue is

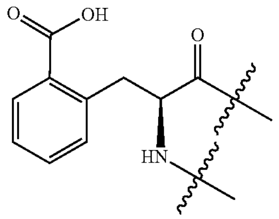 [SMILES: *N[C@@H](Cc1ccccc1C(=O)O)C(*)=O]

or a salt form thereof. In some embodiments, a residue is

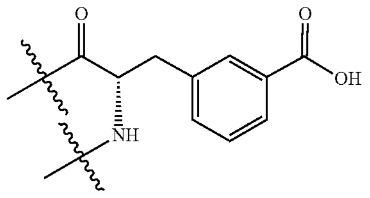 [SMILES: *N[C@@H](Cc1cccc(C(=O)O)c1)C(*)=O]

or a salt form thereof. In some embodiments, a residue is

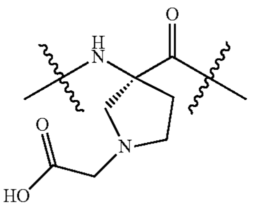 [SMILES: *N[C@@]1(C(*)=O)CCN(CC(=O)O)C1]

or a salt form thereof. In some embodiments, a residue is

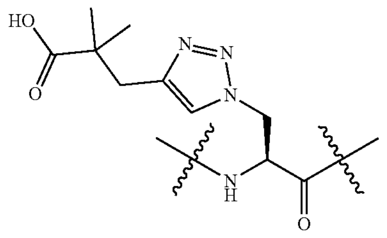 [SMILES: *N[C@@H](Cn1cc(CC(C)(C)C(=O)O)nn1)C(*)=O]

or a salt form thereof. In some embodiments, a residue is

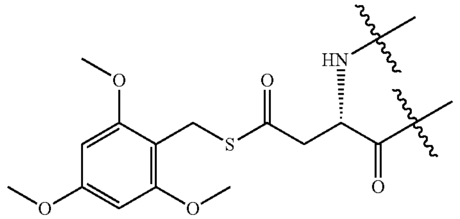 [SMILES: *N[C@@H](CC(=O)SCc1c(OC)cc(OC)cc1OC)C(*)=O]

or a salt form thereof. In some embodiments, a residue is

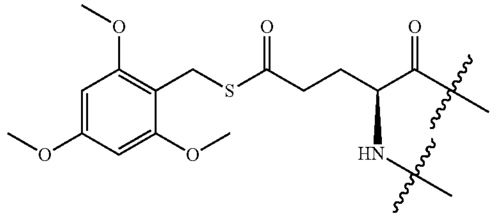 [SMILES: *N[C@@H](CCC(=O)SCc1c(OC)cc(OC)cc1OC)C(*)=O]

or a salt form thereof. In some embodiments, a residue is

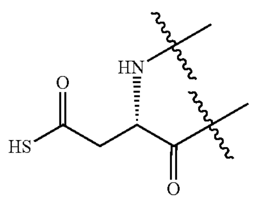 [SMILES: *N[C@@H](CC(=O)S)C(*)=O]

or a salt form thereof. In some embodiments, a residue is

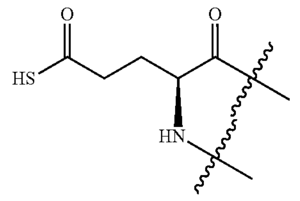 [SMILES: *N[C@@H](CCC(=O)S)C(*)=O]

or a salt form thereof.

In some embodiments, a peptide is a stapled peptide. In some embodiments, a peptide is a stitched peptide. Various technologies for stapled and stitched peptides, including various staples and/or methods for manufacturing are available and may be utilized in accordance with the present disclosure.

Production

Various technologies can be utilized in accordance with the present disclosure to prepare provided compounds. Certain such technologies are described below and in the Examples.

In some embodiments, a provide compound may be prepared using one or more or all steps described below:

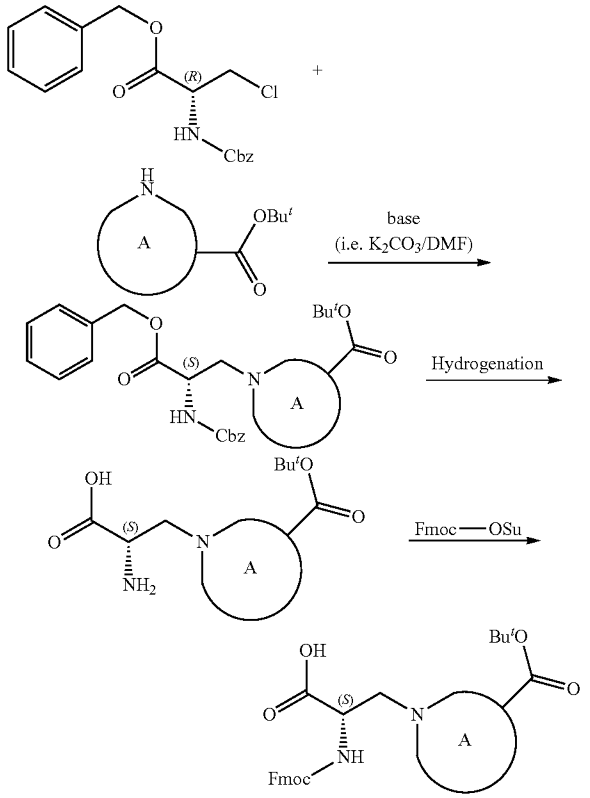

Those skilled in the art will appreciate that other leaving groups can be utilized in place of —Cl for the first reaction, such as —Br, —I, —OTs, Oms, etc.

In some embodiments, a provide compound may be prepared using one or more or all steps described below:

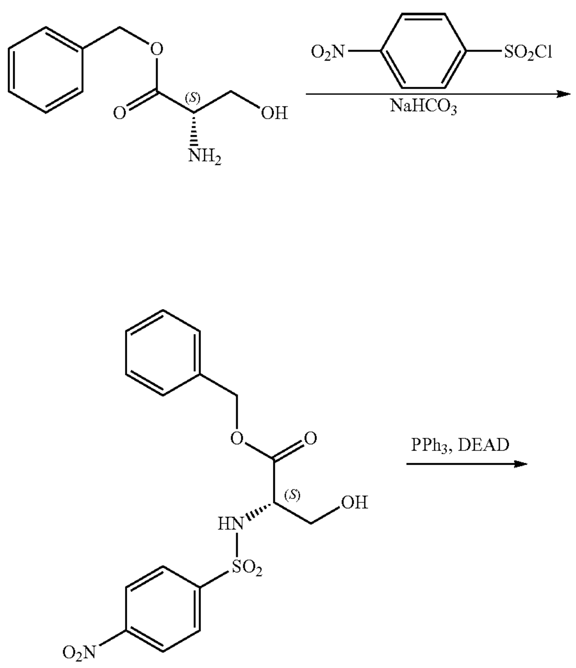
-continued
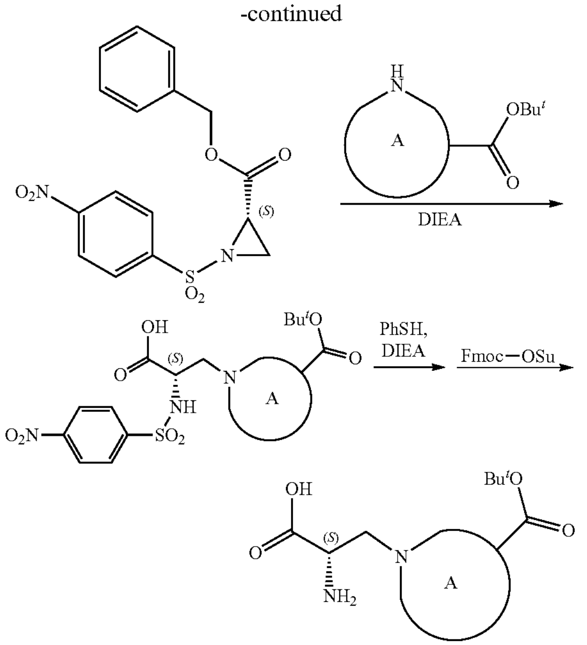
In some embodiments, a provide compound may be prepared using one or more or all steps described below:
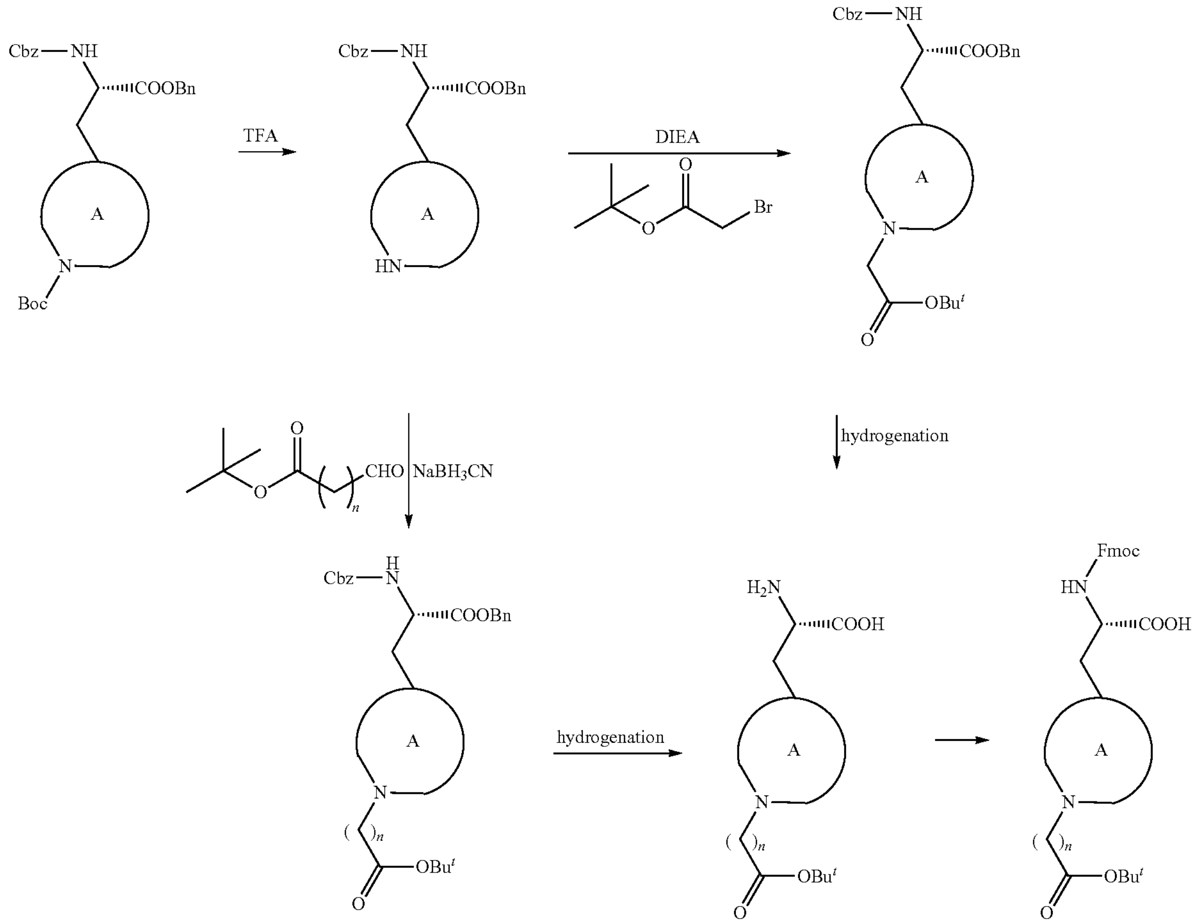

In some embodiments, a provide compound may be prepared using one or more or all steps described below:
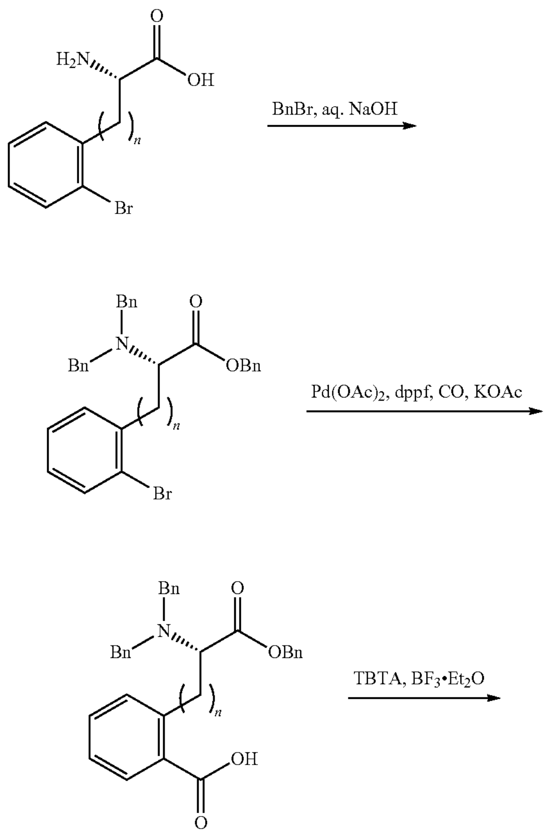
-continued
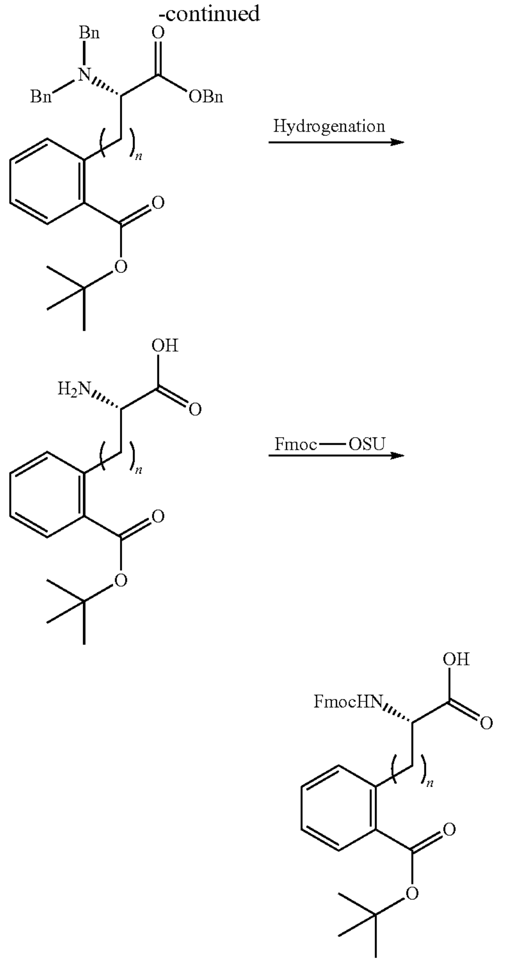
In some embodiments, a provide compound may be prepared using one or more or all steps described below:
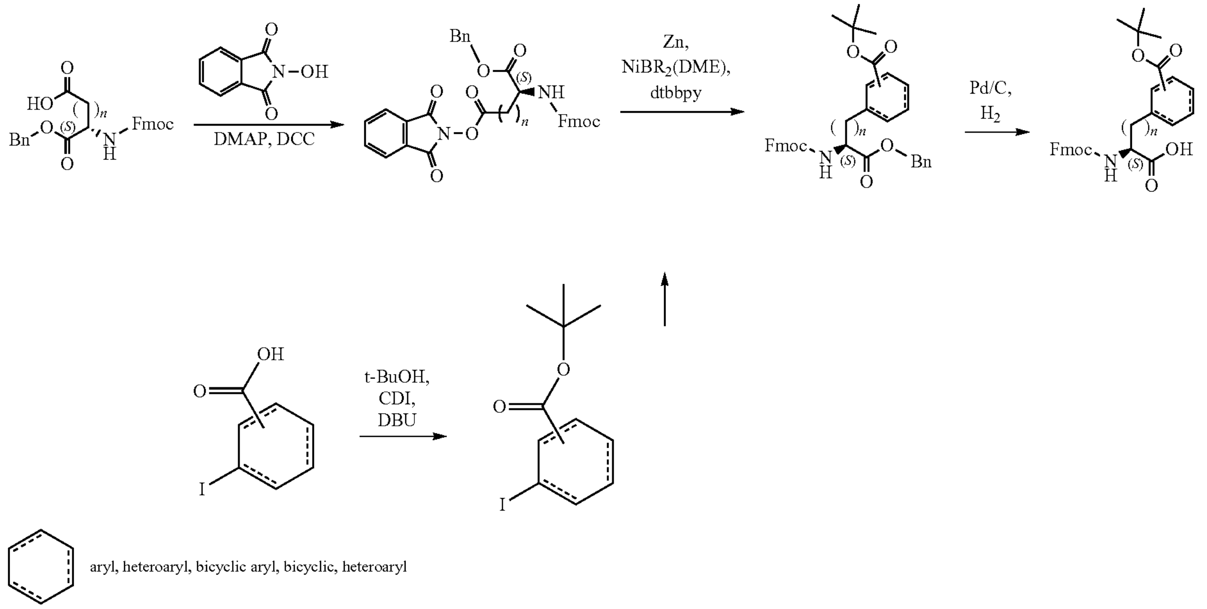

Compounds, e.g., peptides, comprising residues of provided amino acids can be readily manufactured using a variety of technologies in accordance with the present disclosure. For examples, in some embodiments, peptides are prepared through chemical synthesis, e.g., Fmoc-based peptide synthesis optionally utilizing suitable solid phase supports. In some embodiments, preparation of peptides comprises biosynthesis, e.g., incorporation of natural and unnatural amino acids such as those provided herein through biological engineering of suitable organism. In some embodiments, the present methods provides technologies for preparing a product comprising a residue of a provided compound, comprising providing a provided compound and incorporate it to form the product.

Provided compounds can be provided in high purity. In some embodiments, a provided compound is at least about 85%, 90%, 91%, 92%, 93%, 94%, 95%, 96%, 97%, 98%, or 99% pure. In some embodiments, provided compounds, e.g., amino acids optionally protected/activated, are essentially free of impurities, including stereoisomers.

Compositions

In some embodiments, the present disclosure provides compositions comprising provided compounds. In some embodiments, a composition is a pharmaceutical composition. In some embodiments, a composition is a pharmaceutical composition comprising a provided compound, or a pharmaceutically acceptable salt thereof, and a pharmaceutically acceptable carrier. In some embodiments, a composition is a pharmaceutical composition comprising a compound of formula PA, or a pharmaceutically acceptable salt thereof, and a pharmaceutically acceptable carrier. In some embodiments, a composition is a pharmaceutical composition comprising a peptide comprising a residue of a provided amino acid (e.g., a compound of formula PA or a salt thereof), or a pharmaceutically acceptable salt thereof, and a pharmaceutically acceptable carrier.

Uses and Applications

In some embodiments, provided compounds, e.g., those of formula PA or salts thereof, are biologically active and may be utilized in as therapeutic agents. In some embodiments, provided compounds, e.g., amino acids, may be utilized to prepare other products, e.g., biologically active small molecule or peptide products. In some embodiments, the present disclosure provides products comprising residues of provided amino acid compounds, e.g., those of formula PA or salts thereof.

Among other things, provided compounds, e.g., amino acid compounds that have the structure of formula PA or salts thereof, can be utilized to replace certain amino acids, e.g., amino acid comprising acidic side chains such as natural amino acids Asp or Glu, to improve properties and/or activities of products, particularly peptide products, comprising such amino acid residues. In some embodiments, replacement of amino acids such as Asp or Glu with provided amino acids increase lipophilicity. In some embodiments, replacement of amino acids such as Asp or Glu with provided amino acids improves delivery into cells. In some embodiments, replacement of amino acids such as Asp or Glu with provided amino acids does not cause significant undesired impact on other properties/activities, such as solubility, target binding, etc.

Provided compounds comprising residues of amino acid residues, e.g., those of compounds of formula PA, can be utilized for variable applications. In some embodiments, they are biologically active and may be utilized as therapeutics.

Among other things, the present disclosure provides the following embodiments:

1. A compound having the structure of formula PA:

$$N(R^{PA})(R^{a1}) — L^{a1} - C(R^{a2})(R^{a3}) - L^{a2} - C(O)R^{PC}, \qquad \text{PA}$$

or a salt thereof, wherein:

$R^{PA}$ is —H or an amino protecting group;

each of $R^{a1}$ and $R^{a3}$ is independently $-L^a-R'$;

$R^{a2}$ is $-L^{aa}-C(O)R^{PS}$;

each of $L^a$, $L^{a1}$ and $L^{a2}$ is independently L;

$—C(O)R^{PS}$ is optionally protected or activated —COOH;

$—C(O)R^{PC}$ is optionally protected or activated —COOH;

each L is independently a covalent bond, or an optionally substituted, bivalent $C_1$-$C_{25}$ aliphatic or heteroaliphatic group having 1-10 heteroatoms wherein one or more methylene units of the group are optionally and independently replaced with $—C(R')_2—$, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, $—S(O)_2—$, $—S(O)_2N(R')—$, —C(O)S—, or —C(O)O—;

each -Cy- is independently an optionally substituted bivalent, 3-30 membered, monocyclic, bicyclic or polycyclic ring having 0-10 heteroatoms;

each R' is independently —R, —C(O)R, $—CO_2R$, or $—SO_2R$; and each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

2. A compound having the structure of formula PA:

$$N(R^{PA})(R^{a1}) — L^{a1} - C(R^{a2})(R^{a3}) - L^{a2} - C(O)R^{PC}, \qquad \text{PA}$$

or a salt thereof, wherein:

$R^{PA}$ is —H or an amino protecting group;

each of $R^{a1}$ and $R^{a3}$ is independently $-L^a-R'$;

$R^{a2}$ is $-L^{aa}-C(O)R^{PS}$, wherein $L^{aa}$ is L and $L^{aa}$ comprises —N(R')— or -Cy-;

each of $L^a$, $L^{a1}$ and $L^{a2}$ is independently L;

$—C(O)R^{PS}$ is optionally protected or activated —COOH;

—$C(O)R^{PC}$ is optionally protected or activated —COOH;

each L is independently a covalent bond, or an optionally substituted, bivalent $C_1$-$C_{25}$ aliphatic or heteroaliphatic group having 1-10 heteroatoms wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—;

each -Cy- is independently an optionally substituted bivalent, 3-30 membered, monocyclic, bicyclic or polycyclic ring having 0-10 heteroatoms;

each R' is independently —R, —C(O)R, —$CO_2R$, or —$SO_2R$; and each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or.

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

3. The compound of any one of the preceding Embodiments, wherein $L^{a1}$ is a covalent bond.

4. The compound of any one of the preceding Embodiments, wherein $L^{a2}$ is a covalent bond.

5. The compound of any one of the preceding Embodiments, wherein $L^{aa}$ is an optionally substituted, bivalent $C_1$-$C_{25}$ aliphatic or heteroaliphatic group having 1-10 heteroatoms wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—, wherein at least one methylene unit is replaced with -Cy-.

6. The compound of any one of the preceding Embodiments, wherein $L^{aa}$ is -$L^{am1}$-Cy-$L^{am}$- wherein each of $L^{am1}$ and $L^{am2}$ is independently $L^{am}$, wherein each $L^{am}$ is independently a covalent bond, or an optionally substituted, bivalent $C_1$-$C_{10}$ aliphatic group wherein one or more methylene units of the aliphatic group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—.

7. The compound of any one of the preceding Embodiments, wherein -$L^{am2}$- is bonded to —$C(O)R^{PS}$.

8. The compound of any one of the preceding Embodiments, wherein $L^{am2}$ is a covalent bond.

9. The compound of any one of the preceding Embodiments, wherein -Cy- is an optionally substituted 4-7 membered ring having 0-3 heteroatoms.

10. The compound of any one of the preceding Embodiments, wherein -Cy- is an optionally substituted 6-10 membered aryl ring or is an optionally substituted 5-10 membered heteroaryl ring having 1-5 heteroatoms.

11. The compound of any one of the preceding Embodiments, wherein -Cy- is an optionally substituted phenyl ring.

12. The compound of any one of the preceding Embodiments, wherein -Cy- is optionally substituted

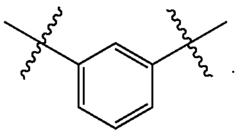 [SMILES: *c1cccc(*)c1]

13. The compound of any one of the preceding Embodiments, wherein -Cy- is

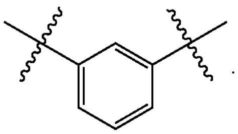 [SMILES: *c1cccc(*)c1]

14. The compound of any one of Embodiments 1-8, wherein -Cy- is optionally substituted

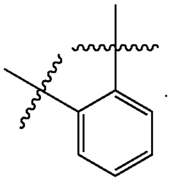 [SMILES: *c1ccccc1*]

15. The compound of any one of Embodiments 1-8, wherein -Cy- is

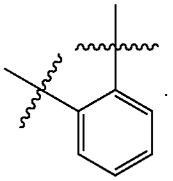 [SMILES: *c1ccccc1*]

16. The compound of any one of Embodiments 1-8, wherein -Cy- is optionally substituted

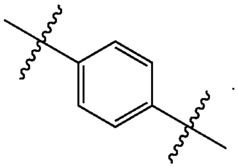 [SMILES: *c1ccc(*)cc1]

17. The compound of any one of Embodiments 1-8, wherein -Cy- is

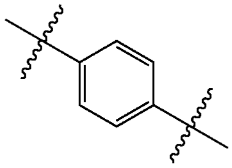

.

18. The compound of any one of Embodiments 1-10, wherein -Cy- is an optionally substituted 5-10 membered heteroaryl ring having 1-5 heteroatoms.
19. The compound of any one of Embodiments 1-10, wherein -Cy- is an optionally substituted 5-membered heteroaryl ring having 1-5 heteroatoms.
20. The compound of any one of Embodiments 1-10, wherein -Cy- is optionally substituted

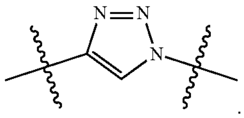 [SMILES: *c1cn(*)nn1]

.

21. The compound of any one of Embodiments 1-10, wherein -Cy- is

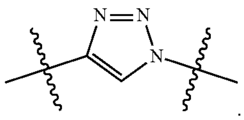 [SMILES: *c1cn(*)nn1]

.

22. The compound of any one of the preceding Embodiments, wherein $L^{aa}$ comprises —N(R')—.
23. The compound of Embodiment 22, wherein $L^{aa}$ is $-L^{am1}$-(NR')-$L^{am2}$-, wherein each of $L^{am1}$ and $L^{am2}$ is independently $L^{am}$, wherein each $L^{am}$ is independently a covalent bond, or an optionally substituted, bivalent $C_1$-$C_{10}$ aliphatic group wherein one or more methylene units of the aliphatic group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2$N(R')—, —C(O)S—, or —C(O)O—.
24. The compound of any one of Embodiments 22-23, wherein R' of the —N(R')— is taken together with $R^{a3}$ and their intervening atoms to form an optionally substituted 3-10 membered ring having 0-5 heteroatoms in addition to the intervening atoms.
25. The compound of any one of Embodiments 22-23, wherein —N(R')— is bonded to two carbon atoms which two carbon atoms do not form any double bonds with heteroatoms.
26. The compound of any one of Embodiments 22-25, wherein $-L^{am2}$- is bonded to —C(O)$R^{PS}$.
27. The compound of any one of Embodiments 22-26, wherein $L^{am1}$ is optionally substituted $C_{1-4}$ alkylene.
28. The compound of any one of Embodiments 22-26, wherein $L^{am1}$ is optionally substituted —$(CH_2)$m-, wherein m is 1, 2, 3, or 4.
29. The compound of any one of Embodiments 22-26, wherein $L^{am1}$ is optionally substituted —$CH_2$—.
30. The compound of any one of Embodiments 22-26, wherein $L^{am1}$ is —$CH_2$—.
31. The compound of any one of Embodiments 22-30, wherein $L^{am2}$ is optionally substituted linear $C_{1-2}$ alkylene.
32. The compound of any one of Embodiments 22-30, wherein $L^{am2}$ is —$[C(R')_2]$n, wherein n is 1 or 2.
33. The compound of any one of Embodiments 22-30, wherein $L^{am2}$ is —[CHR']n, wherein n is 1 or 2.
34. The compound of any one of Embodiments 32-33, wherein each R' is independently —H or optionally substituted $C_{1-6}$ alkyl.
35. The compound of any one of Embodiments 22-30, wherein $L^{am2}$ is optionally substituted —$CH_2$—.
36. The compound of any one of Embodiments 22-35, wherein $L^{am2}$ is —$CH_2$—.
37. The compound of any one of Embodiments 22-36, wherein $L^{aa}$ comprises —N(R')—, wherein R' of the —N(R')— is —$R^{NR}$, wherein $R^{NR}$ is R.
38. The compound of any one of Embodiments 22-36, wherein $L^{aa}$ comprises —N(R')—, wherein R' of the —N(R')— is —$CH_2$—$R^{NR}$, wherein $R^{NR}$ is R.
39. The compound of any one of Embodiments 22-36, wherein $L^{aa}$ comprises —N(R')—, wherein R' of the —N(R')— is —C(O)$R^{NR}$, wherein $R^{NR}$ is R.
40. The compound of any one of Embodiments 22-36, wherein $L^{aa}$ comprises —N(R')—, wherein R' of the —N(R')— is —$SO_2R^{NR}$, wherein $R^{NR}$ is R.
41. The compound of any one of Embodiments 37-40, wherein $R^N$ is optionally substituted $C_{1-6}$ aliphatic or heteroaliphatic having 1-4 heteroatoms.
42. The compound of any one of Embodiments 37-41, wherein $R^{NR}$ is $C_{1-7}$ alkyl or heteroalkyl having 1-4 heteroatoms, wherein the alkyl or heteroalkyl is optionally substituted with one or more groups independently selected from halogen, a $C_{5-6}$ aromatic ring having 0-4 heteroatoms, and an optionally substituted 3-10 membered cycloalkyl or heteroalkyl ring having 1-4 heteroatoms.
43. The compound of any one of Embodiments 37-42, wherein $R^{NR}$ is —$CF_3$.
44. The compound of any one of Embodiments 37-41, wherein $L^{am2}$ is or comprises —$C(R')_2$— wherein the R' group and R' in —N(R')— of $L^{aa}$ are taken together with their intervening atoms to form an optionally substituted, 3-30 membered, monocyclic, bicyclic or polycyclic ring having, in addition to the intervening atoms, 0-10 heteroatoms.
45. The compound of any one of Embodiments 1-5, wherein $L^{aa}$ is optionally substituted $C_{1-4}$ alkylene.
46. The compound of Embodiment 45, wherein $L^{aa}$ is optionally substituted —$CH_2$—$CH_2$—.
47. The compound of Embodiment 45, wherein $L^{aa}$ is optionally substituted —$CH_2$—.
48. The compound of Embodiment 1, having the structure of

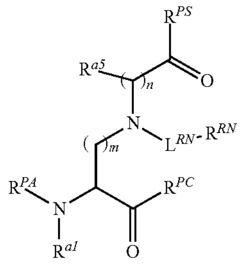

or a salt thereof, wherein:

each of m and n is independently 1, 2, 3, or 4;

$L^{RN}$ is L;

$R^{RN}$ is R; and $R^{a5}$ is R'.

49. The compound of Embodiment 48, wherein m is 1.

50. The compound of any one of Embodiments 48-49, wherein $L^{RN}$ is —$CH_2$—, —CO—, or —$SO_2$—.

51. The compound of any one of Embodiments 48-49, wherein $L^{RN}$ is —$CH_2$—.

52. The compound of any one of Embodiments 48-51, wherein $R^{NR}$ is $C_{1-7}$ alkyl or heteroalkyl having 1-4 heteroatoms, wherein the alkyl or heteroalkyl is optionally substituted with one or more groups independently selected from halogen, a $C_{5-6}$ aromatic ring having 0-4 heteroatoms, and an optionally substituted 3-10 membered cycloalkyl or heteroalkyl ring having 1-4 heteroatoms.

53. The compound of any one of Embodiments 48-52, wherein one or more $R^{a5}$ are independently —H.

54. The compound of any one of Embodiments 48-53, wherein one or more $R^{a5}$ are independently optionally substituted $C_{1-6}$ alkyl.

55. The compound of any one of Embodiments 48-53, wherein -$L^{RN}$-$R^{RN}$ is R, and is taken together with a $R^{a5}$ and their intervening atoms to form an optionally substituted, 3-30 membered, monocyclic, bicyclic or polycyclic ring having, in addition to the intervening atoms, 0-10 heteroatoms.

56. The compound of Embodiment 51, wherein $R^{RN}$ is methyl.

57. The compound of Embodiment 51, wherein $R^{RN}$ is —$CF_3$.

58. The compound of any one of the preceding Embodiments, wherein $R^{a1}$ is —H.

59. The compound of any one of Embodiments 1-44, wherein $R^{a1}$ is optionally substituted $C_{1-6}$ alkyl.

60. The compound of Embodiment 1, wherein the compound has the structure of

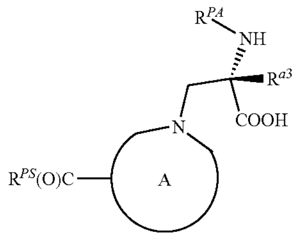

or a salt thereof, wherein Ring A is an optionally substituted 3-7 membered saturated, partially unsaturated or aromatic ring.

61. The compound of Embodiment 1, wherein the compound has the structure of

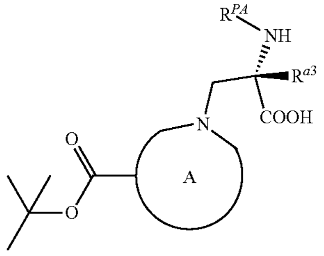

or a salt thereof, wherein Ring A is an optionally substituted 3-7 membered saturated, partially unsaturated or aromatic ring.

62. The compound of any one of Embodiment 60 or 61, wherein —C(O)OtBu is bonded to a chiral carbon atom having a R configuration.

63. The compound of any one of Embodiment 60 or 61, wherein —C(O)OtBu is bonded to a chiral carbon atom having a S configuration.

64. The compound of Embodiment 1, wherein the compound has the structure of

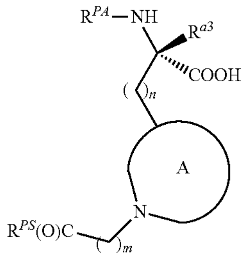

or a salt thereof, wherein:

Ring A is an optionally substituted 3-10 membered ring;

n is 0, 1, or 2; and m is 0, 1, 2, or 3.

65. The compound of Embodiment 1, wherein the compound has the structure of

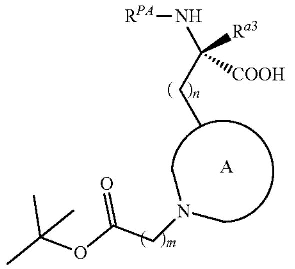

or a salt thereof, wherein:

Ring A is an optionally substituted 3-10 membered ring;

n is 0, 1, or 2; and m is 0, 1, 2, or 3.

66. The compound of any one of Embodiments 64-65, wherein Ring A is an optionally substituted 4-10 membered ring.

67. The compound of any one of Embodiments 64-66, wherein n is 1.
68. The compound of any one of Embodiments 64-67, wherein Ring A is bonded to —$(CH_2)$n- at a chiral carbon which is R.
69. The compound of any one of Embodiments 64-67, wherein Ring A is bonded to —$(CH_2)$n- at a chiral carbon which is S.
70. The compound of Embodiment 1, wherein the compound has the structure of

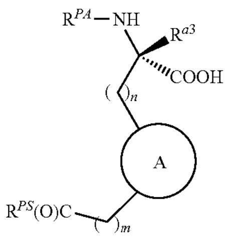

or a salt thereof, wherein:

Ring A is an optionally substituted 3-10 membered ring;

n is 0, 1, or 2; and m is 0, 1, 2, or 3.

71. The compound of Embodiment 1, wherein the compound has the structure of

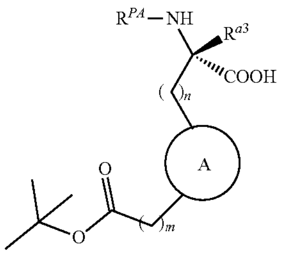

or a salt thereof, wherein:

Ring A is an optionally substituted 3-10 membered ring;

n is 0, 1, or 2; and m is 0, 1, 2, or 3.

72. The compound of Embodiment 1, wherein the compound has the structure of

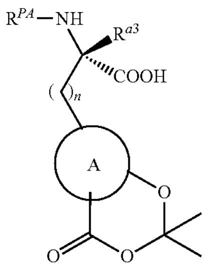

or a salt thereof, wherein:

Ring A is an optionally substituted 3-10 membered ring; and n is 0, 1, or 2.

73. The compound of any one of Embodiments 64-72, wherein n is 1.
74. The compound of any one of Embodiments 64-73, wherein m is 0.
75. The compound of any one of Embodiments 64-73, wherein m is 1, 2, and 3.
76. The compound of any one of Embodiments 64-73, wherein m is 1.
77. The compound of any one of Embodiments 64-76, wherein Ring A is or comprises an optionally substituted saturated monocyclic ring.
78. The compound of any one of Embodiments 64-77, wherein Ring A is or comprises an optionally substituted partially unsaturated monocyclic ring.
79. The compound of any one of Embodiments 64-78, wherein Ring A is or comprises an optionally substituted aromatic monocyclic ring.
80. The compound of any one of Embodiments 70-76, wherein Ring A is optionally substituted phenyl.
81. The compound of any one of Embodiments 64-76, wherein Ring A is optionally substituted 5-6 membered heteroaryl having 1-3 heteroatoms.
82. The compound of any one of Embodiments 64-76, wherein Ring A is optionally substituted 5-6 membered heteroaryl having 1-3 heteroatoms, wherein at least one heteroatom is nitrogen.
83. The compound of Embodiment 82, wherein Ring A is an optionally substituted triazole ring.
84. The compound of any one of Embodiments 64-76, wherein Ring A is an optionally substituted 8-10 membered bicyclic ring having 1-6 heteroatoms.
85. The compound of any one of Embodiments 64-67, wherein Ring A is an optionally substituted 8-10 membered bicyclic aromatic ring having 1-6 heteroatoms, wherein each monocyclic unit is independently an optionally 5-6 membered aromatic ring having 0-3 heteroatoms.
86. The compound of any one of Embodiments 81-85, wherein Ring A is bonded to —$(CH_2)$n- at a carbon atom.
87. The compound of any one of Embodiments 81-85, wherein Ring A is bonded to —$(CH_2)$n- at a nitrogen atom.
88. The compound of any one of the preceding Embodiments, wherein Ring A or -Cy- in $L^{aa}$ is optionally substituted, and each substitute is independently selected from halogen, —R, —$CF_3$, —$N(R)_2$, —CN, and —OR, wherein each R is independently $C_{1-6}$ aliphatic optionally substituted with one or more —F.
89. The compound of any one of the preceding Embodiments, wherein Ring A or -Cy- in $L^{aa}$ is optionally substituted, and each substitute is independently selected from halogen, $C_{1-5}$ linear, branched or cyclic alkyl, —OR wherein R is $C_{1-4}$ linear, branched or cyclic alkyl, fluorinated alkyl, —$N(R)_2$ wherein each R is independently $C_{1-6}$ linear, branched or cyclic alkyl, or —CN.
90. The compound of any one of the preceding Embodiments, wherein $R^{a3}$ is —H or optionally substituted $C_{1-6}$ aliphatic.
91. The compound of any one of the preceding Embodiments, wherein $R^{a3}$ is —H.
92. The compound of any one of Embodiments 1-90, wherein $R^{a3}$ is methyl.

93. A compound having the structure of:

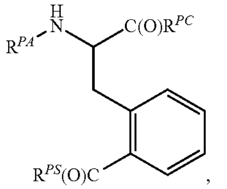

or a salt thereof, wherein:

$R^{PA}$ is —H or an amino protecting group;

—C(O)$R^{PS}$ is optionally protected or activated —COOH; and

—C(O)$R^{PC}$ is optionally protected or activated —COOH.

94. A compound having the structure of:

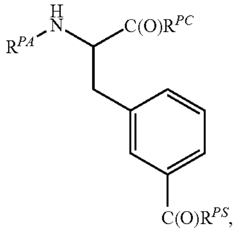

or a salt thereof, wherein:

$R^{PA}$ is —H or an amino protecting group;

—C(O)$R^{PS}$ is optionally protected or activated —COOH; and

—C(O)$R^{PC}$ is optionally protected or activated —COOH.

95. The compound of any one of the preceding Embodiments, wherein $R^{A}$ is an amino protecting group suitable for peptide synthesis.

96. The compound of any one of the preceding Embodiments, wherein $R^{A}$ is —C(O)—O—R.

97. The compound of Embodiment 96, wherein R is optionally substituted

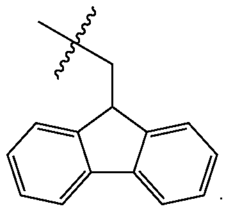 [SMILES: *CC1c2ccccc2-c2ccccc21]

98. The compound of any one of the preceding Embodiments, wherein $R^{PA}$ is -Fmoc.

99. The compound of any one of the preceding Embodiments, wherein $R^{PA}$ is -Cbz.

100. The compound of any one of the preceding Embodiments, wherein $R^{PA}$ is -Boc.

101. The compound of any one of the preceding Embodiments, wherein $R^{PS}$ is a protecting group orthogonal to $R^{PA}$.

102. The compound of any one of the preceding Embodiments, wherein $R^{PS}$ is a protecting group orthogonal to $R^{PC}$.

103. The compound of any one of the preceding Embodiments, wherein $R^{PS}$ is compatible with peptide synthesis.

104. The compound of any one of the preceding Embodiments, wherein —C(O)$R^{PS}$ is —C(O)OR'.

105. The compound of Embodiment 104, wherein R' is —H.

106. The compound of Embodiment 104, wherein R' is optionally substituted $C_{1-6}$ aliphatic.

107. The compound of Embodiment 104, wherein R' is t-butyl.

108. The compound of Embodiment 104, wherein R' is benzyl.

109. The compound of Embodiment 104, wherein R' is allyl.

110. The compound of any one of Embodiments 1-103, wherein —C(O)$R^{PS}$ is —C(O)S-L-R'.

111. The compound of Embodiment 110, wherein L is optionally substituted —$CH_2$—.

112. The compound of Embodiment 110, wherein L is —$CH_2$—.

113. The compound of any one of Embodiments 110-112, wherein R' is optionally substituted phenyl.

114. The compound of any one of Embodiments 110-112, wherein R' is 2, 4, 6-trimethoxyphenyl.

115. The compound of Embodiment 110, wherein $R^{PS}$ is —SH.

116. The compound of any one of the preceding Embodiments, wherein —C(O)$R^{PC}$ is a protected carboxylic acid group.

117. The compound of any one of Embodiments 1-114, wherein —C(O)$R^{PC}$ is an activated carboxylic acid group.

118. The compound of any one of Embodiments 1-114, wherein —C(O)$R^{PC}$ is —C(O)OR'.

119. The compound of Embodiment 118, wherein R' is —H.

120. The compound of Embodiment 118, wherein R' is pentafluorophenyl.

121. The compound of Embodiment 118, wherein R' is

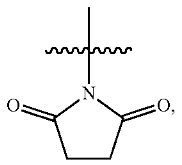 [SMILES: *N1C(=O)CCC1=O]

122. The compound of any one of the preceding Embodiments, wherein each heteroatom is independently selected from oxygen, nitrogen, sulfur, phosphorus and silicon.

123. The compound of any one of the preceding Embodiments, wherein each heteroatom is independently selected from oxygen, nitrogen, and sulfur.

124. A compound, wherein the compound is

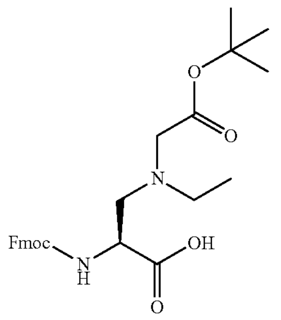

or a salt thereof.

125. A compound, wherein the compound is

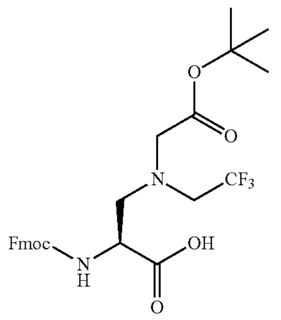

or a salt thereof.

126. A compound, wherein the compound is

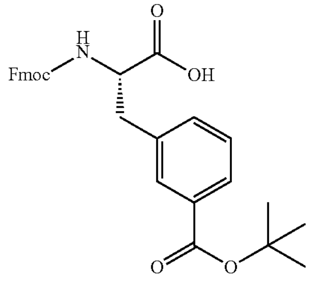

or a salt thereof.

127. A compound, wherein the compound is

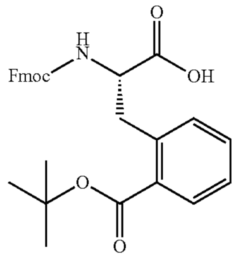

or a salt thereof.

128. A compound, wherein the compound is

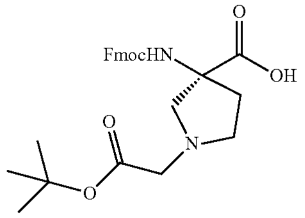

or a salt thereof.

129. A compound, wherein the compound is

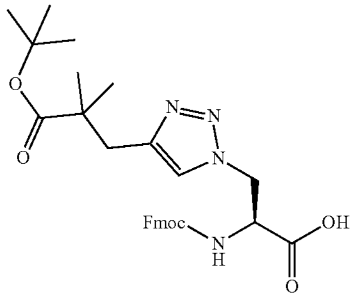

or a salt thereof.

130. A compound, wherein the compound is

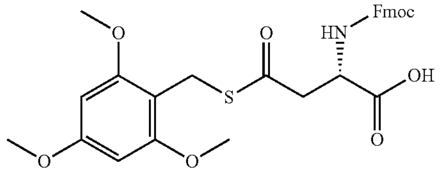

or a salt thereof.

131. A compound, wherein the compound is

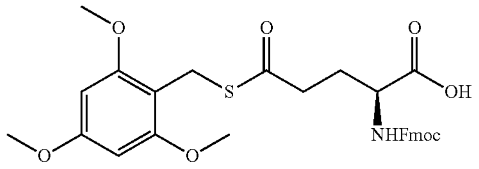

or a salt thereof.

132. A compound, wherein the compound is

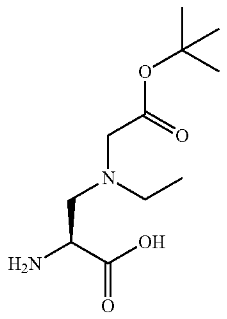 [SMILES: CCN(CC(=O)OC(C)(C)C)C[C@H](N)C(=O)O]

or a salt thereof.

133. A compound, wherein the compound is

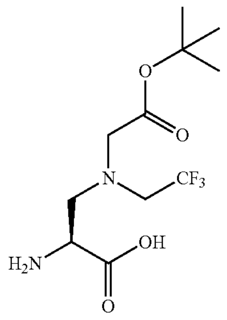 [SMILES: CC(C)(C)OC(=O)CN(C[C@H](N)C(=O)O)CC(F)(F)F]

or a salt thereof.

134. A compound, wherein the compound is

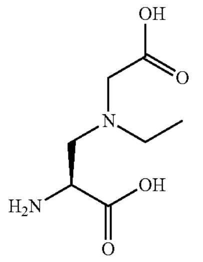

or a salt thereof.

135. A compound, wherein the compound is

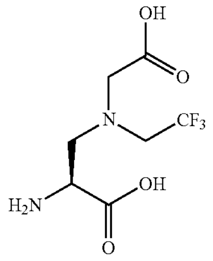 [SMILES: N[C@@H](CN(CC(=O)O)CC(F)(F)F)C(=O)O]

or a salt thereof.

136. A compound, wherein the compound is

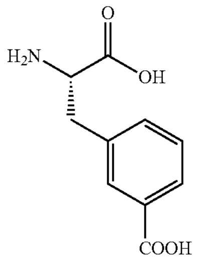 [SMILES: N[C@@H](Cc1cccc(C(=O)O)c1)C(=O)O]

or a salt thereof.

137. A compound, wherein the compound is

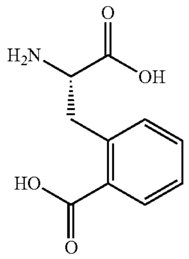 [SMILES: N[C@@H](Cc1ccccc1C(=O)O)C(=O)O]

or a salt thereof.

138. A compound, wherein the compound is

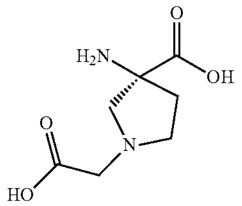 [SMILES: N[C@@]1(C(=O)O)CCN(CC(=O)O)C1]

or a salt thereof.

139. A compound, wherein the compound is

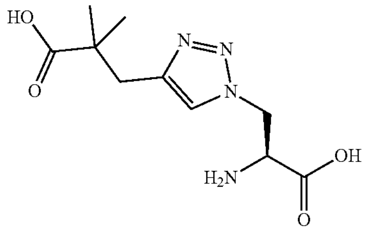 [SMILES: CC(C)(Cc1cn(C[C@H](N)C(=O)O)nn1)C(=O)O]

or a salt thereof.

140. A compound, wherein the compound is

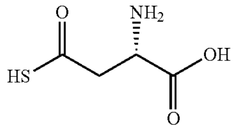

or a salt thereof.

141. A compound, wherein the compound is

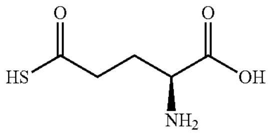

or a salt thereof.

142. A compound, wherein the compound is

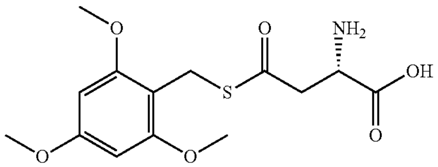 [SMILES: COc1cc(OC)c(CSC(=O)C[C@H](N)C(=O)O)c(OC)c1]

or a salt thereof.

143. A compound, wherein the compound is

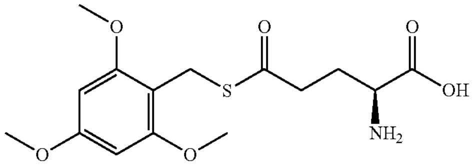 [SMILES: COc1cc(OC)c(CSC(=O)CC[C@H](N)C(=O)O)c(OC)c1]

or a salt thereof.

144. The compound of any one of the preceding Embodiments, wherein the compound has a purity of at least about 90%, 91%, 92%, 93%, 94%, 95%, 96%, 97%, 98%, or 99%.

145. A compound, comprising a residue of any one of the preceding Embodiments.

146. A compound, comprising a residue having the structure of

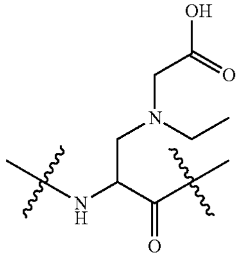 [SMILES: *NC(CN(CC)CC(=O)O)C(*)=O]

or a salt form thereof.

147. A compound, comprising a residue having the structure of

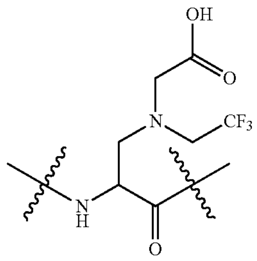 [SMILES: *NC(CN(CC(=O)O)CC(F)(F)F)C(*)=O]

or a salt form thereof.

148. A compound, comprising a residue having the structure of

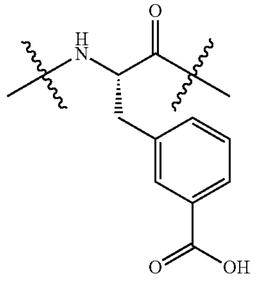 [SMILES: *N[C@@H](Cc1cccc(C(=O)O)c1)C(*)=O]

or a salt form thereof.

149. A compound, comprising a residue having the structure of

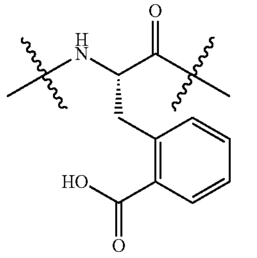 [SMILES: *N[C@@H](Cc1ccccc1C(=O)O)C(*)=O]

or a salt form thereof.

150. A compound, comprising a residue having the structure of

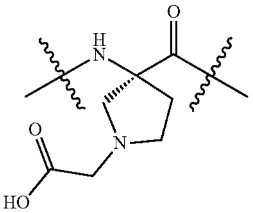 [SMILES: *N[C@@]1(C(*)=O)CCN(CC(=O)O)C1]

or a salt form thereof.

151. A compound, comprising a residue having the structure of

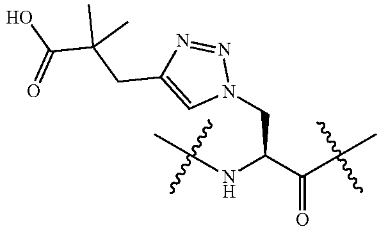 [SMILES: *N[C@@H](Cn1cc(CC(C)(C)C(=O)O)nn1)C(*)=O]

or a salt form thereof.

152. A compound, comprising a residue having the structure of

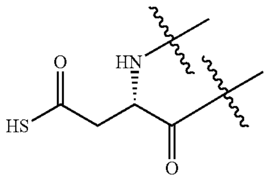 [SMILES: *N[C@@H](CC(=O)S)C(*)=O]

or a salt form thereof.

153. A compound, comprising a residue having the structure of

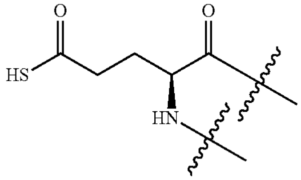 [SMILES: *N[C@@H](CCC(=O)S)C(*)=O]

or a salt form thereof.

154. A compound, comprising a residue having the structure of

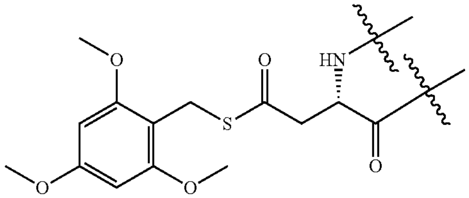 [SMILES: *N[C@@H](CC(=O)SCc1c(OC)cc(OC)cc1OC)C(*)=O]

or a salt form thereof.

155. A compound, comprising a residue having the structure of

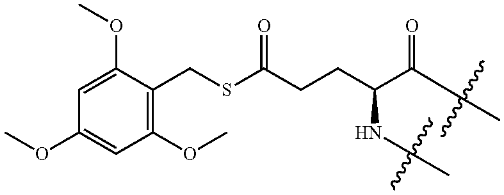 [SMILES: *N[C@@H](CCC(=O)SCc1c(OC)cc(OC)cc1OC)C(*)=O]

or a salt form thereof.

156. The compound of any one of Embodiments 145-155, wherein the compound is or comprise a peptide.

157. The compound of any one of Embodiments 145-155, wherein the compound is or comprise a stapled peptide.

158. A method for preparing a compound of any one of Embodiments 145-157, comprising utilization of a compound of any one of the Embodiments 1-144.

EXEMPLIFICATION

Those skilled in the art appreciate that various technologies are available for manufacturing and assessing provided technologies (amino acids, peptides, etc.) in accordance with the present disclosure, for example, many technologies for preparing small molecules and peptides can be utilized to prepare provided agents, and various assays are available for assessing properties and/or activities of provided agents. Described below are certain such useful technologies.

Example 1. Synthesis of (S)-2-((((9H-fluoren-9-yl)methoxy)carbonyl)amino)-3-(2-(tert-butoxycarbonyl)phenyl)propanoic acid

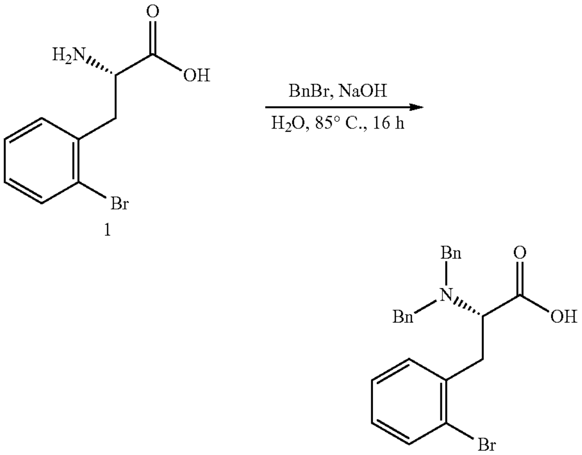

1

2

To a solution of compound 1 in $H_2O$ (250 mL) was added NaOH (84.0 g, 2.10 mol, 5.13 eq) and BnBr (328 g, 1.92 mol, 228 mL, 4.69 eq). The mixture was stirred at 85° C. for 16 hrs. LC-MS (EW24702-4-P1A) showed the compound 1 was consumed completely, and desired mass was detected ($R_t$=1.211 min). The mixture was cooled to 40° C. and the aqueous layer was removed. EtOAc (600 mL) and a mixture of methanol and water (1: 2, 300 mL) were added. The mixture was washed with $H_2O$ (300 mL). The organic layer was dried over $Na_2SO_4$, filtered and concentrated in vacuum. The residue was purified by column chromatography ($SiO_2$, Petroleum ether/Ethyl acetate=1/0, Petroleum ether: Ethyl acetate=10:1, $R_f$=0.7). Compound 2 (206 g, 400 mmol, 97.7% yield) was obtained as yellow oil. LCMS: $R_t$=1.211 min, m/z=514.3.1 $(M+1)^+$. $^1$HNMR ($CDCl_3$, 400 MHz) δ: 7.61 (dd, $J_1$=1.2 Hz, $J_2$=7.6 Hz, 1H), 7.92-7.87 (m, 5H), 7.77-7.66 (m, 11H), 7.64-7.59 (m, 2H), 5.81-5.63 (m, 2H), 4.48 (d, J=14 Hz, 2H), 4.41 (t, J=7.6 Hz, 1H), 4.07 (d, J=14 Hz, 2H), 3.74-3.69 (m, 2H).

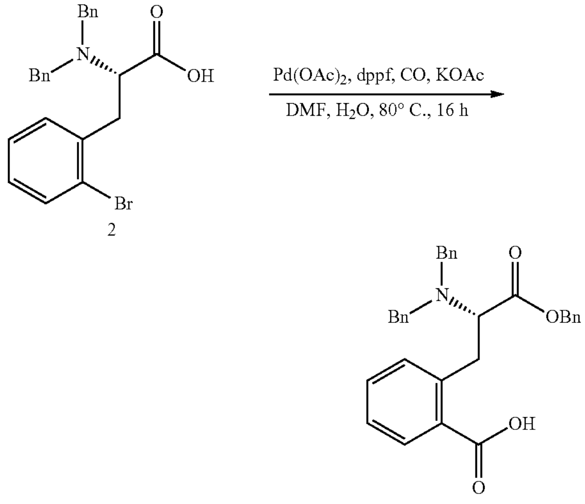

2

3

A mixture of compound 2 (50.0 g, 97.1 mmol, 1.00 eq), $Pd(OAc)_2$ (1.09 g, 4.86 mmol, 0.05 eq), DPPF (5.39 g, 9.72 mmol, 0.1 eq) and KOAc (14.5 g, 147 mmol, 1.52 eq) in DMF (400 mL) and $H_2O$ (100 mL) was degassed and purged with CO for 3 times, and then the mixture was stirred at 80° C. for 16 hrs under CO (50 psi) atmosphere. LC-MS (EW24702-5-P1A) showed the compound 2 wasn't consumed completely, and desired mass was detected ($R_t$=1.068 min). The reaction mixture was filtered. The filtrated was extracted with EtOAc (150 mL*3). The combined organic layers were washed with saturated brine (150 mL*3), dried over $Na_2SO_4$, filtered and concentrated under reduced pressure to give a residue. The crude product was purified by reversed-phase HPLC (FA condition). Compound 3 was obtained as yellow oil. LCMS: $R_t$=1.068 min, m/z=480.3 $(M+1)^+$. $^1$HNMR (CDCl3, 400 MHz) δ: 7.61 (dd, $J_1$=1.2 Hz, $J_2$=7.6 Hz, 1H), 7.44-7.39 (m, 8H), 7.20-7.10 (m, 11H), 5.29 (d, J=12.4 Hz 1H), 5.13 (d, J=12.4 Hz, 1H), 3.96 (d, J=13.6 Hz, 2H), 3.90-3.86 (m, 1H), 3.60-3.57 (m, 2H), 3.48-3.43 (m, 2H).

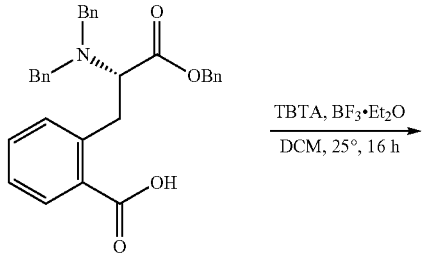

3

-continued

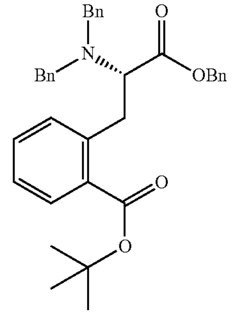

4

To a solution of compound 3 (23.0 g, 47.9 mmol, 1.00 eq) in THF (300 mL) was added TBTA (52.4 g, 239 mmol, 42.9 mL, 5.00 eq), $BF_3{\cdot}Et_2O$ (680 mg, 4.80 mmol, 591 uL, 0.1 eq), the mixture was stirred at 25° C. for 3 hrs. LC-MS (EW24702-8-P1A) showed the compound 3 was consumed completely, and desired mass was detected ($R_f$=1.279 min). The reaction mixture was quenched by addition citric acid 100 mL and extracted with EtOAc (200 mL*3). The combined organic layers were washed with saturated brine (200 mL*3), dried over $Na_2SO_4$, filtered and concentrated under reduced pressure to give a residue. The residue was purified by column chromatography ($SiO_2$, Petroleum ether/Ethyl acetate=1/0 to 10/1, Petroleum ether: Ethyl acetate=10/1, $R_f$=0.4). Compound 4 (25.0 g, 46.6 mmol, 97.3% yield) was obtained as colorless oil. LCMS: EW24702-8-P1A, $R_t$=1.279 min, m/z=536.5 $(M+1)^+$. $^1$HNMR ($CDCl_3$, 400 MHz) δ: 7.85 (dd, $J_1$=0.8 Hz, $J_2$=1.2 Hz, 1H), 7.42-7.29 (m, 7H), 7.17-7.14 (m, 7H), 7.05-7.03 (m, 4H), 5.28 (d, J=12.4 Hz, 1H), 5.16 (d, J=12.4 Hz, 1H), 3.96 (d, J=13.2 Hz, 2H), 3.85-3.81 (m, 1H), 3.61-3.56 (m, 1H), 3.51 (d, J=14 Hz, 2H), 3.34-3.28 (m, 1H), 1.35 (s, 9H). Chiral SFC: Column: Chiralcel OJ-3 50×4.6 mm I.D., 3 um. Mobile phase: Phase A for $CO_2$, and Phase B for MeOH (0.05% DEA); Gradient elution: MeOH (0.05% DEA) in $CO_2$ from 5% to 40%; Flow rate: 3 mL/min; Detector: PDA; Column Temp: 35° C.; Back Pressure: 100 Bar; Chiral purity: 100%.

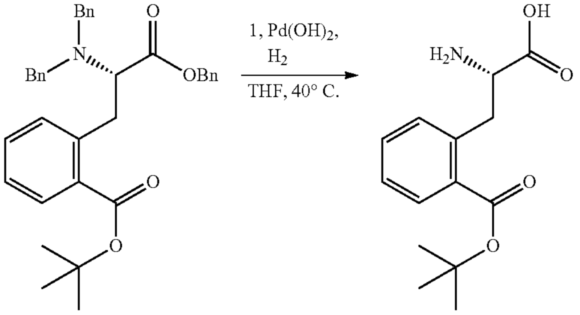

4

5

Two batches were combined together. A mixture of compound 4 (25.0 g, 46.6 mmol, 1.00 eq) and $Pd(OH)_2$ (3.00 g, 4.27 mmol, 20.0% purity, $9.15e^{-2}$ eq) in THF (750 mL) was degassed and purged with $H_2$ for 3 times. The mixture was stirred at 40° C. for 16 hrs under $H_2$ atmosphere (50 psi). LC-MS (EW24072-13-P1C) showed the compound 4 was consumed, desired mass was detected ($R_t$=0.740 min). The mixture was filtered, and the filtrated was used to the next reaction directly. LCMS $R_t$=0.740 min, m/z=210.1 $(M-55)^+$.

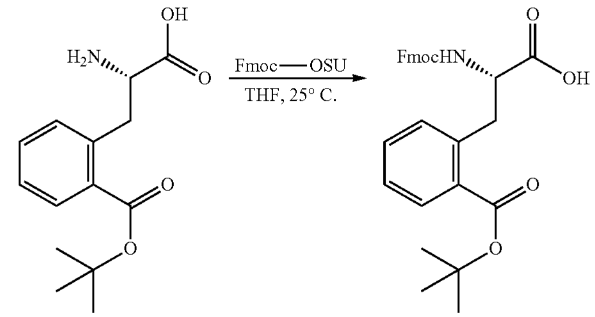

5

A mixture of compound 5 (dissolved in THF), FMOC-OSU (11.1 g, 33.1 mmol, 0.8 eq) in THF (50.0 mL) was degassed and purged with $N_2$ for 3 times, and then the mixture was stirred at 25° C. for 12 hrs. LC-MS (EW24702-14-P1A) showed the compound 5 was consumed completely, and desired mass was detected ($R_t$=0.998 min). The mixture was filtered, and filtrated was concentrated under vacuum. Three batches were combined together. The mixture was purified with reversed-phase HPLC (TFA condition). 2COOHF (13.2 g, 19.1 mmol, 46.2% yield, 98.3% purity) was obtained as yellow solid. LCMS $R_t$=0.983 min, m/z=510.2 $(M+23)^+$; HPLC $R_t$=3.49 min, purity: 98.3%. $^1$HNMR (DMSO, 400 MHz) δ: 12.7 (s, 1H), 7.87 (d, J=7.6 Hz, 2H), 7.76-7.68 (m, 2H), 7.63-7.59 (m, 2H), 7.42-7.40 (m, 2H), 7.38-7.34 (m, 2H), 7.32-7.30 (m, 2H), 7.29-7.26 (m, 2H), 4.31-4.29 (m, 1H), 4.21-4.15 (m, 2H), 4.13-4.10 (m, 1H), 3.54 (d, J=5.2 Hz, 1H), 3.00-2.96 (m, 1H), 1.54 (s, 9H). Chiral SFC: Chiral purity: 100%; Column: Chiralcel OJ-3 50×4.6 mm I.D., 3 um; Mobile phase: Phase A for $CO_2$, and Phase B for MeOH (0.05% DEA); Gradient elution: MeOH (0.05% DEA) in CO2 from 5% to 40%; Flow rate: 3 mL/min; Detector: PDA; Column Temp: 35° C.; Back Pressure: 100 Bar): Chiral purity: 100%.

Example 2. Synthesis of tert-butyl (S)-3-(2-((((9H-fluoren-9-yl)methoxy)carbonyl)amino)-3-(benzyloxy)-3-oxopropyl)benzoate

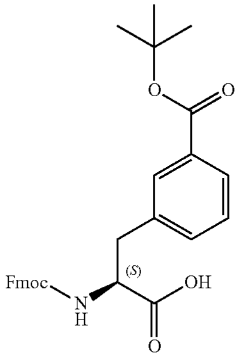

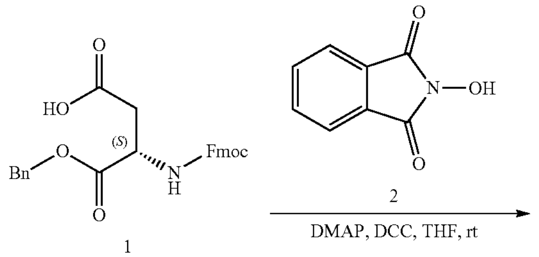

1

2

-continued

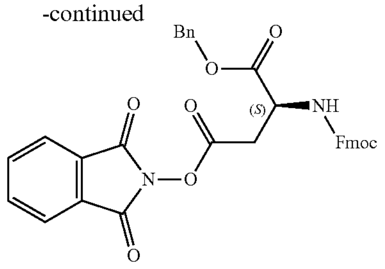

3

A mixture of compound 1 (90.0 g, 202 mmol, 1.00 eq), compound 2 (49.4 g, 303 mmol, 1.50 eq), DCC (50.0 g, 242 mmol, 49.0 mL, 1.20 eq), DMAP (1.23 g, 10.1 mmol, 0.0500 eq) in THF (100 mL) was degassed and purged with $N_2$ for 3 times, and then the mixture was stirred at 20° C. for 12 hrs under $N_2$ atmosphere. LC-MS (EW23957-10-P1B) showed the compound 1 was consumed completely, and desired mass was detected ($R_t$=1.046 min). The mixture was filtered, and the filtrate was concentrated in vacuo. The crude product was purified by reversed-phase HPLC (0.1% FA condition). Compound 3 (68.0 g, 115 mmol, 56.9% yield) was obtained as a white solid. LCMS $R_t$=1.046 min, m/z=613.1 $(M+23)^+$. $^1$HNMR (DMSO, 400 MHz) δ: 8.11 (d, J=8.4 Hz, 1H), 7.98-7.96 (m, 4H), 7.89 (d, J=7.6 Hz, 2H), 7.69 (d, J=7.6 Hz, 2H), 7.42-7.28 (m, 10H), 5.16 (d, J=2.0 Hz, 2H), 4.64-4.62 (m, 1H), 4.33-4.31 (m, 2H), 4.24-4.21 (m, 1H), 3.39-3.37 (m, 1H), 3.25-3.19 (m, 1H).

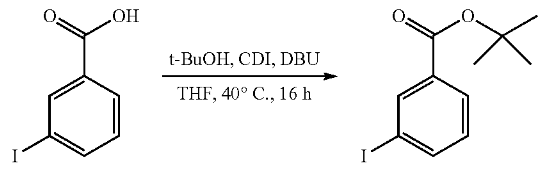

6 4

To a solution of compound 6 (100 g, 403 mmol, 1.00 eq) in THF (500 mL) was added CDI (71.9 g, 443 mmol, 1.10 eq) and the mixture was stirred for 0.5 h. 2-methylpropan-2-ol (387 g, 5.23 mol, 500 mL, 12.9 eq) and DBU (67.5 g, 443 mmol, 66.8 mL, 1.10 eq) were subsequently added to the reaction. The mixture was stirred at 40° C. for 11.5 hrs. TLC (Petroleum ether: Ethyl acetate=5/1) showed the compound 6 was consumed completely ($R_f$=0.15), and two main spots were observed ($R_f$=0.90, 0). $H_2O$ (500 mL) was added to the reaction. The mixture was extracted with EtOAc (500 mL*3). The combined organic layers were washed with saturated brine (500 mL*3), dried over $Na_2SO_4$, filtered and concentrated under reduced pressure to give a residue. The residue was purified by column chromatography ($SiO_2$, Petroleum ether/Ethyl acetate=0/1, $R_f$=0.90). Compound 4 (113 g, 371 mmol, 92.1% yield) was obtained as alight yellow oil. $^1$HNMR (DMSO, 400 MHz) δ: 8.16 (t, J=1.6 Hz, 1H), 7.97 (m, 1H), 7.89 (m, 1H), 7.30 (t, J=8.0 Hz, 1H), 1.53 (s, 9H).

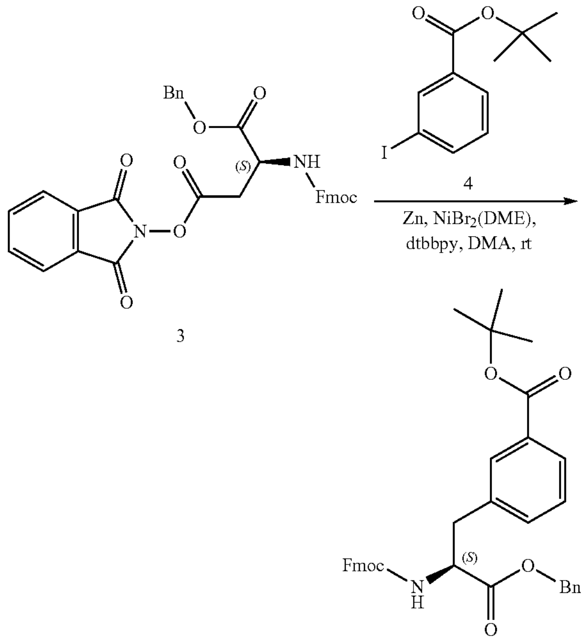

3

4

5

A solution of dibromonickel; 1,2-dimethoxyethane (2.85 g, 9.25 mmol, 7.03 $e^{-2}$ eq) and 4-tert-butyl-2-(4-tert-butyl-2-pyridyl)pyridine (2.48 g, 9.24 mmol, 7.03 $e^{-2}$ eq) in DMA (500 mL) was stirred at room temperature for 0.5 hr. Compound 3 (68.0 g, 115 mmol, 8.75 $e^{-1}$ eq), compound 4 (40.0 g, 131 mmol, 1.00 eq), dodecane (15.0 g, 88.0 mmol, 20.0 mL, 0.670 eq), Zn (30.0 g, 458 mmol, 3.49 eq) were added to the reaction. The mixture was stirred at 25° C. for 2.5 hrs. LC-MS (EW23957-16-P1A) showed Compound 3 was consumed completely, and desired mass was detected (R, =1.126 min). The reaction mixture was quenched by the addition of HCl (500 mL). The resulting mixture was extracted with EtOAc (500 mL*3). The combined organic layers were washed with saturated brine (500 mL*3), dried over $Na_2SO_4$, filtered and concentrated under reduced pressure to give a residue. The crude product was purified by reversed-phase HPLC (0.1% FA condition). Compound 5 (35.0 g, 60.5 mmol, 46.0% yield) was obtained as a yellow oil. LCMS $R_t$=1.126 min, m/z=623.2 $(M+46)^+$. $^1$HNMR ($CDCl_3$, 400 MHz) δ: 7.88 (d, J=7.6 Hz, 1H), 7.80-7.76 (m, 3H), 7.56 (t, J=7.2 Hz, 2H), 7.42-7.29 (m, 10H), 7.20-7.19 (m, 1H), 5.37 (d, J=8.0 Hz, 1H), 5.17 (d, J=2.8 Hz, 2H), 4.81-4.71 (m, 1H), 4.42-4.36 (m, 2H), 4.13-4.20 (m, 1H), 3.21-3.17 (m, 2H), 1.58 (s, 9H).

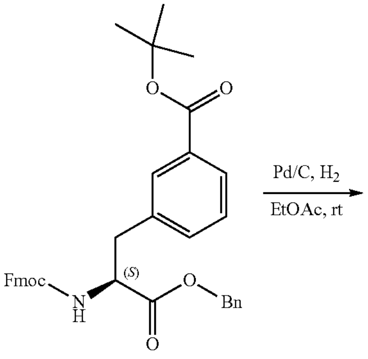

5

-continued

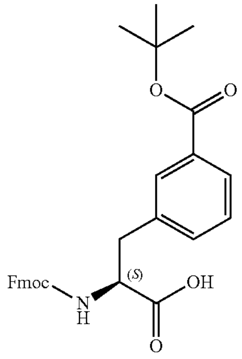

To a solution of compound 5 (35.0 g, 60.5 mmol, 1.00 eq) in EtOAc (50.0 mL) was added Pd/C (3.50 g, 10.0% purity). The mixture was stirred at 25° C. for 2 hrs under $H_2$ (15 psi) atmosphere. LC-MS (EW23957-19-P1A) showed that compound 5 was consumed, and desired mass was detected ($R_t$=0.991 min). The mixture was filtered, and the filtrate was concentrated in vacuo. The mixture was purified by reversed-phase HPLC (FA condition). The final product (23.5 g, 48.0 mmol, 79.2% yield, 99.6% purity) was obtained as a white solid. LCMS $R_t$=1.088 min, m/z=510. $(M+23)^+$. HPLC $R_t$=3.51 min, purity: 99.6%. $^1$HNMR (DMSO, 400 MHz) δ: 7.87-7.84 (m, 3H), 7.80-7.74 (m, 2H), 7.62-7.51 (m, 3H), 7.41-7.37 (m, 3H), 7.31-7.23 (m, 2H), 4.24-4.20 (m, 1H), 4.20-4.19 (m, 2H), 4.19-4.14 (m, 1H), 3.18-3.13 (m, 1H), 2.98-2.91 (m, 1H), 1.51 (s, 9H). SFC: Chiral purity: 99.5%.

Example 3. Synthesis of TfeGA

Step 1: (S)-2-(((benzyloxy)carbonyl)amino)-3-((tert-butoxycarbonyl)amino)propanoic acid

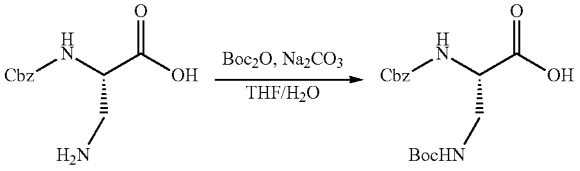 [SMILES: NC[C@H](NC(=O)OCc1ccccc1)C(=O)O ; "THF/H2O" ; CC(C)(C)OC(=O)NC[C@H](NC(=O)OCc1ccccc1)C(=O)O]

A mixture of (S)-3-amino-2-(((benzyloxy)carbonyl)amino)propanoic acid (20 g, 84 mmol), $(Boc)_2O$ (36.6 g, 168 mmol) and $Na_2CO_3$ (17.8 g, 168 mmol) in THF (400 mL) and water (250 mL) was stirred at room temperature for 3 h. The mixture was titrated with 1N HCl until the pH reached 3~4. The aqueous phase was extracted with DCM (3×500 mL). The organic layers were collected, dried, and concentrated to afford the crude product (28.5 g, 100% yield) as a white solid. MS (ESI): m/z=361.1 $[M+Na]^+$.

Step 2: Benzyl (S)-2-(((benzyloxy)carbonyl)amino)-3-((tert-butoxycarbonyl)amino) propanoate

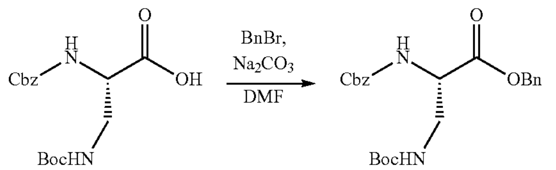

A mixture of (S)-2-(((benzyloxy)carbonyl)amino)-3-((tert-butoxycarbonyl)amino) propanoic acid (28.5 g, 84.3 mmol), benzyl bromide (21.6 g, 126.5 mmol) and $Na_2CO_3$ (17.8 g, 168.7 mmol) in DMF (500 mL) was stirred at room temperature for 3 h. The reaction mixture was diluted with ethyl acetate (2 L), washed with brine (5×500 mL), dried over $Na_2SO_4$ and filtered. The filtrate was concentrated and the crude mixture was purified by silica gel column chromatography (eluted with hexane/ethyl acetate=4:1, V/V) to afford the product (35.5 g, 99% yield) as a colorless oil. MS (ESI): m/z=451.1 [M+Na]+.

Step 3: Benzyl (S)-3-amino-2-(((benzyloxy)carbonyl)amino)propanoate

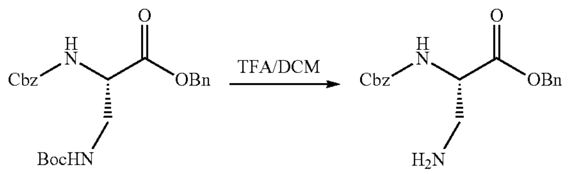 [SMILES: CC(C)(C)OC(=O)NC[C@H](NC(=O)OCc1ccccc1)C(=O)OCc1ccccc1 ; NC[C@H](NC(=O)OCc1ccccc1)C(=O)OCc1ccccc1]

A mixture of benzyl (S)-2-(((benzyloxy)carbonyl)amino)-3-((tert-butoxycarbonyl) amino)propanoate (35.5 g, 82.9 mmol) in TFA (100 mL) and DCM (100 mL) was stirred at room temperature for 3 h, then solvent was removed under reduced pressure. The mixture was titrated with sat. $NaHCO_3$ until the pH reached 8-9. The aqueous phase was extracted with DCM (3×1000 mL). The organic layers were combined, dried, and concentrated to afford the product (26.8 g, 98.5% yield) as a colorless oil. MS (ESI): m/z=329.1 $[M+H]^+$.

Step 4: Benzyl (S)-2-(((benzyloxy)carbonyl)amino)-3-((2-(tert-butoxy)-2-oxoethyl)amino) propanoate

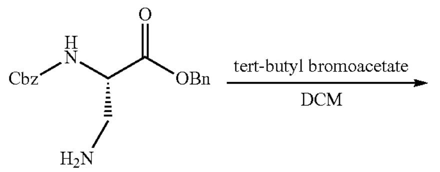

-continued

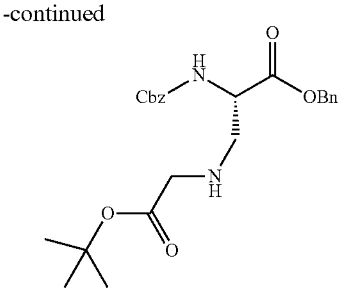

A mixture of benzyl (S)-3-amino-2-(((benzyloxy)carbonyl)amino)propanoate (13.5 g, 41.1 mmol) and tert-butyl 2-bromoacetate (8.03 g, 41.1 mmol) in DCM (250 mL) was stirred at room temperature for 2 days. $Et_2NH$ (3 g, 41.1 mmol) was added and the reaction mixture was stirred at room temperature for 1 h. The mixture was titrated sat. $NaHCO_3$ until pH reached 8-9. The aqueous phase was extracted with DCM (3×500 mL). The organic layers were combined, dried, and concentrated. The crude mixture was purified by silica gel column chromatography (eluted with hexane/ethyl acetate=4:1, V/V) to afford the product (8.2 g, 45% yield) as a colorless oil. MS (ESI): m/z=443.2 $[M+H]^+$.

Step 5: Benzyl (S)-2-(((benzyloxy)carbonyl)amino)-3-((2-(tert-butoxy)-2-oxoethyl) (2,2,2-trifluoroethyl) amino)propanoate

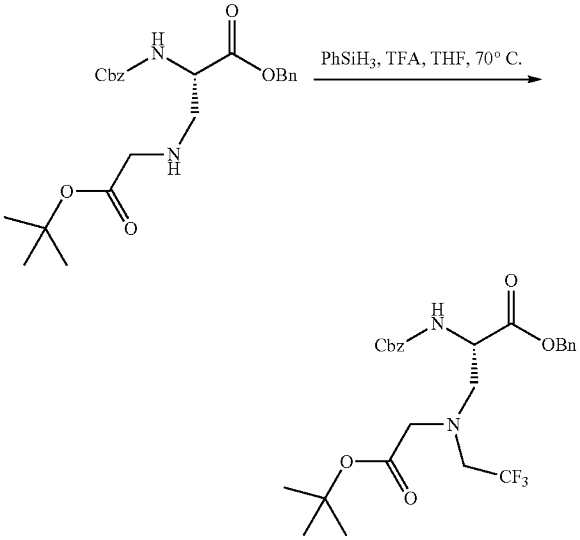

To an oven-dried 500 ml round-bottomed flask fitted with a water condenser under an argon atmosphere (balloon) was added tetrahydrofuran (400 mL) and benzyl (S)-2-(((benzyloxy)carbonyl)amino)-3-((2-(tert-butoxy)-2-oxoethyl) amino)propanoate (11.5 g, 26 mmol) as the free base. The reaction flask was heated in an oil bath at 70° C. Phenylsilane (14.0 g, 130 mmol) in THF (25 mL) was added immediately via syringe, followed by TFA (14.1 g, 123.6 mmol) in THF (25 mL). The reaction was stirred at reflux for 4 h. The mixture was concentrated and titrated with sat. $NaHCO_3$ until pH reached 8-9. The aqueous phase was extracted with DCM (3×500 mL). The organic layers were combined, dried, and concentrated. The crude mixture was purified by silica gel column chromatography (eluted with hexane/ethyl acetate=6:1, V/V) to afford the product (11.2 g, 82% yield) as a colorless oil. MS (ESI): m/z=525.0 $[M+H]^+$.

Step 6: (S)-2-((((9H-fluoren-9-yl)methoxy)carbonyl)amino)-3-((2-(tert-butoxy)-2-oxoethyl)(2,2,2-trifluoroethyl)amino)propanoic acid

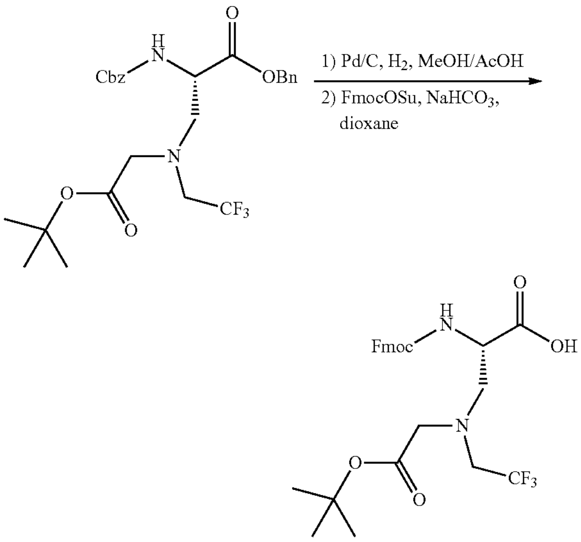

A mixture of benzyl (S)-2-(((benzyloxy)carbonyl)amino)-3-((2-(tert-butoxy)-2-oxoethyl)(2,2,2-trifluoroethyl)amino)propanoate (5.5 g, 10.5 mmol) and palladium on carbon (3 g, 10%) in MeOH (200 mL) and AcOH (8 mL) was attached to a hydrogenation apparatus. The system was evacuated and then refilled with hydrogen. The mixture was stirred at room temperature for 16 h. The reaction mixture was filtered. The filtrate was concentrated and re-dissolved in dioxane (150 mL) and water (150 mL). FmocOSu (3.36 g, 10 mmol) and $NaHCO_3$ (4.41 g, 52.5 mmol) were added. The mixture was stirred at room temperature for 16 h. The mixture was titrated with 0.5 N HCl until pH reached 4. The aqueous phase was extracted with ethyl acetate (3×500 mL). The organic layers were combined, dried, and concentrated. The crude mixture was purified by combiflash on C18 (0-80% $MeCN/H_2O$) to give the product (3.5 g, 64% yield) as a white solid. MS (ESI): m/z=523.0 $[M+H]^+$. $^1H$ NMR, 400 MHz, DMSO-d6, δ 12.73 (s, 1H); 7.90 (d, J=7.6 Hz, 2H); 7.72 (d, J=7.6 Hz, 2H); 7.59 (d, J= 8 Hz, 1H); 7.42 (t, J=7.2 Hz, 2H); 7.30 (t, J=7.2 Hz, 2H); 4.29-4.21 (m, 3H); 4.14-4.09 (m, 1H); 3.54-3.42 (m, 4H); 3.19 (dd, J1=14.2 Hz, J2=4.8 Hz, 1H); 3.00-2.95 (m, 1H); 1.42 (s, 9H).

Example 4. Provided Technologies can Provide Improved Properties and/or Activities Among other things, provided amino acids when utilized for preparing products, e.g., peptides, can provided improved properties and/or activities. For example, various peptides comprising residues of provided amino acids were prepared (e.g., using Fmoc-based solid phase synthesis) and assessed. Among other things, the present disclosure demonstrates that peptides comprising provided amino acid residues (e.g., TfeGA, 2COOHF, 3COOHF, etc.) can provide higher lipophilicity as demonstrated by increased Log D (by, e.g., in this Example, about 0.15 or more, about 0.2 to about 0.3, etc., in CHI Log D as measured using the procedure below; tested peptides in this Example contain 14 amino acid residues and are stapled, and provided amino acid residues and reference residues are in the middle region of the peptides) compared to reference peptides comprising reference amino acid residues (e.g., Asp) instead of provided amino acids. In some embodiments, peptides comprising provided amino acid residues provide significantly improved cell delivery compared to reference peptides. In various embodiments, peptides comprising provided amino acid residues, in addition to improved properties such as lipophilicity, also provide comparable or improved solubility and/or target binding compared to reference peptides comprising reference amino acid residues (e.g., Asp) instead of provided amino acid residues.

In some embodiments, Log D was measured using a CHI Log D procedure: 3 uL of a 0.2 mM solution of peptide in 90% DMSO was injected onto a Phenonenex Gemini 3 um C18 110A column (50×3 mm), eluting with a gradient of 50 mM ammonium acetate pH 7.4 and acetonitrile. The retention time was compared to a standard calibration solution of 10 compounds to derive CHI Log D:

| Compound | Gradient tR at pH 7.4 | CHI at pH 7.4 |
|---|---|---|
| Theophylline | 1.671 | 18.40 |
| Phenyltetrazole | 1.768 | 23.60 |
| Benzimidazole | 1.911 | 34.30 |
| Colchicine | 2.132 | 42.00 |
| Phenyltheophylline | 2.271 | 51.20 |
| Acetophenone | 2.475 | 65.10 |
| Indole | 2.642 | 71.50 |
| Propiophenone | 2.734 | 77.40 |
| Butyrophenone | 2.932 | 87.50 |
| Valerophenone | 3.113 | 96.20 |

In some embodiments, it was confirmed that various peptides, e.g., stapled peptides, comprising residues of amino acids described herein can provide higher affinity than reference peptides that comprise a reference amino acid, e.g., a natural amino acid such as Asp or Glu, but are otherwise identical.

Example 5. Synthesis of Compound 2-2

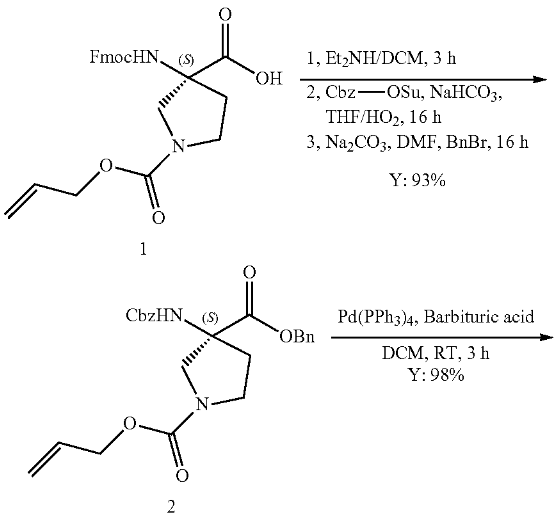

-continued

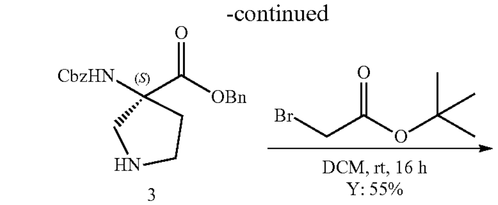

3

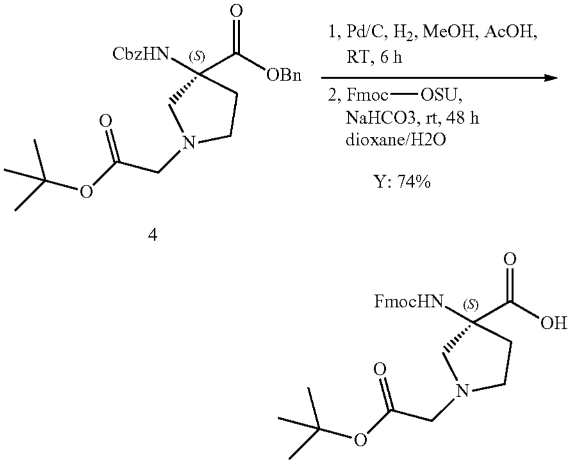

4

Cmpound-2-2

Step 1: 1-Allyl 3-benzyl (S)-3-(((benzyloxy)carbonyl)amino)pyrrolidine-1,3-dicarboxylate (2). A mixture of (S)-3-((((9H-fluoren-9-yl)methoxy)carbonyl)amino)-1-((allyloxy) carbonyl)pyrrolidine-3-carboxylic acid (20 g, 45.9 mmol) in DCM (300 mL) and $Et_2N$ (300 mL) was stirred at room temperature for 3 h. The mixture was concentrated and dissolved into THF (400 mL) and water (400 mL). Cbz-OSU (17.1 g, 68.9 mmol) and $NaHCO_3$ (7.71 g, 91.7 mmol) was add. The reaction mixture was stirred at room temperature for 16 h. The mixture was adjusted pH to 3~4 with 1N HCl. The aqueous phase was extracted with EtOAc (3×800 mL). The desired EtOAc layer was then dried, concentrated to afford the crude product and dissolved into DMF (500 mL). BnBr (15.69 g, 91.7 mmol) and $Na_2CO_3$ (9.72 g, 91.7 mmol) was added and stirred at room temperature for 16 h. The reaction mixture was diluted with ethyl acetate (2 L), washed with brine (5×500 mL), dried over $Na_2SO_4$, concentrated and purified by silica gel column chromatography (eluted with hexane/ethyl acetate=2:1, V/V) to afford the product (18.7 g, 93% yield) as a brown oil. MS (ESI): m z=439.1 $[M+H]^+$.

Step 2: Benzyl (S)-3-(((benzyloxy)carbonyl)amino)pyrrolidine-3-carboxylate (3). A mixture of 1-allyl 3-benzyl (S)-3-(((benzyloxy)carbonyl)amino)pyrrolidine-1,3-dicarboxylate (9.35 g, 21.3 mmol), $Pd(PPh_3)_4$(4.93 g, 4.3 mmol) and Barbituric acid (5.46 g, 42.7 mmol) in DCM (300 mL) under Ar was stirred at room temperature for 3 h. The mixture was concentrated and purified by silica gel column chromatography (eluted with DCM/MeOH=10:1, V/V) to afford the product (7.5 g, 98% yield) as a brown oil. MS (ESI): m z=355.1 $[M+H]^+$.

Step 3: Benzyl (S)-3-(((benzyloxy)carbonyl)amino)-1-(2-(tert-butoxy)-2-oxoethyl) pyrrolidine-3-carboxylate (4). A mixture of benzyl (S)-3-(((benzyloxy)carbonyl)amino)pyrrolidine-3-carboxylate (15 g, 42.4 mmol) and tert-butyl 2-bromoacetate (16.5 g, 84.7 mmol) in DCM (400 mL) was stirred at room temperature for 16 h. $Et_2NH$ (12.4 g, 169.5 mmol) was added and stirred at room temperature for 3 h. The mixture was adjusted PH to 8-9 with sat. $NaHCO_3$. The aqueous phase was extracted with DCM (3×500 mL). The desired DCM layers was then dried, concentrated purified by silica gel column chromatography (eluted with hexane/ethyl acetate=2:1, V/V) to afford the product (10.9 g, 55% yield) as a yellow oil. MS (ESI): m z=469.2 $[M+H]^+$.

Step 4: (S)-3-((((9H-fluoren-9-yl)methoxy)carbonyl)amino)-1-(2-(tert-butoxy)-2-oxoethyl)pyrrolidine-3-carboxylic acid (compound-2-2). A mixture of benzyl (S)-3-(((benzyloxy)carbonyl)amino)-1-(2-(tert-butoxy)-2-oxoethyl)pyrrolidine-3-carboxylate (14.5 g, 31 mmol) and Palladium on carbon (6 g, 10%) in MeOH (600 mL) and AcOH (20 mL) was attached to a hydrogenation apparatus. The system was evacuated and then refilled with hydrogen. The mixture was stirred at room temperature for 6 h. The reaction mixture was filtered out and the filtrate was concentrated and dissolved into dioxane (300 mL) and water (300 mL). FmocOSu (20.88 g, 62 mmol) and $NaHCO_3$ (13 g, 155 mmol) was added. The mixture was stirred at room temperature for 48 h. The mixture was adjusted PH to 3-4 with 0.5 N HCl. The aqueous phase was extracted with DCM (3×500 mL). The desired DCM layers was then dried and concentrated. The resulting solid was recrystallized from methanol:EtOAc:PE=1:1:1 to give the product (10.62 g, 74% yield) as a white solid. MS (ESI): m/z=467.0 [M+H]+. 400 MHz, DMSO-d6, δ 7.90-7.89 (m, 3H); 7.73 (d, J=7.6 Hz, 2H); 7.42 (t, J=7.2 Hz, 2H); 7.34 (t, J=7.4 Hz, 2H); 4.30-4.20 (m, 3H); 3.27-3.18 (m, 2H); 3.13 (d, J=10 Hz, 1H); 2.93 (d, J=10 Hz, 1H); 2.84-2.79 (m, 1H); 2.66-2.60 (m, 1H); 2.24-2.17 (m, 1H); 2.06-2.00 (m, 1H); 1.41 (s, 9H). Purity by HPLC: 99.78% (214 nm), RT=16.29 min; Mobile Phase: A: Water (0.05% TFA) B: ACN (0.05% TFA); Gradient: 20% B for 1 min, increase to 80% B within 20 min, increase to 95% B within 1 min, hold for 5 min, back to 20% B within 0.1 min. Flow Rate: 1 mL/min; Column: XBridge Peptide BEH C18, 4.6*150 mm, 3.5 μm. Column Temperature: 40° C. Purity by SFC: 99.83%, Column AD-H: RT 1.71 min; 100%, Column AS-H: RT 3.53 min; 100%, Column OD-H: RT 1.48 min; 99.70%, Column OJ-H: RT 2.42 min.

Example 6. Synthesis of a Compound

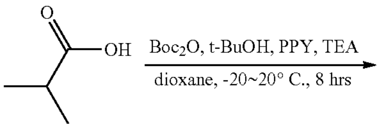

1

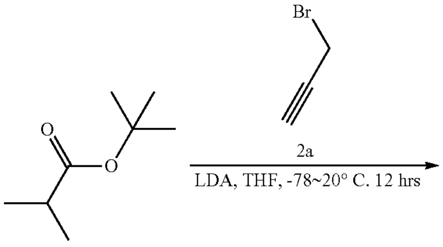

2

-continued

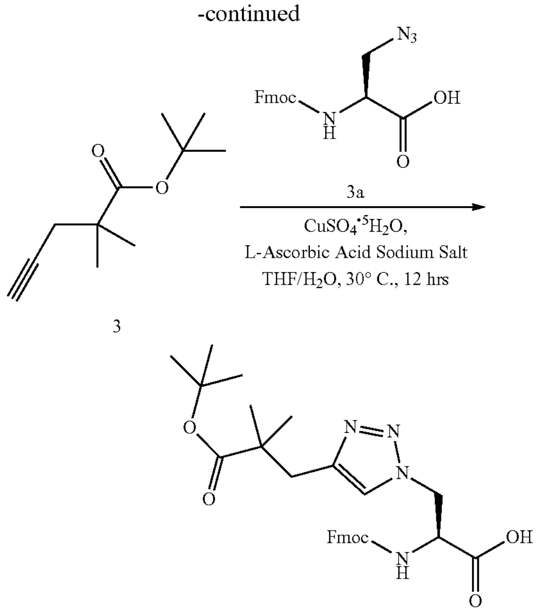

3

4

Preparation of compound 2. A mixture of compound 1 (30.0 g, 340 mmol, 31.5 mL, 1 eq), t-BuOH (27.7 g, 374 mmol, 35.8 mL, 1.1 eq), TEA (68.9 g, 681 mmol, 94.7 mL, 2 eq), and 4-pyrrolidin-1-ylpyridine (2.52 g, 17.0 mmol, 0.05 eq) in dioxane (20 mL) was stirred at −20° C. for 0.5 hr and then $Boc_2O$ (96.6 g, 442 mmol, 101 mL, 1.3 eq) was added. The resulting mixture was stirred at 20° C. for 7.5 hrs. TLC (petroleum ether/ethyl acetate=10/1) showed starting material ($R_f$=0.1) was consumed completely. The mixture was diluted with DCM (100 mL), washed with 2N HCl (100 mL*2) and sat.aq.$NaHCO_3$ (100 mL), dried over anhydrous sodium sulfate and filtered. The filtrate was purified through distillation (62° C.) under reduced pressure (vacuum degree: −0.95 MPa) to give compound 2 (27.0 g, 187 mmol, 55.0% yield) as a colorless oil. $^1$H NMR: 400 MHz CDC13: δ=3.71 (s, 1H), 2.39-2.46 (m, 1H), 1.45 (s, 9H), 1.12 (d, J=8.0 Hz, 6H).

Preparation of compound 3. To a solution of i-$Pr_2NH$ (28.2 g, 279 mmol, 39.4 mL, 1.15 eq) in THF (80.0 mL) was added drop-wise n-BuLi (2.5 M, 106 mL, 1.1 eq) at −78° C. and stirred for 1 hr. The fresh prepared LDA was added drop-wise to a solution of compound 2 (35.0 g, 242 mmol, 1 eq) in THF (80.0 mL) at 0° C. After addition, the reaction was stirred at 20° C. for 1 hr before cooling back to 0° C. A solution of compound 2a (39.7 g, 266 mmol, 28.7 mL, 80% purity, 1.1 eq) in THF (20.0 mL) was added drop-wise. The resulting mixture was stirred at 20° C. for 10 hrs. TLC (petroleum ether/ethyl acetate=5/1) showed new spot ($R_f$=0.65) formed. The mixture was quenched with water (150 mL), the organic phase was separated and the aqueous layer extracted with MTBE (3×60.0 mL). The combined organic layers were washed with a saturated aqueous NaCl solution, dried over sodium sulphate, filtered and concentrated in vacuo. The obtained crude oil was distilled (94° C., −0.95 Mpa) to give compound 3 (27.0 g, 148 mmol, 61.0% yield) as a colorless oil. $^1$H NMR: 400 MHz $CDCl_3$: δ=2.39 (d, J=8.0 Hz, 2H), 1.99 (t, J=4.0 Hz, 1H), 1.45 (s, 9H), 1.24 (s, 6H).

Preparation of compound 4. To a solution of compound 3 (16.7 g, 119 mmol, 1.2 eq) in THF (200 mL) was added a solution of $CuSO_4 \cdot 5H_2O$ (868 mg, 3.48 mmol, 0.035 eq) and L-Ascorbic Acid Sodium Salt (5.12 g, 25.8 mmol, 0.26 eq) in $H_2O$ (100 mL) followed by addition of a solution of compound 3a (35 g, 99.33 mmol, 1 eq) in THF (200 mL) and $H_2O$ (200 mL). The resulting mixture was stirred at 30° C. for 12 hrs. LCMS showed desired MS (Rt=0.977 min) was detected. The mixture was concentrated under vacuum to remove THF and white solids were precipitated out, filtered. The solid was triturated with MeOH/$H_2O$ (1/1, 2 L) to give compound 4 (22.0 g, 39.7 mmol, 40.0% yield, 96.5% purity) as a white solid. In one LCMS run: Rt=0.977 min, m/z: $[M+H]^+$=535.4. In another LCMS run: Rt=0.956 min, m/z: $[M+H]^+$=535.3. In a HPLC run: Rt=2.601 min. $^1$H NMR: 400 MHz DMSO-d6: δ=7.88 (d, J=8.0 Hz, 2H), 7.63-7.71 (m, 4H), 7.41 (t, J=8.0 Hz, 2H), 7.32 (t, J=8.0 Hz, 2H), 4.75 (s, 1H), 4.33-4.68 (m, 2H), 4.10-4.29 (m, 3H), 2.75 (s, 2H), 1.36 (s, 9H), 1.02 (d, J=2.4 Hz, 1H).

Example 7. Synthesis of a Compound

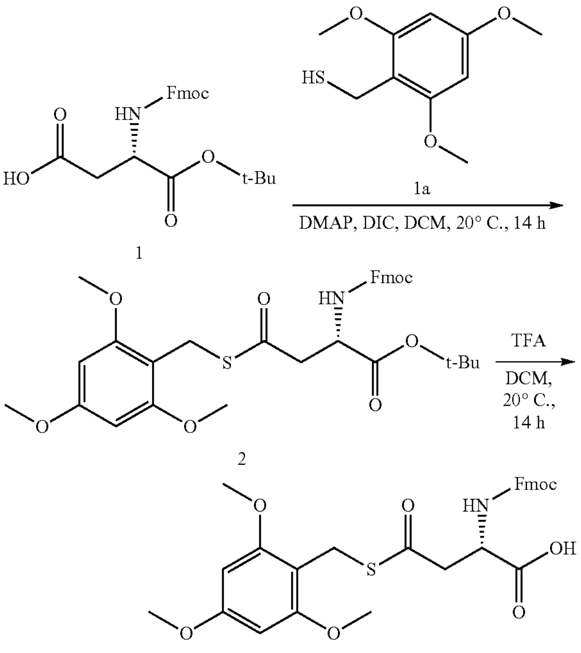

1

2

3

To a solution of compound 1a (5.00 g, 23.3 mmol, 1.00 eq), compound 1 (14.4 g, 35.0 mmol, 1.50 eq) and DMAP (142 mg, 1.17 mmol, 0.050 eq) in dichloromethane (80.0 mL) was added DIC (3.59 g, 28.4 mmol, 4.41 mL, 1.22 eq) under a nitrogen atmosphere. The reaction was stirred at 20° C. for 14 hrs. LCMS showed the starting material was consumed completely with desired mass (in one run, Rt=1.080 min) was detected. TLC (Petroleum ether:Ethyl acetate=3:1) also showed the starting material (Rf=0.89) was consumed completely with six new spots ($R_f$=0.37) formed. The mixture was filtered and the precipitate was washed with dichloromethane (10.0 mL*3). The filtrate was concentrated under reduced pressure. The residue was purified by column chromatography ($SiO_2$, Petroleum ether: Ethyl acetate=50:1 to 2:1, $R_f$=0.37). The compound 2 (14.9 g, crude) was obtained as yellow oil. LCMS: product: Rt=1.080 min, m/z=630 $(M+H)^+$. $^1$HNMR: $CDCl_3$, 400 MHz: δ: 7.71 (d, J=7.6 Hz, 2H), 7.62 (d, J=7.6 Hz, 2H), 7.41 (t, J=7.6 Hz, 2H), 7.32 (td, $J_1$=7.6 Hz, $J_2$=0.8 Hz, 2H), 6.10

(s, 2H), 5.80 (d, J=8.4 Hz, 1H), 4.55-4.51 (m, 1H), 4.42-4.36 (m, 2H), 4.30-4.22 (m, 3H), 3.80-3.79 (m, 9H), 3.24-3.04 (m, 2H), 1.49 (s, 9H).

To a solution of compound 2 (12.9 g, 21.2 mmol, 1.00 eq) in dichloromethane (45.0 mL) was added TFA (23.1 g, 202 mmol, 15.0 mL, 9.54 eq), the reaction was stirred at 20° C. for 14 hrs. LCMS showed the starting material was consumed completely with desired mass (Rt=0.828 min, m/z=550) was detected. The volatiles (Dichloromethane, TFA) was removed under reduced pressure. The crude product was purified by reversed-phase HPLC (FA). Compound 3 (5.52 g, 9.64 mmol, 45.4% yield, 96.3% purity) was obtained as light yellow solid. In a LCMS run: product: Rt=0.828 min, m/z=550.2 $(M-H)^-$. In another LCMS run: product: $R_t$=0.835 min, m/z=550.2 $(M-H)^-$. HPLC: product: $R_t$=3.566 min, purity: 96.3%. $^1$HNMR: $CDCl_3$, 400 MHz: δ: 7.77 (d, J=7.6 Hz, 2H), 7.61 (d, J=7.2 Hz, 2H), 7.41 (t, J=7.6 Hz, 2H), 7.32 (td, $J_1$=7.6 Hz, $J_2$=0.8 Hz, 2H), 6.10 (s, 2H), 5.82 (d, J=8.0 Hz, 1H), 4.70-4.67 (m, 1H), 4.44-4.39 (m, 2H), 4.28-4.26 (m, 2H), 4.25-4.23 (m, 1H), 3.80 (s, 9H), 3.35-3.31 (m, 2H).

Example 8. Synthesis of a Compound

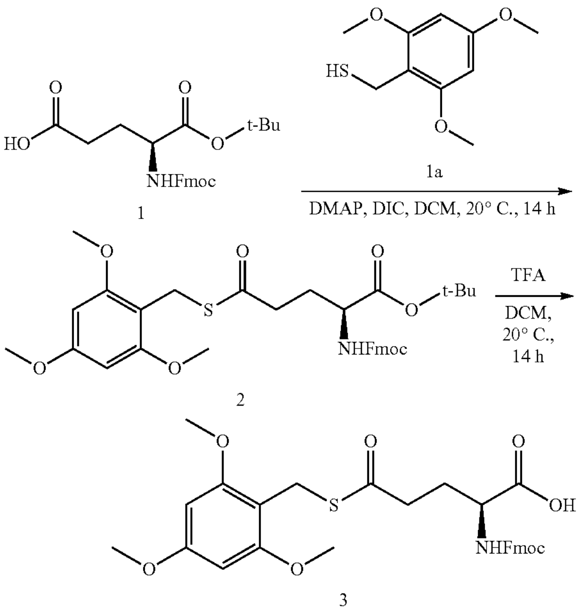

To a solution of compound 1a (5.00 g, 23.3 mmol, 1.00 eq), compound 1 (14.8 g, 35.0 mmol, 1.50 eq) and DMAP (142 mg, 1.17 mmol, 0.050 eq) in Dichloromethane (80.0 mL) was added DIC (3.59 g, 28.4 mmol, 4.41 mL, 1.22 eq) under a nitrogen atmosphere. The reaction was stirred at 20° C. for 14 hrs. LCMS showed the starting material was consumed completely with desired mass (Rt=1.081 min) was detected. TLC (Petroleum ether:Ethyl acetate=3:1) also showed the starting material (Rf=0.88) was consumed completely with six new spots (Rf=0.30) formed. The mixture was filtered and the precipitate was washed with Dichloromethane (10.0 mL*3). The filtrate was concentrated under reduced pressure. The residue was purified by column chromatography ($SiO_2$, Petroleum ether:Ethyl acetate=50:1 to 2:1, Rf=0.30). The compound 2 (15.8 g, crude) was obtained as colorless oil. LCMS: product: Rt=1.081 min, m/z=644 $(M+H)^+$. $^1$HNMR: $CDCl_3$, 400 MHz δ: 7.77 (d, J=7.2 Hz, 2H), 7.61 (d, J=7.6 Hz, 2H), 7.40 (t, J=7.6 Hz, 2H), 7.32 (tt, $J_1$=7.6 Hz, $J_2$=1.2 Hz, 2H), 6.10 (s, 2H), 5.39 (d, J=8.0 Hz, 1H), 4.47-4.34 (m, 2H), 4.31-4.25 (m, 1H), 4.24-4.20 (m, 3H), 3.80 (s, 9H), 2.67-2.53 (m, 2H), 2.28-0.20 (m, 1H), 2.03-1.99 (m, 1H), 1.48 (s, 9H).

To a solution of compound 2 (15.8 g, 25.4 mmol, 1.00 eq) in dichloromethane (45.0 mL) was added TFA (23.1 g, 202 mmol, 15.0 mL, 7.97 eq), the reaction was stirred at 20° C. for 14 hrs. LCMS showed the starting material was consumed completely with desired mass (Rt=0.829 min, m/z=564) was detected. The volatiles (Dichloromethane, TFA) was removed under reduced pressure. The crude product was purified by reversed-phase HPLC (FA). Compound 3(6.57 g, 11.4 mmol, 45.1% yield, 98.7% purity) was obtained as white solid. In a LCMS run: product: Rt=0.829 min, m/z=564.3 $(M-H)^-$. In another LCMS run: product: Rt=0.838 min, m/z=564.3 $(M-H)^-$. In a HPLC run: product: Rt=3.593 min, purity: 98.7%. $^1$HNMR: $CDCl_3$, 400 MHz: δ: 7.76 (d, J=7.6 Hz, 2H), 7.60 (d, J=7.2 Hz, 2H), 7.40 (t, J=7.6 Hz, 2H), 7.32 (t, $J_1$=7.6 Hz, 2H), 6.10 (s, 2H), 5.53 (d, J=8.0 Hz, 1H), 4.53-4.46 (m, 3H), 4.27-4.21 (m, 3H), 3.79 (s, 9H), 2.77-2.53 (m, 2H), 2.33-2.28, in, 1H), 2.16-2.04, in. 1H).

While various embodiments have been described and illustrated herein, those of ordinary skill in the art will readily envision a variety of other means and/or structures for performing the functions and/or obtaining the results and/or one or more of the advantages described in the present disclosure, and each of such variations and/or modifications is deemed to be included. More generally, those skilled in the art will readily appreciate that all parameters, dimensions, materials, and configurations described herein are meant to be example and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described in the present disclosure. It is, therefore, to be understood that the foregoing embodiments are presented by way of example only and that, provided technologies, including those to be claimed, may be practiced otherwise than as specifically described and claimed. In addition, any combination of two or more features, systems, articles, materials, kits, and/or methods, if such features, systems, articles, materials, kits, and/or methods are not mutually inconsistent, is included within the scope of the present disclosure.

The invention claimed is:

1. A compound, wherein the compound is

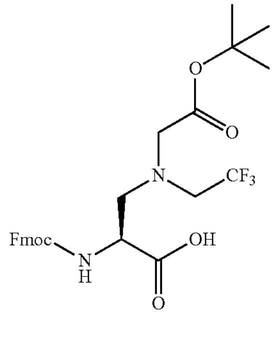

or a salt thereof,

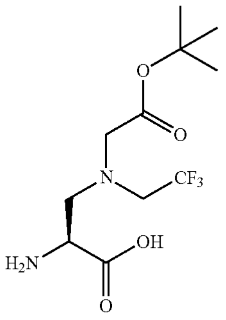 [SMILES: CC(C)(C)OC(=O)CN(C[C@H](N)C(=O)O)CC(F)(F)F]
or a salt thereof, or is
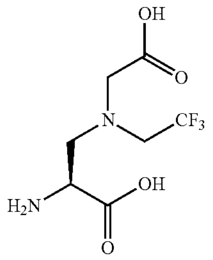 [SMILES: N[C@@H](CN(CC(=O)O)CC(F)(F)F)C(=O)O]
or a salt thereof.
2. The compound of claim 1, wherein the compound is
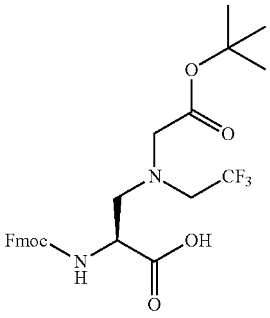
or a salt thereof.
3. The compound of claim 1, wherein the compound is
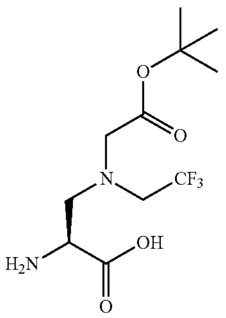 [SMILES: CC(C)(C)OC(=O)CN(C[C@H](N)C(=O)O)CC(F)(F)F]
or a salt thereof.
4. The compound of claim 1, wherein the compound is
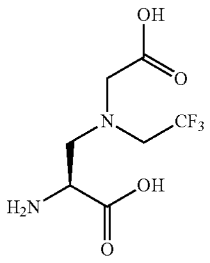 [SMILES: N[C@@H](CN(CC(=O)O)CC(F)(F)F)C(=O)O]
or a salt thereof.
5. A method for preparing a peptide, comprising utilizing
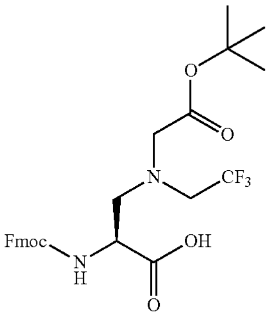
or a salt thereof,
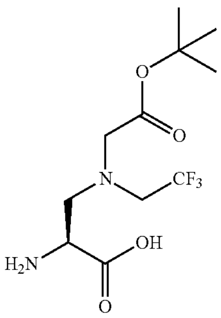 [SMILES: CC(C)(C)OC(=O)CN(C[C@H](N)C(=O)O)CC(F)(F)F]
or a salt thereof, or

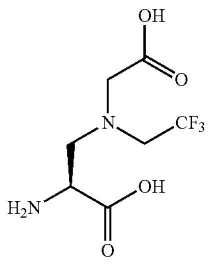 [SMILES: N[C@@H](CN(CC(=O)O)CC(F)(F)F)C(=O)O]
or a salt thereof.
6. The method of claim 5, comprising utilizing
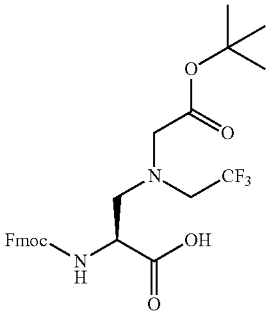
or a salt thereof.
7. The method of claim 5, comprising utilizing
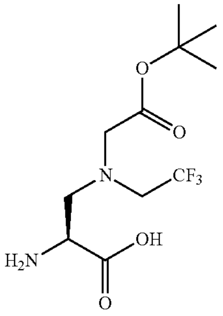 [SMILES: CC(C)(C)OC(=O)CN(C[C@H](N)C(=O)O)CC(F)(F)F]
or a salt thereof.
8. The method of claim 5, comprising utilizing
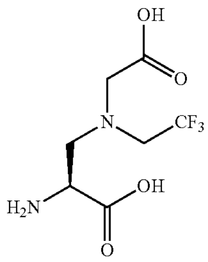 [SMILES: N[C@@H](CN(CC(=O)O)CC(F)(F)F)C(=O)O]
or a salt thereof.
* * * * *